(12) United States Patent
Grasso et al.

(10) Patent No.: US 6,777,388 B1
(45) Date of Patent: Aug. 17, 2004

(54) LEPTIN-RELATED PEPTIDES

(75) Inventors: Patricia Grasso, Albany, NY (US); Daniel W. Lee, Schenectady, NY (US); Matthew C. Leinung, Albany, NY (US)

(73) Assignee: CLF Medical Technology Acceleration Program, Inc., Clifton Park, NY (US)

( * ) Notice: Subject to any disclaimer, the term of this patent is extended or adjusted under 35 U.S.C. 154(b) by 0 days.

(21) Appl. No.: 09/377,081

(22) Filed: Aug. 19, 1999

Related U.S. Application Data

(60) Provisional application No. 60/097,457, filed on Aug. 21, 1998.

(51) Int. Cl.[7] .................. A61K 38/08; A61K 38/10; C07K 14/475; C07K 14/52
(52) U.S. Cl. ................... 514/16; 514/14; 530/326; 530/329
(58) Field of Search ................ 514/2, 12, 16, 514/14; 530/300, 326, 329, 350

(56) References Cited

FOREIGN PATENT DOCUMENTS

| GB | 2 292 382 A | 2/1996 |
|---|---|---|
| WO | WO 96/34885 | 11/1996 |
| WO | WO 97/46585 | 12/1997 |
| WO | WO 97/48419 | 12/1997 |
| WO | WO 98/12224 | 3/1998 |
| WO | WO 98/17626 | 4/1998 |
| WO | WO 98/18486 | 5/1998 |
| WO | WO 98/24896 | 6/1998 |

OTHER PUBLICATIONS

Grasso et al., "In vivo effects of Leptin–related synthetic peptides on body weight and food intake in female ob/ob mice: localization of Leptin activity to domains between amino acid residues 106–140" Endocrinology 138(4):1413–1418 (1997).

Martinez et al., "Role of fragment peptides from ob protein on body weight and thermogenesis control: a screening" Journal of Physiology and Biochemistry 52(2): 123–124 (1996).

Fruhbeck et al., "Age–related differences in the thermogenic and ponderal effects of fragment peptides from the rat ob protein." Regulatroy Peptides 73(2) 83–87 (1998).

Sampson et al., "A 35 amino acid fragment of leptin inhibits feeding in the rat" Endocrinology 137(11): 5182–5185 (1996).

Grasso et al., "Epitope mapping of secreted mouse Leptin utilizing peripherally administered synthetic peptides" Regulatory Peptides 85(23): 93–100 (1999).

Malendowics et al., "Leptin(116–130) enhances the proliferative activity of immature rat adrenal cortex." Medical Science Research 27: 675–676 (1999).

Grasso et al., "Inhibitory Effects of Leptin–Related Synthetic Peptide 116–130 on Food Intake and Body Weight Gain in Female C57BL/6J ob/ob Mice May Not Be Mediated by Peptide Activation of the Long Isoform of the Leptin Receptor." Diabetes 48:2204–2209 (1999).

Gonzalez et al., "Effect of acute immunoneutralization of endogenous leptin on prolactin an LH secretion during the afternoon of pro–oestrus or in steroid–treated ovariectomized female rats." Journal of Reproduction and Fertility 118: 39–45 (2000).

Gonzalez et al., "Leptin 116–130 Stimulates Prolactin and Luteinizing Hormone Secretion in Fasted Adult Male Rats." Neuroendocrinology 70:213–220 (1999).

Grasso et al. 1997 Eastern Great Lakes Endocrine Symposium. (Albany, NY) Poster Abstract. Nov. 3, 1997.

Grasso et al. 80th Annual Meeting of the Endocrine Society. Poster Abstract. 1998.

Grasso et al. 81st Annual Meeting of the Endocrine Society, San Diego CA. Post Abstract. Jun. 12–15, 1999.

*Primary Examiner*—Christine J. Saoud
(74) *Attorney, Agent, or Firm*—Mintz, Levin, Cohn, Ferris, Glovsky and Popeo, P.C.; Ivor R. Elrifi, Esq.; Naomi S. Biswas, Esq.

(57) ABSTRACT

The present invention relates to methods and compositions containing novel leptin peptides, preferably for the modulation of body mass (i.e., weight), more specifically for novel diagnostic and therapeutic applications in homeostasis of body weight and adipose tissue mass.

6 Claims, 21 Drawing Sheets

```
  1           5           10          15          20          25          30          35
  M C W R P L C R F L W L W S Y L S Y V Q A V P I Q K V Q D D T K T L I
  1_____21
            SIGNAL SEQUENCE                     21_____35
                                                                    31_____

LEPTIN-RELATED PEPTIDES

RELATED APPLICATIONS

This application claims priority to U.S. Provisional Application Serial No. 60/097,457 filed Aug. 21, 1998, entitled "Synthetic Leptin-Related Peptides", which is incorporated herein by reference in its entirety.

FIELD OF THE INVENTION

The present invention relates to methods and compositions for the modulation of body mass (i.e., weight). More specifically, the present invention relates to the utilization of leptin-like peptides for novel diagnostic and therapeutic implications in homeostasis of body weight and adipose tissue mass.

BACKGROUND OF THE INVENTION

Obesity, defined as an excess of body fat relative to lean body mass, is associated with numerous, important clinical and psychological morbidities, the former includes, but is not limited to: hypertension, elevated blood lipids, and Type II or non-insulin-dependent diabetes mellitus (NIDDM), and decreased life expectancy. The presence and degree of obesity are usually determined by reference to the absolute weight of an individual when compared to age and height matched ideals, or by reference to the individual's body mass index, that is, body weight (in kilograms) divided by height (in meters), compared with age matched ranges. There are approximately 6–10 million individuals with NIDDM in the United States, including 18% of the total population over 65 years of age (see, e.g., Harris, et al., 1987. *Int J Obes* 11: 275–283). In addition, approximately 45% of males and 70% of females with NIDDM are obese, and their diabetes is substantially improved or even eliminated by weight reduction (see, e.g., Harris, 1991. *Diabetes Care* 14: 639–648). Both obesity and NIDDM are strongly heritable, though few of the predisposing genes have been identified. Hence, the molecular genetic basis of these metabolically related disorders is an important, poorly understood problem.

The assimilation, storage, and utilization of nutrient energy constitute a complex homeostatic system central to survival of metazoa. Among land-dwelling mammals, storage in adipose tissue of large quantities of metabolic fuel in the form of triglycerides is crucial for surviving periods of food deprivation. The need to maintain a fixed level of energy stores without continual alterations in the size and shape of the organism requires the achievement of a balance between energy intake and expenditure. However, the molecular mechanisms that regulate energy balance remain to be elucidated. The isolation of molecules that transduce nutritional information and control energy balance will be critical to an understanding of the regulation of body weight in health and disease.

Examination of the concordance rates of body weight and adiposity amongst mono- and dizygous twins or adoptees and their biological parents have suggested that the heritability of obesity (0.4–0.8) exceeds that of many other traits commonly thought to have a substantial genetic component, such as schizophrenia, alcoholism, and atherosclerosis (see e.g., Stunkard, et al., 1990. *N Engl J Med* 322: 1483–1487). Familial similarities in rates of energy expenditure have also been reported (see e. g., Bogardus, et al., 1986. *Diabetes* 35: 1–5). Genetic analysis in geographically delimited populations has suggested that a relatively small number of genes may account for the 30–50% of variance in body composition (see e.g., Moll, et al., 1991. *Am. J Hum. Genet* 49: 1243–1255).

A major advance in understanding the molecular basis for obesity occurred with the cloning of the ob gene. The mouse obesity (ob) gene encodes an adipose tissue-derived signaling factor for body weight homeostasis. The mouse ob gene encodes a 4.5-kilobase adipose tissue mRNA (see, e.g., Montague, et al., 1997. *Nature* 387: 903–908) with a widely conserved 167-amino acid open reading flame and a 21-amino acid secretory signal sequence. The predicted amino acid sequence of the protein product of this gene, leptin (from the Greek leptos, meaning thin), is 84% identical in humans and mice and has features of a secreted protein (see, e.g., Zhang, et al., 1994. *Nature* 372: 425). Several recent studies have shown that recombinant ob protein purified from *Escherichia coli* can correct the obesity related phenotypes in ob/ob mice when exogenously administered (see e.g., Campfield, et al., 1995 *Science* 269: 546; Pellymounter, et al., 1995. *Science* 269: 540; Stephens, et al., 1995. *Nature* 377: 530). Weight-reducing effects of recombinant leptin were also observed in normal mice and mice with diet-induced obesity.

Interestingly, recent studies have suggested that obese humans and rodents (other than ob/ob mice) are not defective in their ability to produce leptin mRNA or protein and generally produce higher levels than lean individuals (see e.g., Maffei, et al., 1995. *Nature Med* 1: 1155; Considine, 1995. *J. Clin. Invest.* 95: 2986; Hamilton, et al., 1995. *Nature Med.* 1: 953). This data suggest that resistance to normal or elevated levels of leptin may be important factors in human obesity.

Leptin is a 16 kDa hormone that is the afferent signal in a negative feedback loop regulating food intake and body weight. The leptin receptor is a member of the cytokine receptor family. Leptin's anorexigenic effect is dependent on binding to the Ob-$R_b$ isoform of this receptor which encodes a long intracytoplasmic domain that includes several motifs for protein-protein interaction. Ob-$R_b$ is highly expressed in the hypothalamus suggesting that this brain region is an important site of leptin action. Signal transduction by this class of receptor generally depends on ligand-induced phosphorylation of soluble tyrosine receptor kinases such as Janus kinase (JAK)-1, -2, -3, and tyk2. These kinases, in turn, phosphorylate tyrosine residues on the receptor which serve as docking sites for SH2 proteins. Phosphorylation of SH2 proteins, following receptor-binding, initiates signal transduction. Leptin binds to a homodimer ajar of the Ob-$R_b$ isoform of its receptor, thus activating JAK2. While Stat3-regulated transcription is activated by leptin in viva, the identity of other components of this signal transduction pathway have not yet been quantitatively identified.

In recent studies, mutation of the mouse ob gene has been demonstrated to result in a syndrome that exhibits pathophysiology which includes: obesity, increased body fat deposition, hyperglycemia, hyperinsulinemia, hypothermia, and impaired thyroid and reproductive functions in both male and female homozygous ob/ob obese mice (see e.g., Ingalis, et al., 1950. *J Hered* 41: 317–318). As previously discussed, recent studies have suggested that obese humans and rodents (other than ob/ob mice) are not defective in their ability to produce leptin mRNA or protein and generally produce higher levels than lean individuals. Two distinct mutations of this gene have been identified. One mutant, designated SM/Ckc-+$^{Dac}$ob$^{2J}$/ob$^{2J}$, expresses no leptin mRNA (see, e.g., Lonnqvist, 1996. *Q. J. Med.* 89: 327–332); whereas the other mutation, designated C57BL/6J, overexpresses by 20-fold a mRNA species resulting from a single-base mutation in the ob gene at codon 105. This mutation changes the coding sequence for arginine (Arg)-105 in leptin to a premature stop codon, and causes production of a truncated inactive form of leptin (see, e.g., Zhang, et al., 1994. *Nature* 372: 425).

The mouse ob gene (GenBank Accession No. U2242 1) and its human homolog (GenBank Accession No.NM_000230) have been cloned (see, e.g., Zhang, et al., 1994. *Nature* 372: 425–432). The protein product of this gene, leptin, which has been postulated to act as a blood-borne hormone responsible for weight maintenance, is a 16-kDa plasma protein synthesized and secreted by adipocytes (see e.g., Halaas, et al., 1995. *Science* 269: 543–546; Pelleymounter, et al., 1995. *Science* 269: 540–543; Weigle, et al., 1995. *J. Clin. Invest.* 96: 2065–2070). The ob/ob mouse phenotype has been attributed to a deficiency in active leptin. A number of laboratories have reported that administration of recombinant leptin to C57BL/6J ob/ob mice, normal lean, or diet-induced obese mice resulted in weight loss through reduced food intake and increased energy expenditure (see e.g., Weigle, et al., 1995. *J Clin Invest* 96: 2065–2070; Barash, et al., 1996. *Endocrinology* 137: 3144–3147). Use of leptin or leptin receptor have been proposed as novel therapeutics in the treatment of human obesity. See, e.g., PCT Patent Applications WO 97/26335, WO 98/06752 and WO 99/23493. Other uses for leptin or leptin receptor include (i) diabetes (see, e.g., PCT Patent Applications WO98155139, WO98/12224, and WO97/02004); (ii) hematopoiesis (see, e.g., PCT Patent Applications WO97/27286 and WO98118486); (iii) infertility (see, e.g., PCT Patent Applications WO97/15322 and WO98/36763); and (iv) tumor suppression (see, e.g., PCT Patent Applications WO98/48831), each of which are incorporated herein by reference in their entirety.

Leptin fragments, and most particularly an 18 amino acid fragment comprising residues $^{57}$VTGLDFIPGLH-PILTLSK$^{74}$ taken from full length human leptin [the full length sequence is shown in SEQ ID NO:17], have been reported to function in weight loss, but only upon direct administration through an implanted cannula to the lateral brain ventricle of rats. See, e.g., PCT Patent Applications WO97/46585, which is incorporated herein by reference in its entirety. Those fragments in PCT Patent Applications WO97/46585 are different from the fragments of this invention.

To date, most leptin-related studies able to report weight loss activity from administration of recombinant leptin, leptin fragments and/or leptin receptor variant have administered said constructs directly into the ventricles of the brain. See e.g., Weigle, et al., 1995. *J Clin Invest* 96: 2065–2070; Barash, et al., 1996. *Endocrinology* 137: 3144–3147. Administration of any treatment directly into the brain has serious drawbacks for widespread use of such treatment in the human population. Only studies by the inventors have been able to show significant weight loss activity due to administered of leptin peptides by more favorable methods, namely, through intraperitoneally (i.p.) administration, to test subjects. See, Grasso et al., 1997. *Endocrinology* 138: 1413–1418.

High-affinity leptin binding sites have been identified in mouse choroid plexus, the leptin receptor (OB-R) gene has been cloned (GenBank Accession No.AF098792), and genetic mapping has localized this gene in the same interval of mouse chromosome 4 that contains the db locus (see, e.g., Tartaglia, et al., 1995. *Cell* 83: 1263–1271). Several transcripts of the OB-R, resulting from alternative splicing, have also been identified. Defects in OB-R produce a syndrome in the mutant diabetic db/db mouse that is phenotypically identical to the ob/ob mouse (see, e.g., Ghilardi, et al., 1996. *Proc. Natl. Acad. Sci.* USA 93:6231–6235). In contrast to ob/ob mice, however, administration of recombinant leptin to C57BLKS/J-m db/db mice does not result in reduced food intake and body weight (see, e.g., Roberts and Greengerg, 1996. *Nutrition Rev.* 54: 41–49). Expression of murine leptin receptors has also been detected at high levels in non-neural tissues including the lung, kidney and ovary (see, e.g., Meier, 1996. *Eur. J. Endocrinol.* 134: 543–545; Chehab, et al., 1996. *Nature Genet* 12: 318–320). In adult humans, highest expression of OB-R is in heart, liver, small intestine, prostate and ovary, whereas lung and kidney express it at low levels (see, e.g., Cioffi, et al., 1996. *Nature Med.* 2: 585–589).

Expression of the ob gene in humans is highly correlated with body fat and body mass index, with greater expression observed in obese than in normal-weight individuals (see, e.g., Considine, et al., 1996. *N. Engl. J. Med.* 334: 292–295). A similar correlation between serum leptin concentrations and ob mRNA levels in adipose tissue of obese individuals has also been found (see, e.g., Maffei, et al., 1995. *Nature Med.* 1: 1155–1161). Because leptin concentrations are high in the serum of most obese humans, but decrease with weight loss, human obesity is believed to result from leptin resistance (see, e.g., Lonnqvist, et al., 1995. *Nat. Med.* 1: 950–953; Misra and Garg, 1996. *J. Invest. Med.* 44: 540–548). Furthermore, since obese humans do not have elevated cerebrospinal fluid levels of leptin, even though their plasma concentrations may be five-fold higher than nonobese individuals, the rate-limiting factor contributing to leptin resistance in obese humans appears to be related to defective leptin transport into the CNS (see, e.g., Banks, et al., 1996. *Peptides* 17: 305–311; Caro, et al., 1996. *Lancet* 348:159–161).

In humans, the ob gene is expressed almost exclusively in adipose tissue, and codes for a protein that is 84% homologous to mouse leptin (see, e.g., Considine, et al., 1995. *J. Clin. Invest.* 95: 2986–2988; Masuzaki, et al., 1995. *Diabetes* 44: 855–858). Recently, however, placental sources of leptin have been identified (see, e.g., Masuzaki, et al., 1997. *Nat. Med.* 3: 1029–1022; Senaris, et al., 1997. *Endocrinology* 138: 501–502). Although the ob gene and the OB receptor gene (db) are normal in most cases of human obesity, a frameshift mutation (see, e.g., Montague, et al., 1998. *Int. J. Obes.* 22: 200–205), and polymorphism in the 5' non-translated region of the human ob gene (see, e.g., Considine, et al., 1996. *Biochem, Biophys. Res. Commun.* 220: 735–739; Hager, et al., 1998. *Int. J. Obes.* 22: 200–205) in a number of morbidly obese humans with low serum leptin concentrations have been reported. Possible linkage of extreme obesity to markers flanking the human ob gene, has also been proposed (see, e.g., Clement, et al., 1996. *Diabetes* 45: 687–690; Reed, et al., 1996. *Diabetes* 45: 691–694). These aforementioned recent findings suggest that administration of recombinant leptin, or leptin mimetics of even higher potency than leptin, may be possible approaches to the treatment of at least some forms of human obesity.

There is some evidence that leptin enters the brain via a saturable transport system. See, e.g., Banks et al., 1996, *Peptides*, 17: 305–311. Because the majority of obese humans do not have elevated cerebrospinal fluid (CSF) levels of leptin, even though their plasma levels may be five-fold higher when compared to nonobese individuals, the rate-limiting factor associated with leptin resistance in human obesity may be related to defective leptin transport into the central nervous system (CNS). See, e.g., Caro et al., 1996. *Lancet* 348: 159–161; Schwartz et al., 1996. *Nat Med* 2: 589–593. The ability of centrally administered leptin to reduce food intake and body weight gain in diet-induced obese mice resistant to peripherally administered leptin, is consistent with a mechanism of obesity which may involve saturated or defective leptin transport. See, e.g., Van Heek et al., 1997. *J Clin Invest* 99: 385–390.

In this regard, the mature form of circulating leptin is a 146-amino acid protein that is normally excluded from the CNS by the blood-brain barrier (BBB) and the blood-CSF barrier. See, e.g., Weigle et al., 1995. *J Clin Invest* 96: 2065–2070. Thus, efforts to develop leptin-related peptide agonists of low molecular weight, or nonpeptide mimetics that can be transported across the BBB and blood-CSF barrier by mechanisms independent from those by which leptin is transported take on added importance. Identification of active epitopes within the leptin molecule, therefore, is important to the development of leptin analogs which can be administered peripherally, and thus have potential usefulness in the treatment of human obesity and its related dysfunctions.

In addition, there is a current need for methods and related compositions that could be utilized in detecting physiological obesity or other conditions related to abnormalities of the endogenous leptin pathway. Accordingly, given the aforementioned observations, there remains an as yet unfulfilled need for the development of low molecular weight, highly-potent peptide agonists of leptin, or nonpeptide leptin mimetics which are permeable to the Blood-Brain Barrier and can thus enter the central nervous system (CNS) without assisted-transport. The development of such pharmacophores may ultimately lead to novel methods of treatment for physiological obesity and/or other conditions which are related to abnormalities of endogenous leptin pathway, as well as a possible extension of their application to other obesity-related dysfunctions (e.g., Type II or non-insulin-dependent diabetes mellitus (NIDDM)).

The citation of any reference herein should not be deemed as an admission that such reference is available as prior art to the instant invention.

SUMMARY OF THE INVENTION

Numerous, prior clinical trials which have attempted to treat obese individuals with recombinant leptin have met with markedly limited success. Typical serum leptin concentrations in most obese humans are elevated above those of non-obese individuals by as much as 5-fold. However, the cerebral spinal fluid (CSF) of these obese individuals often have normal leptin levels, thus suggesting that the rate-limiting factor contributing to leptin resistance in these individuals may be related to defective transport of leptin through the Blood-Brain Barrier and into the Central Nervous System (CNS).

Disclosed herein is a low molecular weight leptin-related peptide comprising the C-terminal amino acid residues 116–122 of native leptin (LEP) [the full length mouse and human leptin proteins are depicted in SEQ ID NOS:1 and 17, respectively], wherein the LEP(116–122) peptide is herefrom referred to as "OB-3" [SEQ ID NO:2 and 18 depicting mouse and human OB-3, respectively, and fragments, derivatives, analogs and homologs thereof]. OB-3 possesses the ability to modulate body mass homeostasis in test animals upon i.p. (intraperitoneal) administration. It is contemplated that OB-3 can enter the CNS without assisted-transport. In addition, OB-3 is able to both reduce weight gain as well as reduce food intake in test animals. Also disclosed are leptin-related peptides comprising N-terminal amino acids 21–35, 31–45, 41–55 and 51–65 of native leptin, and herefrom referred to as LEP(21–35) [SEQ ID NO:3], LEP(31–45) [SEQ ID NO:4], LEP(41–55) [SEQ ID NO:5] and LEP(51–65) [SEQ ID NO:6], respectively, and fragments, derivatives, analogs and homologs thereof. Additional peptides of the invention comprise LEP(61–75) [SEQ ID NO:7], LEP(71–85) [SEQ ID NO:8], LEP(81–95) [SEQ ID NO:9], LEP(91–105) [SEQ ID NO:10], LEP (106–120) [SEQ ID NO:11], LEP(116–130) [SEQ ID NO:12], LEP(126–140) [SEQ ID NO:13], LEP(136–150) [SEQ ID NO:14], LEP(146–160) [SEQ ID NO:15], and LEP(156–167) [SEQ ID NO:16]. We prefer the peptides of SEQ ID NOS: 2–10 and 18. See, e.g., FIG. 1 and FIG. 16 for mouse and human full length protein, respectively. In addition, the OB-3 and OB-3-related peptides of the present invention [SEQ ID NOS:2–16 and 18], and fragments, derivatives, analogs and homologs thereof, are exceptionally strong candidates for the development of leptin-related analogs, or mimetics, with potential application to the treatment of human obesity, a general syndrome which is characterized by pathophysiology including, but not limited to, hyperglycemia, hyperinsulinemia, hyperphagia, thyroid dysfunction and infertility, and may have potential extension of their application to other obesity-related dysfunctions (e.g., Type II or non-insulin-dependent diabetes mellitus (NIDDM)). Peptides provided in the invention may be synthesized via a protein synthesizer or, alternatively, may be encoded by recombinant nucleic acids, inserted into recombinant tissue culture cells or test animals, and expressed therefrom. Recombinant nucleic acids encoding OB-3 or OB-3-related peptides of the present invention are also provided. All forms of OB-3 and OB-3-related peptides of the present invention, and fragments, derivatives, analogs and homologs thereof, may be derived from recombinant cells containing nucleic acids encoding OB-3 and OB-3-related peptides of the present invention, and fragments, derivatives, analogs and homologs thereof, and are, preferably, a mammalian form of leptin. Alternatively, all forms of OB-3 and OB-3-related peptides of the present invention, and fragments, derivatives, analogs and homologs thereof, may be derived from chemical synthesis. In a more preferred embodiment, the OB-3 and OB-3-related peptides, and fragments, derivatives, analogs and homologs thereof, are a murine form of leptin (GenBank Accession No. U22421), and in the most preferred embodiment, these peptides are a human form of leptin (GenBank Accession No. NM_000230).

In a specific embodiment of the present invention, a synthetic OB-3 or OB-3-related peptide is utilized in the regulation of adiposity and fat content of a mammal, most preferably a human. The effectiveness of various OB-3 or OB-3-related peptides of the present invention in the treatment of leptin-resistant db/db mice (i.e., an animal model closely resembling human obesity), indicates that these peptides are not acting at the level of the leptin receptor. Accordingly, this novel observation raises the possibility that our OB-3 or OB-3-related peptides may have therapeutic applications in clinical situations where treatment with recombinant leptin has been found to be ineffective. Although the mechanism of action of our peptides appears to differ from that of leptin, their inhibitory effects on food intake and body weight gain in obese female C57BL/6J ob/ob mice are clear. The observed ability of the OB-3 or OB-3-related peptides of the present invention to correct the energy imbalance responsible for the obese phenotype in this aforementioned animal model suggests that they may be valuable lead compounds in efforts to develop leptin agonists of even higher potency than leptin.

The present invention is also directed to therapeutic compositions which are useful for either the diagnosis or treatment of abnormalities within the endogenous leptin pathway, such as physiological obesity. The OB-3 or OB-3-related peptides of the present invention may be utilized alone, or in combination with the wild-type leptin protein, in compositions for use in medically-assisting mammalian subjects who possess abnormalities in the regulatory control of their body weight. Also disclosed are methods for producing the therapeutic composition comprising OB-3 or OB-3-related peptides. In one embodiment, the therapeutic composition is made by adding a suitable amount of one or more OB-3 or OB-3-related peptides to a pharmaceutically-acceptable carrier. In a preferred embodiment, a therapeutic composition comprising synthetic OB-3 or OB-3-related peptide possesses increased bioavailability, as compared to recombinant leptin protein. As it is currently postulated that the target tissues which mediate the effects of leptin are brain tissues, in a most preferred embodiment, the synthetic OB-3 or OB-3-related peptide is able to efficiently traverse the Blood-Brain Barrier for increased bioavailability within the CNS.

The present invention also discloses a therapeutic composition comprising a pharmaceutically-acceptable carrier and an antagonist of the OB-3 or OB-3-related peptide. Such embodiments may serve to inhibit the effect of the OB-3 or OB-3-related peptide, and thus prove useful in the treatment of diseases wherein patients experience an un-healthy, or even life-threatening, decrease in weight, such as is found in anorexias, certain cancers, and AIDS. For example, an antagonist of the OB-3 or OB-3-related peptide may be an antibody that binds to, and subsequently neutralizes the activity of the OB-3 or OB-3-related peptide, or derivative or analog thereof Alternately, the agonist may be a small molecule antagonist of a OB-3 peptide-interacting protein or OB-3-related peptide-interacting protein (IP). In a preferred embodiment, the antagonist does not serve as a mediator in the binding of OB-3 or OB-3-related peptide to an OB-3 peptide-IP or OB-3-related peptide IP.

The present invention also discloses antibodies to OB-3 or OB-3-related peptides. In a specific embodiment, an antibody is specific to OB-3. In a second specific embodiment, an antibody is specific to a fragment, derivative, analog or homolog of OB-3. In a third specific embodiment, an antibody specific for a given epitope will possess an association constant for either free or bound that is below $10^8 M^{-1}$, preferably below $10^7 M^{-1}$, and most preferably below $10^6 M^{-1}$. The antibodies of the present invention may be polyclonal, monoclonal, or chimeric, and include all fragment, derivatives, or analogs thereof which retain the antigen-binding sites. For example, such derivatives may include antibodies which are modified so as to possess a phosphorylation site, a reactive sulfhydryl, or like biochemical modification. All antibodies of the present invention may further comprise a detectable-label (e.g., radioactive, fluorescent, and the like).

The present invention also includes use of OB-3 (and related synthetic peptides disclosed herein) in screening for LEP interacting proteins in a cell culture model system or in a test animal model. In a preferred embodiment, the LEP interacting protein is not the OB receptor encoded by the db gene. In a more preferred embodiment, the cell or animal model is genotypically db/db. In a second more preferred embodiment, the cell or animal model is genotypically ob/ob.

DESCRIPTION OF THE FIGURES

FIG. 1 is a representation of the primary structure of mouse leptin [SEQ ID NO:1], wherein the letters indicate the one-letter designation for amino acid residues, and the lines encompass the amino acid residues of the 14 leptin-related peptides of the invention.

FIG. 16 is a representation of the primary structure of human leptin [SEQ ID NO:17], wherein the letters indicate the one-letter designation for amino acid residues, and residues 116–122 are underlined.

DETAILED DESCRIPTION OF THE INVENTION

Figure 2A:
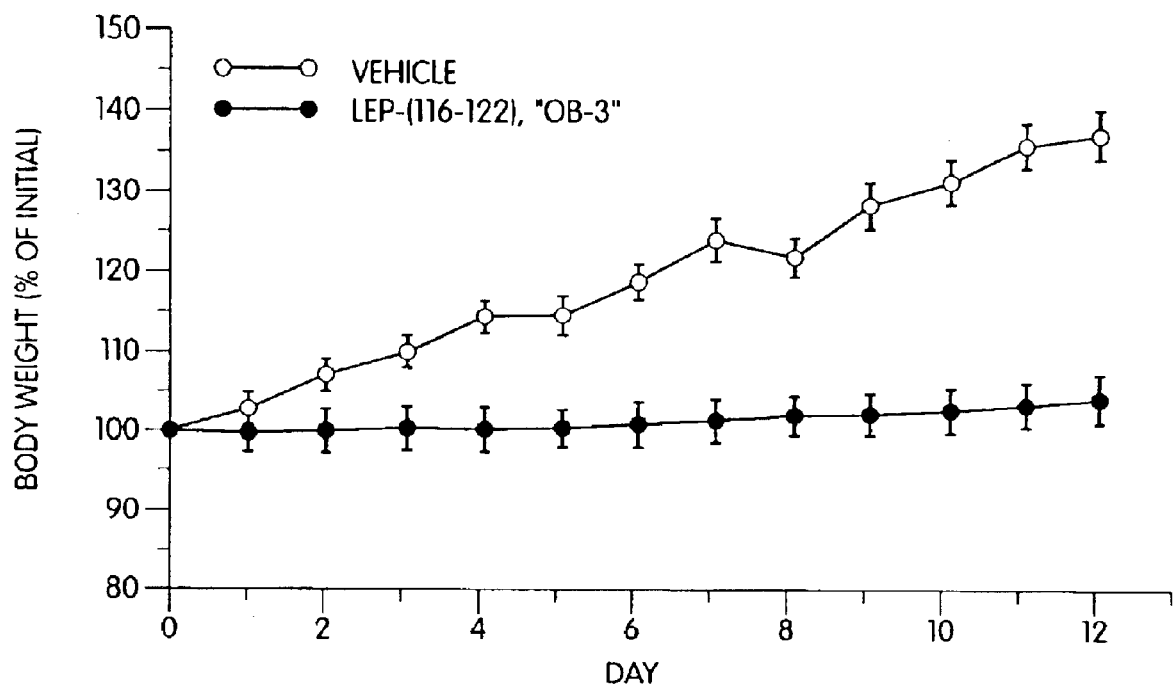
FIGS. 2A–2B are graphic representations of the effects of synthetic leptin peptide OB-3 on body weight gain and food intake in genetically obese female C57BL/6J ob/ob mice.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated herein by reference.

Therefore, if appearing herein, the following terms shall have the definitions set forth below. As used herein, "physiological obesity" and "physiologically obese" refer to excessive adipose tissue that is due at least in part to abnormalities in the endogenous leptin pathway, including abnormalities in the effective signaling initiated by the binding of leptin to the leptin receptor. Abnormalities in the endogenous leptin pathway may be manifested in a number of ways including an abnormal food intake, an abnormal activity level, or an abnormal body temperature. In addition, the present invention allows drugs to be identified which can modulate body mass completely independently of any inherent abnormality in the endogenous leptin pathway per se by augmenting or diminishing the natural effect of leptin.

As used herein, "leptin" encompasses biologically active variants of naturally occurring leptin, as well as biologically active fragments of naturally occurring leptin and variants thereof, and combinations of the preceding. Leptin is the polypeptide product of the ob gene as described in the International Patent Publication No. WO 96/05309, and the U.S. patent application Ser. No. 08/483,211, each of which is incorporated herein by reference in its entirety. Putative analogs and fragments of leptin are reported in U.S. Pat. No. 5,521,283 and U.S. Pat. No. 5,532,336; and International Patent Publication No. PCT/US96/22308 and International Application No. PCT/US96/01471, each of which is incorporated herein by reference in its entirety.

As used herein the terms "bound" or "binds" or "associates" or "associated" are meant to include all such specific interactions that result in two or more molecules showing a preference for one another relative to some third molecule. This includes processes such as covalent, ionic, hydrophobic and hydrogen bonding but does not include non-specific associations such solvent preferences.

As used herein, the phrase "conditions related to abnormalities of the endogenous leptin pathway" encompasses conditions and diseases due, at least in part, to abnormalities involving leptin as detailed above.

The term "medically-assisting" is used herein as a manner of attending to the health care needs of a subject who has a particular problem (e.g., an abnormality in the endogenous leptin its pathway) which encompasses either diagnosing or treating that problem, and all combinations thereof. In one embodiment, the invention provides for medically assisting a mammalian subject suffering from an abnormality in the endogenous leptin pathway resulting in decreased leptin activity. In another embodiment, a mammalian subject may be suffering from an abnormality resulting in increased leptin activity. In each case, the decreased or increased leptin activity may be manifested as a pathological state, such as obesity (decreased leptin activity) or anorexia (increased leptin activity).

As previously discussed, leptin is a 16 kDa hormone that possesses potent weight reducing effects in vivo. Available data indicate that leptin is the afferent signal in a negative feedback loop regulating food intake and body weight. The leptin receptor is a member of the cytokine family. Leptins anorexigenic effect are dependent on binding to the Ob-$R_b$ isoform of its receptor. The Ob-$R_b$ form of this receptor encodes a long intracytoplasmic domain which includes several motifs for protein-protein interaction. The other forms of this receptor have short cytoplasmic regions and are not capable of initiating signal transduction by themselves. Ob-$R_b$ is highly expressed in the hypothalamus suggesting that this region of the brain is an important site of leptin action. A mutation that specifically ablates Ob-$R_b$ expression in mutant diabetic mice results in obesity and complete leptin-resistance. Signal transduction by this class of receptor generally depends on ligand induced phosphorylation of soluble tyrosine receptor kinases such as JAK1, 2, 3, and tyk2. These kinases, in turn, subsequently phosphorylate tyrosine residues on the receptor which serve as docking sites for SH2 proteins. Phosphorylation of SH2 proteins, following receptor-binding, initiates signal transduction.

Due to the fact that the C57BL/6J ob/ob mouse produces only the truncated (i.e., at Arg-105) inactive form of leptin, it was hypothesized that the entire leptin molecule might not be required for the restoration of energy balance. Accordingly, smaller peptides encompassing one or more active sites distal to amino acid residue 105 might thus contain sufficient information to: (i) compensate for an endogenous leptin deficiency; (ii) induce satiety; and (iii) stimulate weight loss in this aforementioned murine model.

In order to examine this possibility, six overlapping peptide amides, which corresponded to amino acid residues 106 to 167 of mouse leptin, were synthesized and their effects on body weight and food intake in female CS7BL/6J ob/ob mice were subsequently assessed. When administered (ip) at 1 mg per day for 28 consecutive days, three of the six peptide amides, designated LEP(106–120), LEP(116–130), and LEP(126–140), comprising amino acid resides 106–120, 116–130, and 126–140 of wild type leptin protein, respectively, significantly (P<0.01) restricted weight gain and food intake when compared to vehicle-injected control mice. Mice given LEP(136–150), LEP(146–160) or LEP (156–167), comprising amino acid resides 136–150, 146–160, and 156–167 of wild type leptin protein, respectively, for 28 days, however, continued to consume food and gain weight at a rate comparable to vehicle-injected control mice (see e.g., Grasso, et al., 1997. Endocrinology 138: 1413–1418).

Intraperitoneal ("ip") administration of synthetic leptin-related peptide "OB-3", comprising amino acid resides 116–122 of wild type leptin protein, reduces food intake and body weight gain in two strains of genetically obese mice: leptin-deficient ob/ob mice and leptin-resistant db/db mice. In one embodiment of the invention, i.p. administration is contemplated and preferred. Synthetic OB-3 represents the amino terminus of the larger peptide LEP(116–130), which we had previously shown to be a functional epitope of mouse leptin, supra (see e.g., Grasso, et al., 1997. Endocrinology 138: 1413–1418).

Figure 2B:
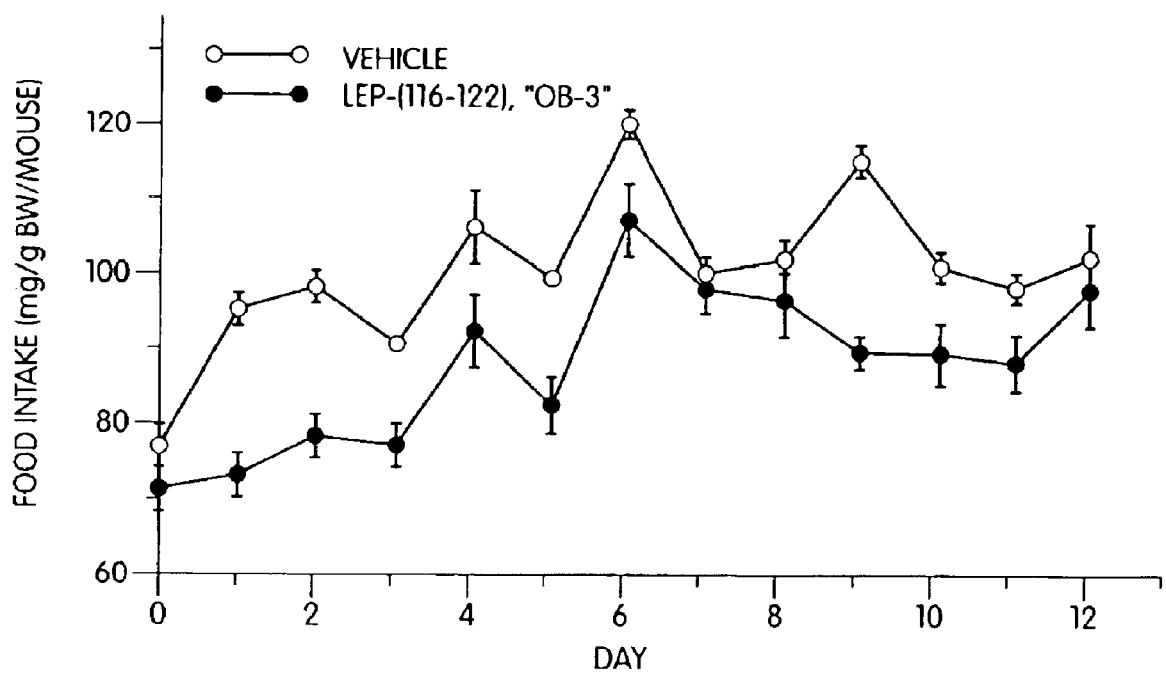
Figure 3A:
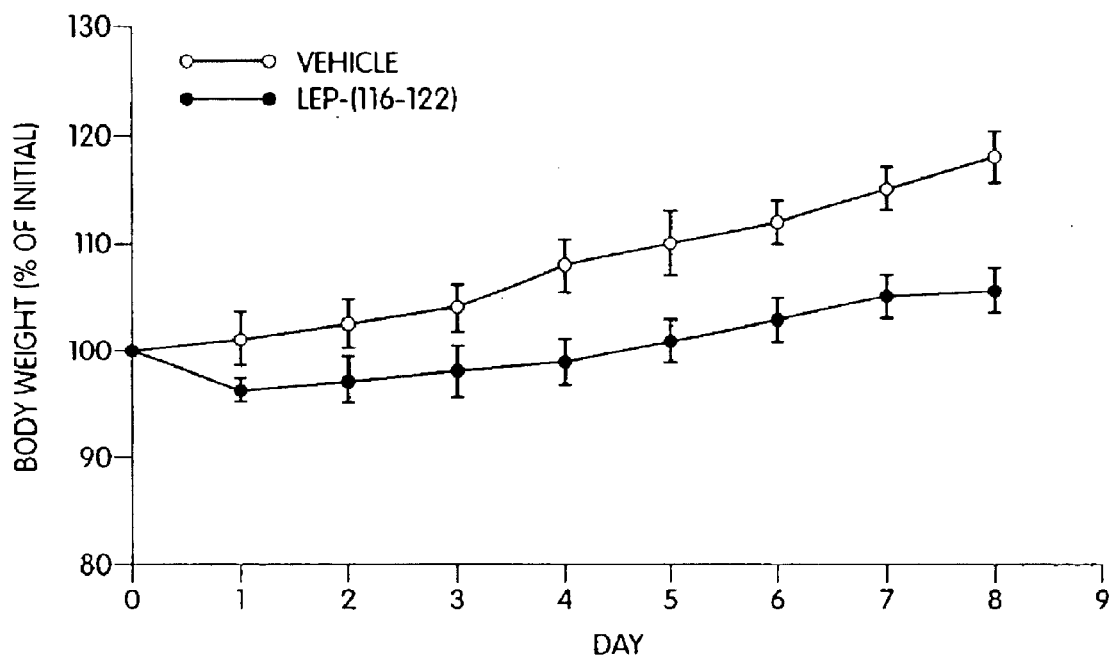
FIGS. 3A–3B are graphic representations of the effects of synthetic, OB-3 on body weight gain and food intake in genetically obese female C57BLKS/J-m db/db mice.
Figure 3B:
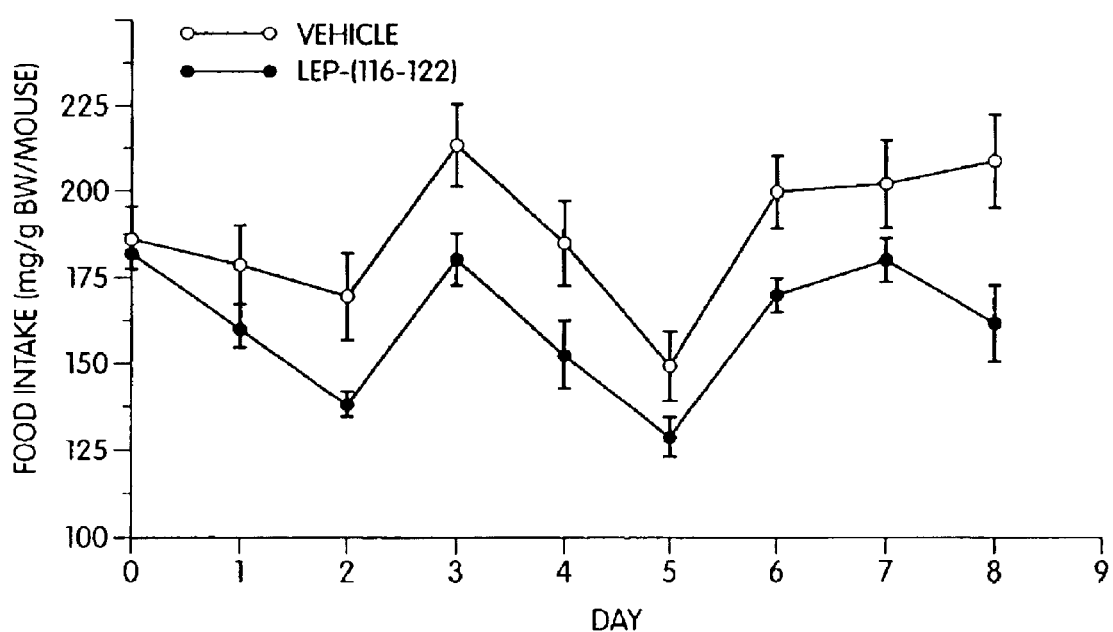
Figure 4A:
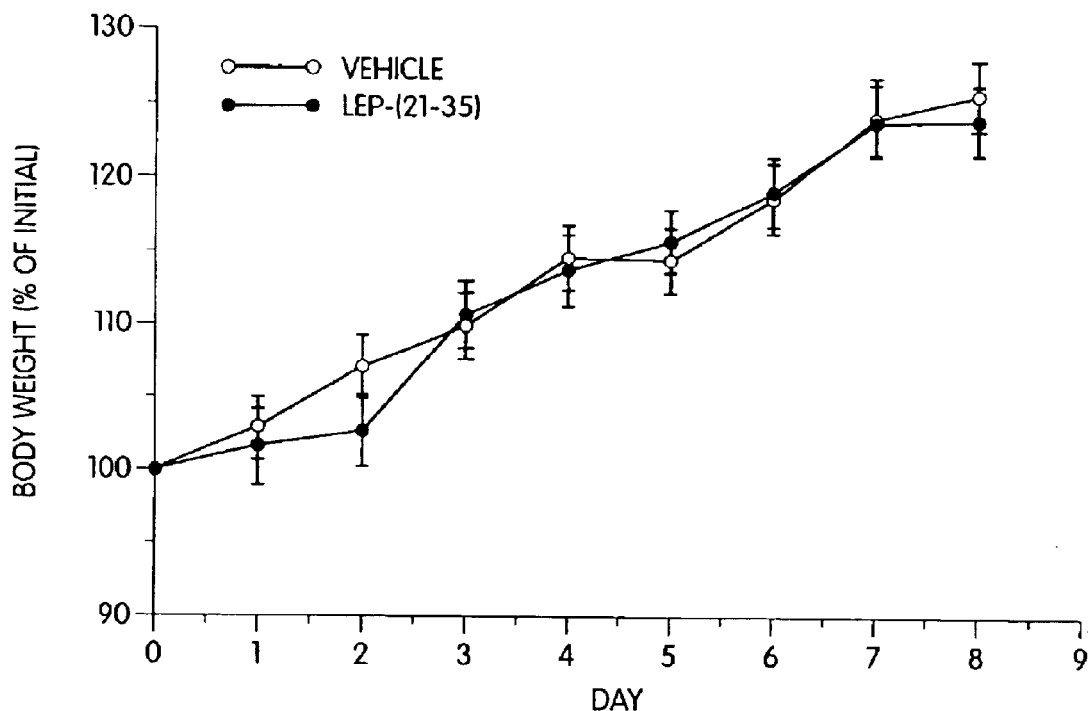
FIGS. 4A–4N are graphic representations of the effects of 7 daily injections of various synthetic leptin peptides on body weight gain in female C57BL/6J ob/ob mice.
Figure 4B:
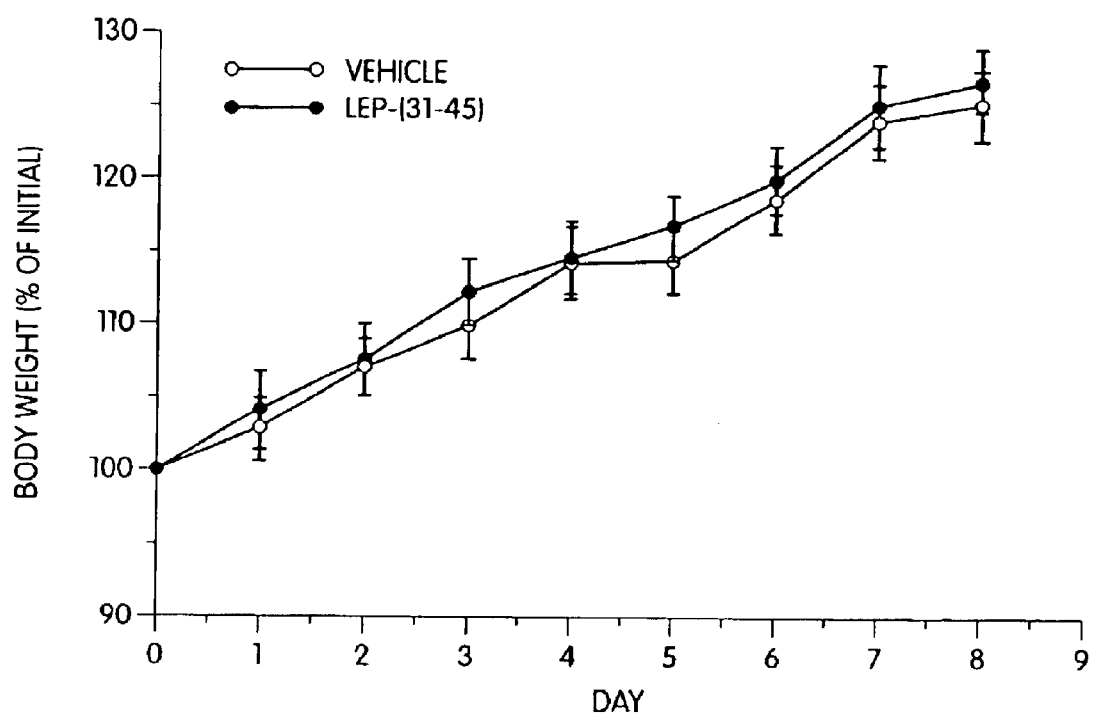
Figure 4C:
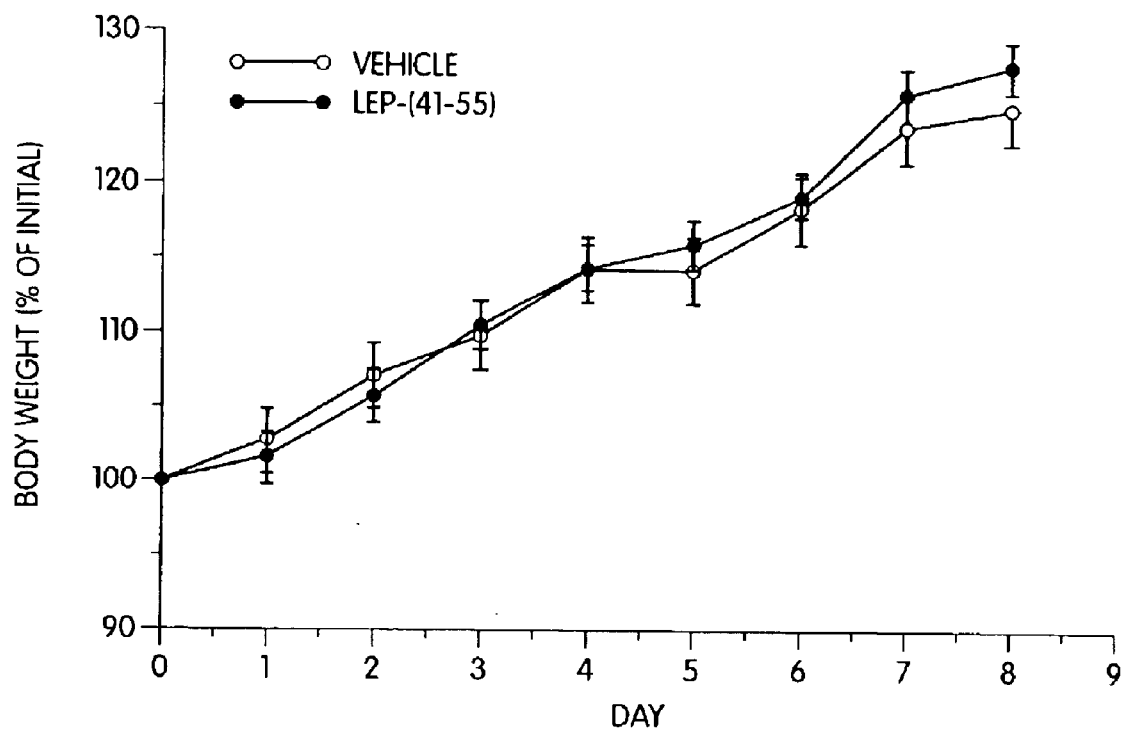
Figure 4D:
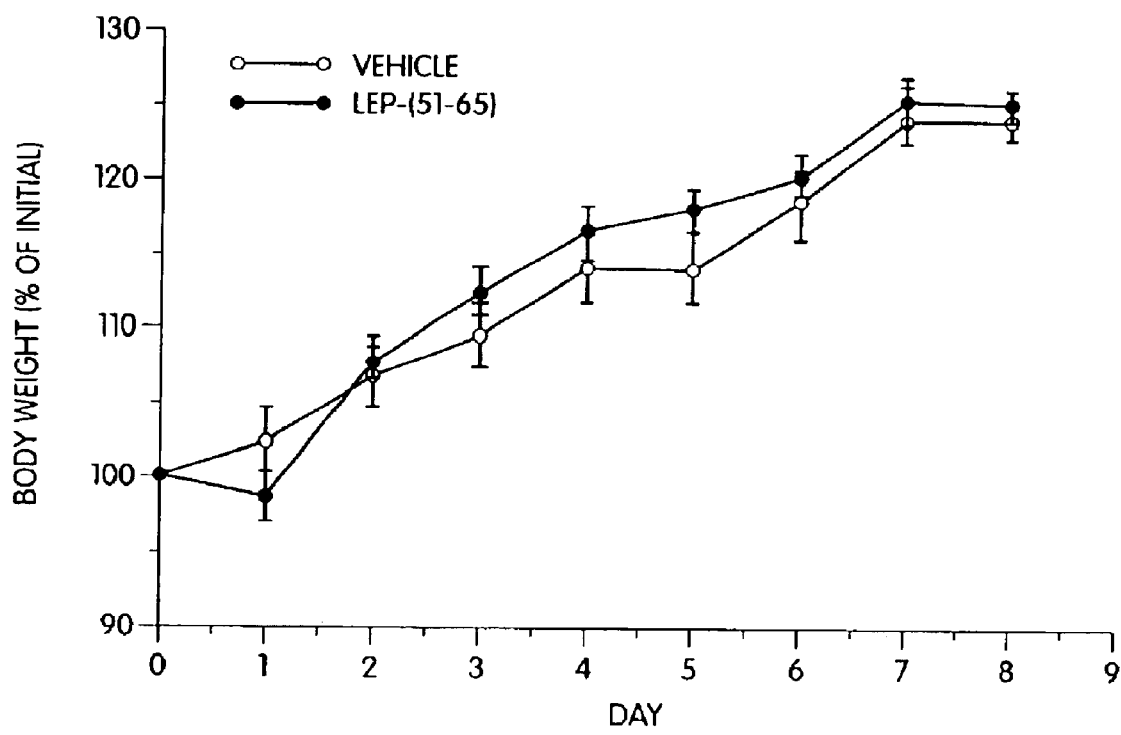
Figure 4E:
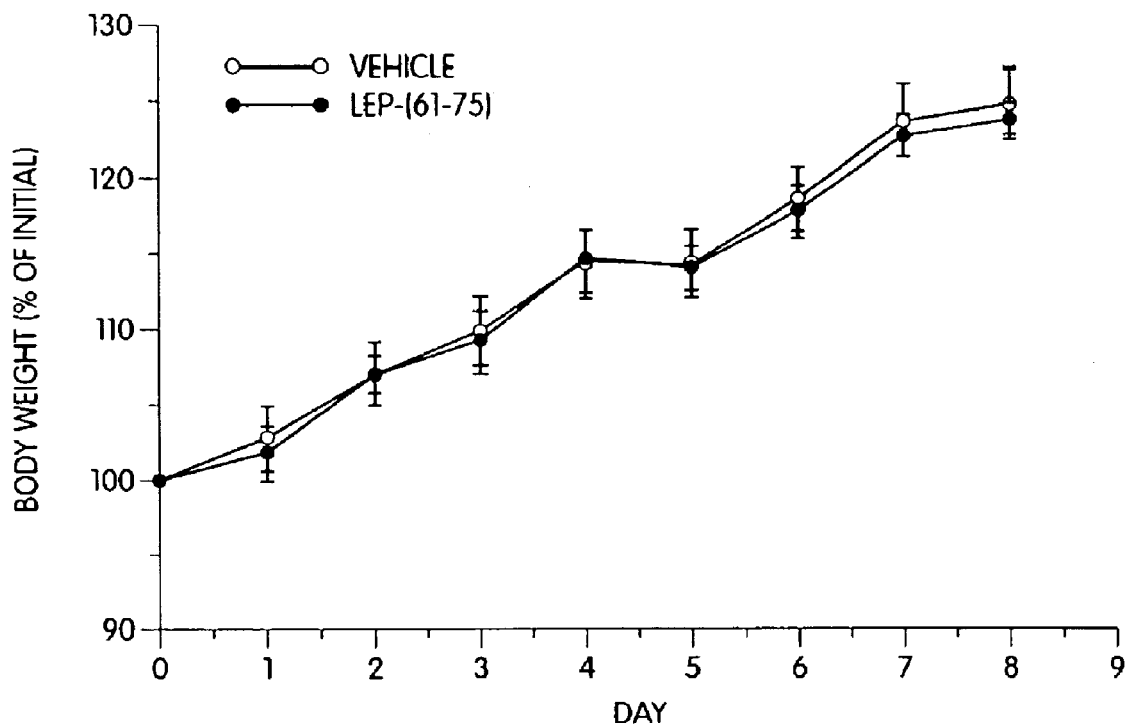
Figure 4F:
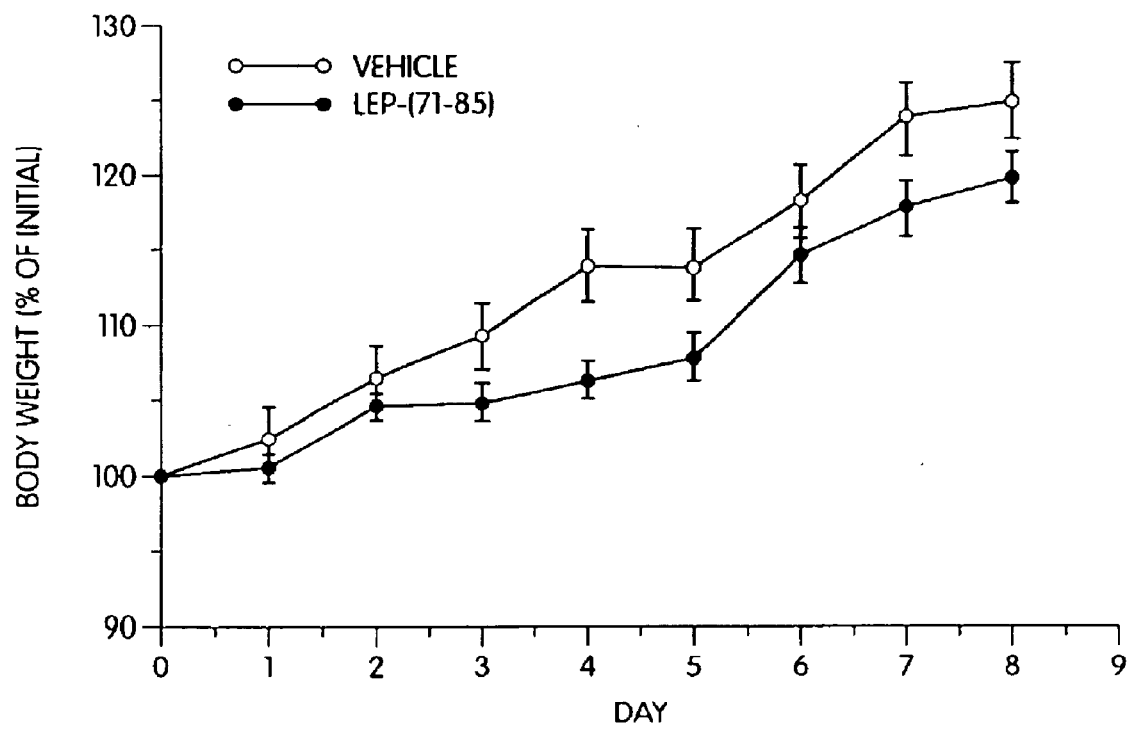
Figure 4G:
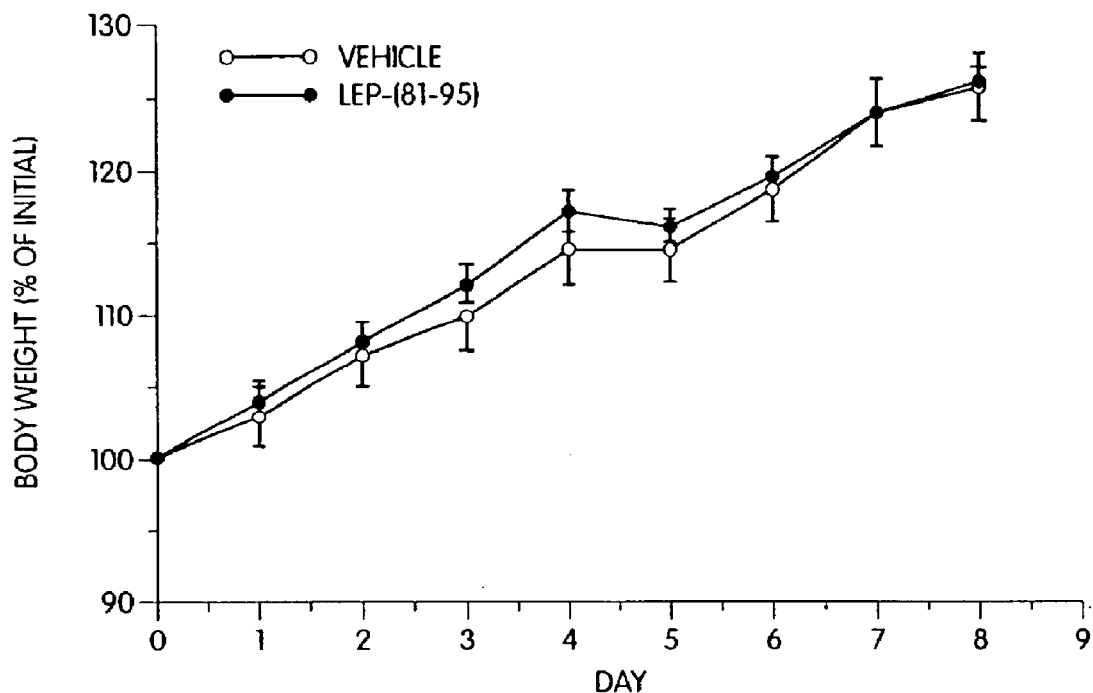
Figure 4H:
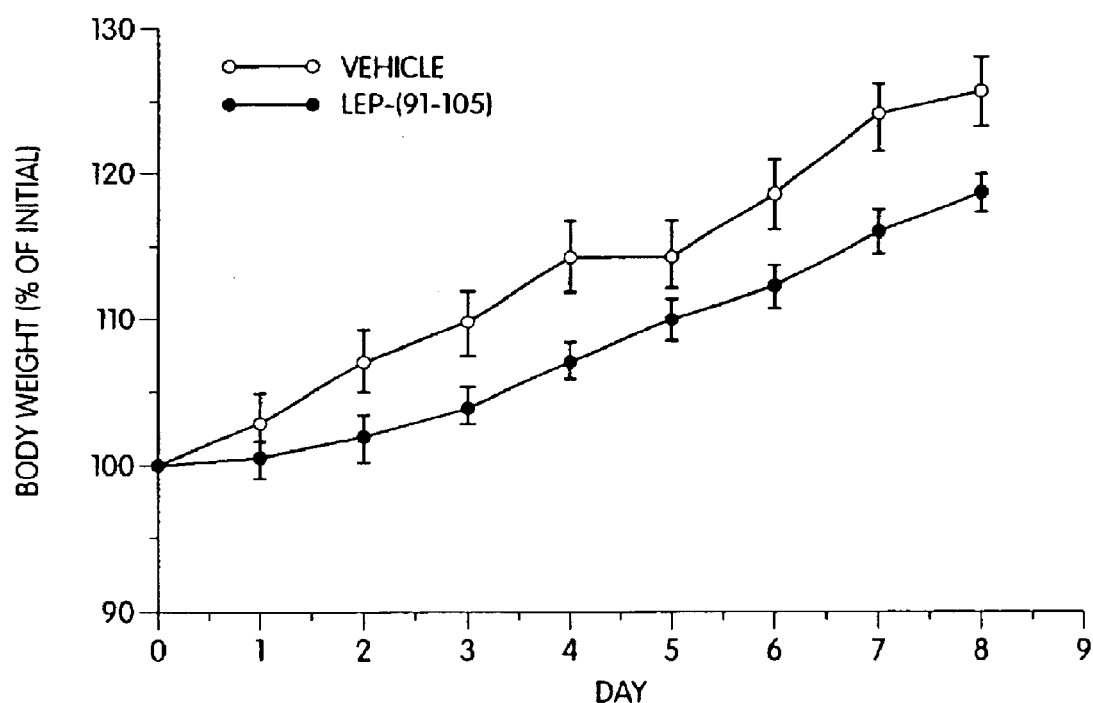
Figure 4I:
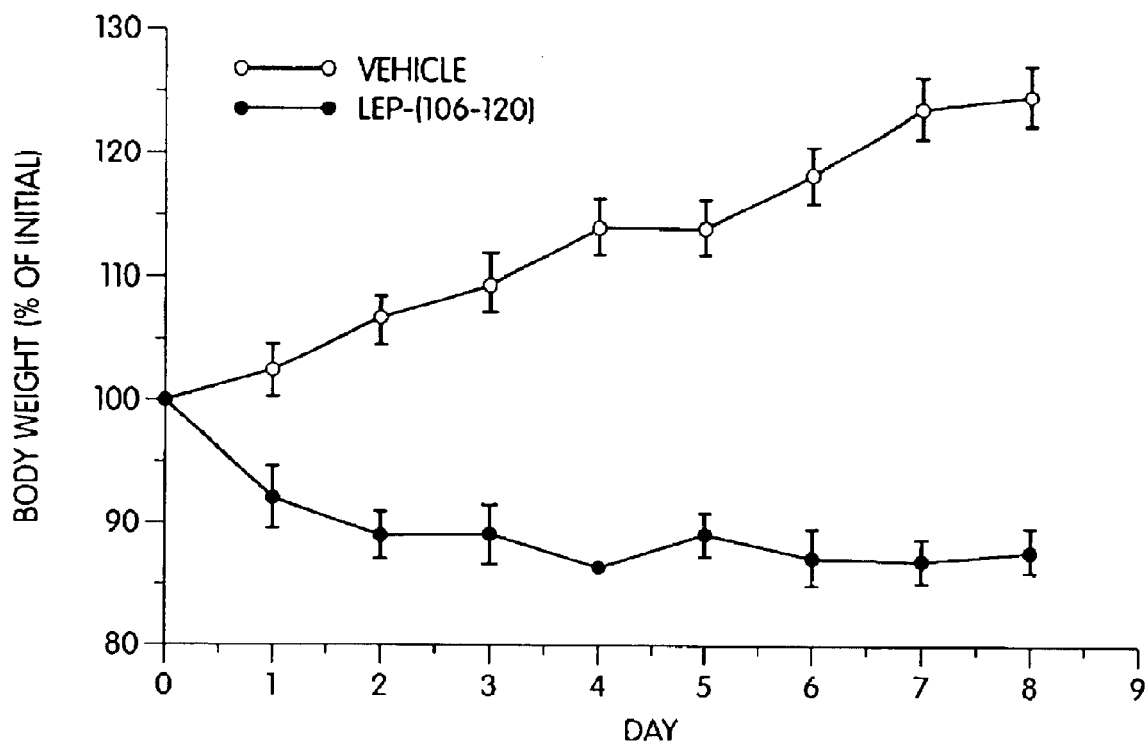
Figure 4J:
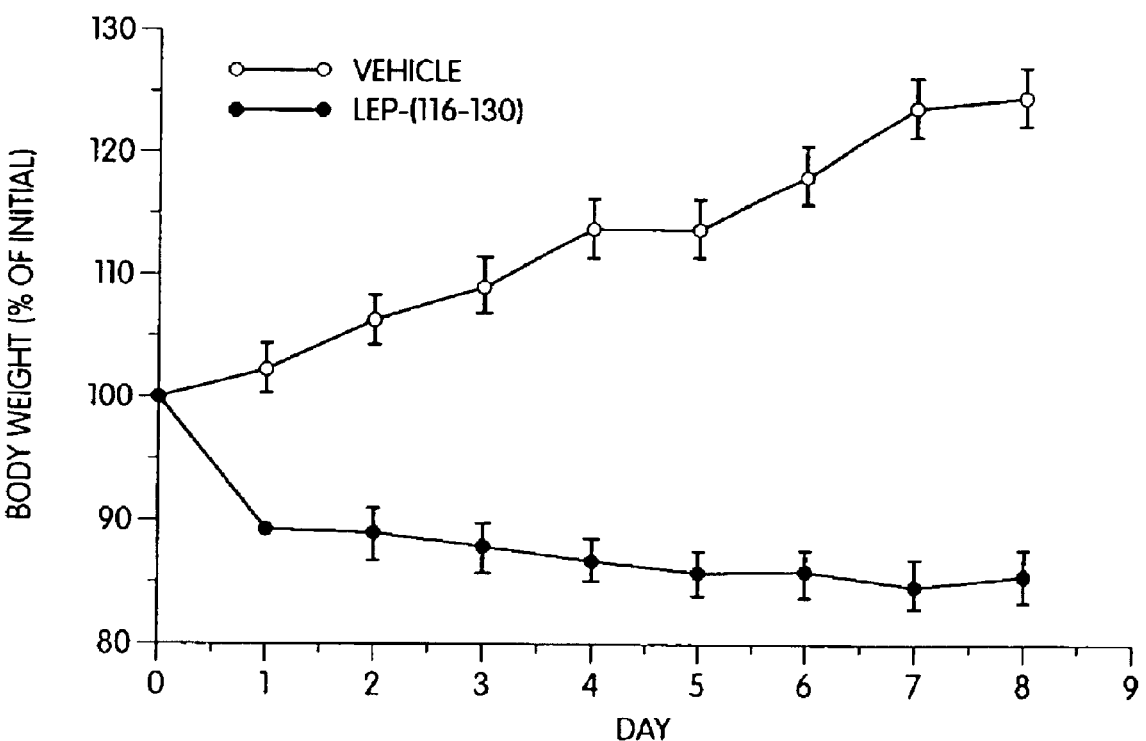
Figure 4K:
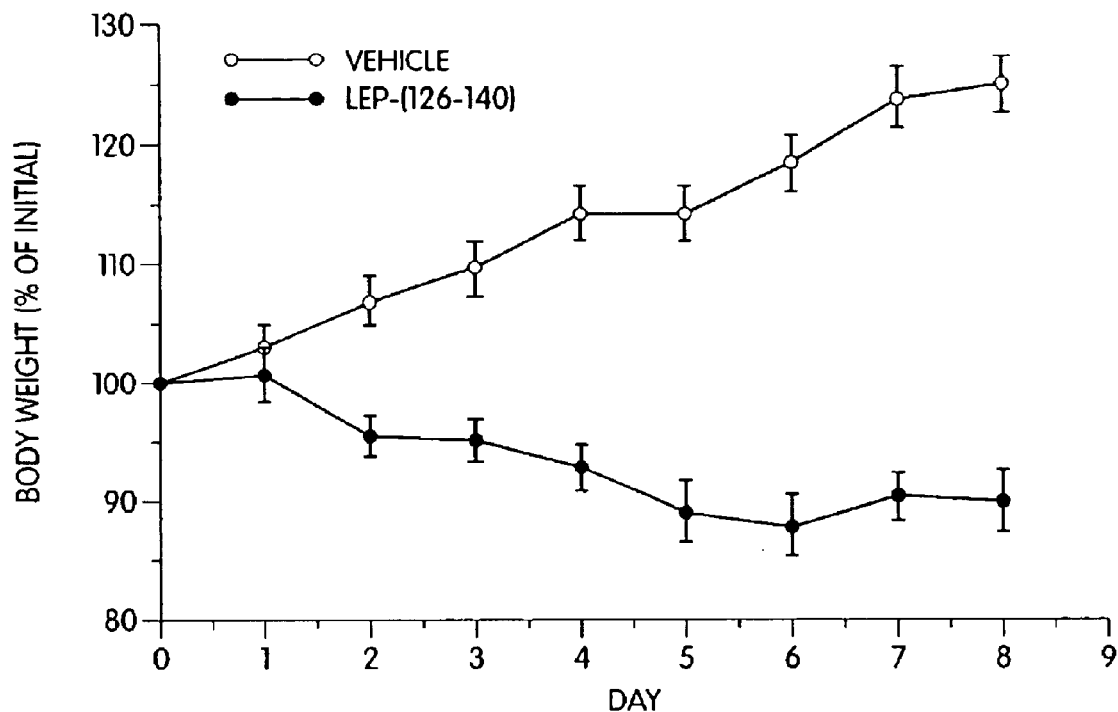
Figure 4L:
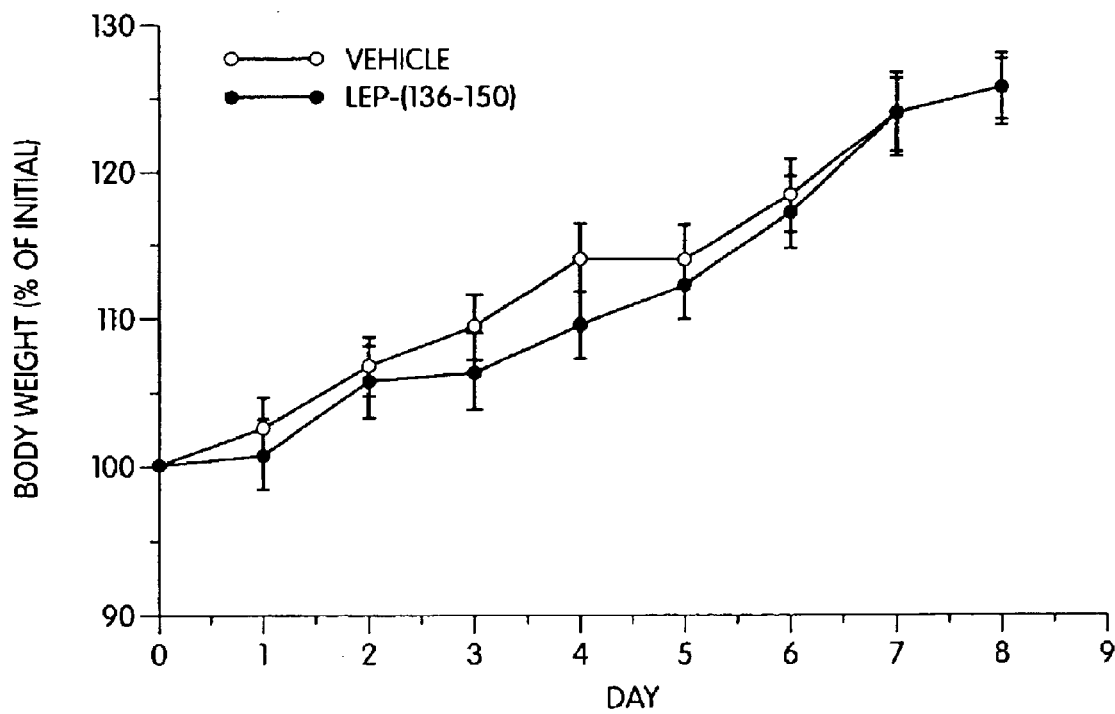
Figure 4M:
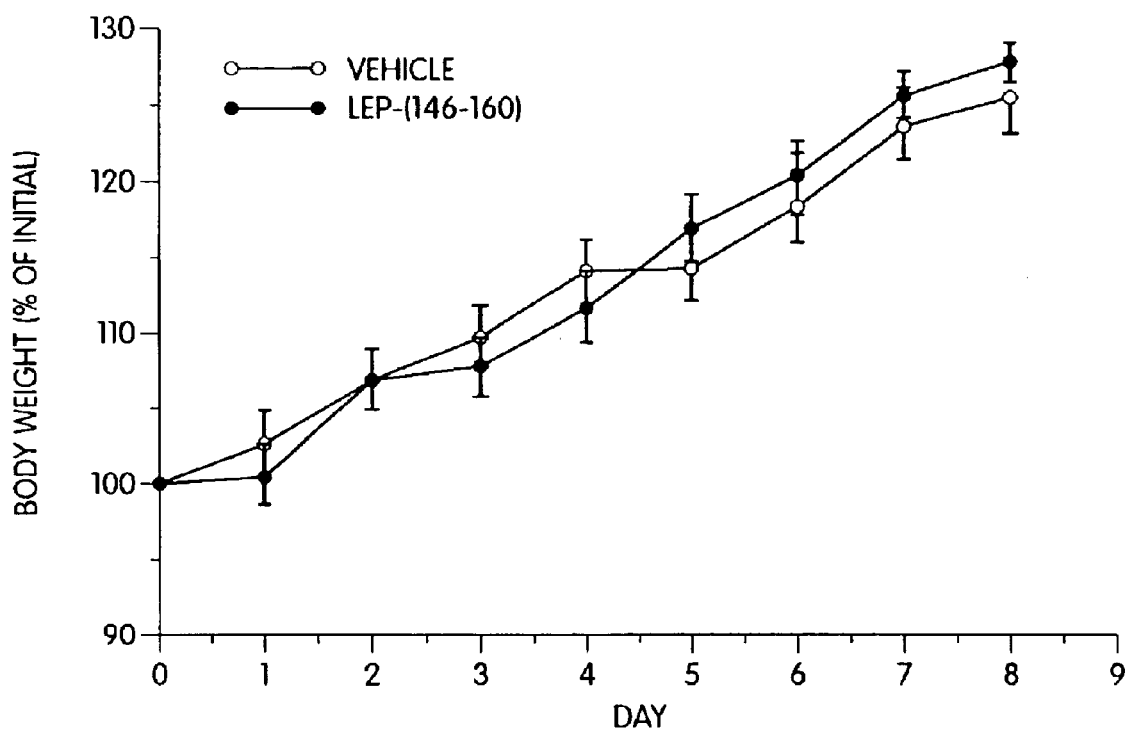
Figure 4N:
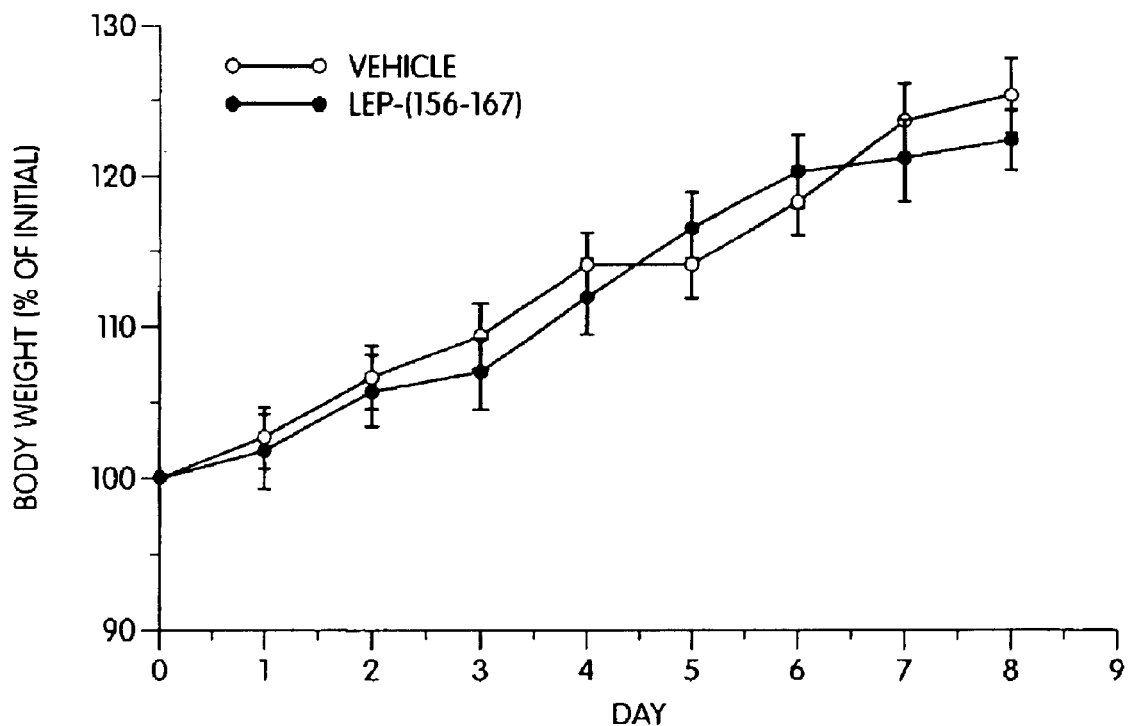

When synthetic OB-3, comprising the amino acid residues 116–122 of leptin protein ($^{116}$Ser-Cys-Ser-Leu-Pro-Gln-Thr$^{122}$), as shown in FIG. 1, is administered to leptin-deficient female obese C57BL/6J ob/ob mice (1 mg/day, ip, 12 days), OB-3 reduced body weight gain and food intake when compared to vehicle-injected control mice (FIG. 2). Similar results were seen in OB-3-treated leptin-resistant female obese C57BLKS/J-m db/db mice, (1 mg/day, ip, 7 days) (FIG. 3).

This discovery of leptin-like activity in synthetic OB-3 in leptin-resistant db/db mice, whose leptin-resistance is due to a mutation in the leptin receptor gene, made this peptide an exceptionally strong candidate for the development of a leptin-related analog or mimetic with is potential application to the treatment of human obesity, a syndrome characterized by hyperglycemia, hyperinsulinemia, hyperphagia, thyroid dysfunction and infertility, and suggests that this peptide is a viable lead compound to be used in these efforts. The effectiveness of OB-3 in this animal model indicates that the peptide is not acting at the level of the leptin receptor. This novel and exciting observation raises the possibility that OB-3 may have therapeutic applications in clinical situations where treatment with recombinant leptin is shown to be ineffective.

The results of this study indicate that leptin-related synthetic peptides have in vivo effects on food consumption and weight gain which are similar to those of recombinant leptin; that leptin activity may be localized, at least in part, in domains between amino acid residues 106 and 140; and that development of synthetic peptide analogs or mimetics of leptin with greater potency and biological stability may be possible.

In addition to the above published study, we have recently attempted to identify additional active sites in the N-terminus of mouse leptin between amino acid residues 21 and 65, based on a report by Samson et al. (see Samson, et al., 1996. *Endocrinology* 137: 5182–5185) that a 35-amino acid fragment of leptin, representing residues 22–56, inhibited feeding in rats when administered into the lateral cerebral ventricle.

Four overlapping peptide amides, LEP(21–35), LEP (31–45), LEP(41–55) and LEP(51–65) were synthesized and their effects on food intake and body weight gain in female C57BL/6J ob/ob mice were examined. When administered at a dosage of 1 mg/day for 12 consecutive days, in contrast to what was seen for LEP(106–120), LEP(116–130) or LEP(126–140), weight gain (see FIG. 4) and food intake (see FIG. 5) by mice receiving these peptides was not significantly (i.e., P>0.05) different from that seen in vehicle-injected, control mice.

In addition, studies directed toward determining the minimal active sequence in our most active peptide in vivo, LEP(116–130), are in progress (see e.g., Grasso, et al., 1997. *Endocrinology* 138: 1413–1418). Utilizing a truncation peptide strategy, the activity of LEP(116–130) to the N-terminal seven amino acids in this region, OB-3 (see FIG. 6 and FIG. 7) at have been isolated. Accordingly, the OB-3 was selected as the "lead peptide" insubsequent efforts to increase its intrinsic potency and stability.

Initial experiments to determine the mechanism of action of LEP(116–130) utilized two highly sensitive in vitro bioassays routinely used to assess leptin binding and receptor activation (see e.g., White, et al., 1997. *Proc. Natl. Acad. Sci. USA*. 94: 10657–10662). An alkaline phosphatase ("AP")-leptin ("OB") fusion protein ("AP-OB") was used to measure inhibition of leptin binding in the absence or presence of recombinant mouse leptin (positive control) or peptide, by COS-7 cells transfected with the long (signaling) form of the mouse OB receptor ("OB-$R_L$"). Signal transduction assays were done in GT1-7 cells cotransfected with AP reporter and OB-$R_L$ constructs. Secreted alkaline phosphatase ("SEAP") activity in response to stimulation with mouse leptin or peptide was measured by chemiluminescence.

The results of these initial experiments indicated that LEP(116–130) was unable to inhibit binding of AP-OB by COS-7 cells, even at concentrations as high as 300 μM (see FIG. 8), suggesting that the observed in vivo activity may not be mediated by peptide interaction with and stimulation of OB-$R_L$. A second leptin-related peptide, LEP(145–160), shown to have no effect on food intake or body weight gain in vivo was also unable to inhibit AP-OB binding (see e.g., Grasso, et al., 1997. *Endocrinology* 138: 1413–1418).

In addition, we have determined that the mechanism of action by which at least one of our active peptides reduces food intake and body weight gain in vivo apparently is not the same as that of leptin. These results suggest that interaction with hypothalamic OB-R is not necessary for our observed effects, a critical observation with respect to the leptin resistance associated with human obesity. (See, e.g., Maffei, et al., 1995. *Nature Med*. 1: 1155–1161; Lonnqvist, et al., 1995. *Nat. Med*. 1: 950–953; Misra and Garg, 1996. *J. Invest. Med*. 44: 540–548).

In an effort to obtain further support for this notion, the effects of LEP(116–130) on food consumption and body weight gain in female db/db mice, genetically deficient in functional OB-R, was examined (see e.g., Chem, et al., 1996. *Cell* 84: 491–495; Lee, et al., 1996. *Nature* 379: 632–635). Daily ip administration of 1 mg/g body weight LEP(116–130) for 12 consecutive days reduced body weight gain, but not food intake, when compared to vehicle-injected control mice (see FIG. 10). These initial data are exciting in that they, too, suggest a mechanism of action that is different from that of leptin, and thus may have potential application in the treatment of human obesity.

Leptin-related Peptides, and Derivatives, Fragments, Homologs and Analogs Thereof The present invention discloses novel leptin-related peptides. In a preferred embodiment, the peptides are related to an animal leptin. In a more preferred embodiment, the peptides are related to a mammalian leptin In a most preferred embodiment, the peptides are related to a human leptin. In an variant preferred embodiment, the peptides are synthesized peptides. In one embodiment, the peptide is chosen from the C-terminal portion of the leptin protein. In another embodiment, the peptide is chosen from the N-terminal portion of the leptin protein. The present invention also relates to derivatives, fragments, homologs, analogs and variants of the aforementioned peptides.

We contemplate that the peptides of this invention include fusion proteins, particularly where the peptide is fused to a protein selected from the group consisting of alkaline phosphatase, glutathione-S-transferase and green fluorescent protein, or any antibody tag known in the art including myc 9E10, His tag, flag tag, and the like.

The present invention additionally relates to nucleic acids that encode the leptin-related peptides. The invention provides the nucleic acids comprising the coding regions, non-coding regions, or both, either alone or cloned in a recombinant vector, as well as oligonucleotides and related primer and primer pairs corresponding thereto. The nucleic acid strand may also be the complementary nucleic acid strand. Nucleic acids may be DNA, RNA, or a combination thereof. Vectors of the invention may be expression vectors.

The amino acid sequences of the aforementioned peptides are disclosed in SEQ ID NOS:2–16 and 18, respectively. Nucleic acids encoding said peptides may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like).

In one embodiment, a leptin peptide may have an amino acid sequence Xaa$_n$-Ser-Cys-Xaa$_1$-Leu-Pro-Xaa$_2$-Xaa$_3$-

$Xaa_n$, wherein $Xaa_n$ may be zero residues in length, or it may be a contiguous stretch of peptide residues derived from SEQ ID NOS: 1 or 17, preferably a stretch of between 1 and 7 at either the C-terminus or N-terminus, most preferably the peptide is a total of 15 amino acids or less in length. In another embodiment, $Xaa_1$, $Xaa_2$ or $Xaa_3$ may be any amino acid substitution. In yet another embodiment, $Xaa_1$, $Xaa_2$ or $Xaa_3$ may be any conservative amino acid substitution of the respective residues in full length mouse or human leptin [SEQ ID NOS:1 and 17, respectively]. In a further embodiment, $Xaa_1$ may be selected from the group consisting of His or Ser, and $Xaa_2$ or $Xaa_3$ is any amino acid substitution. In another embodiment, $Xaa_2$ may be selected from the group consisting of Trp or Gln, and $Xaa_1$ or $Xaa_3$ is any amino acid substitution. In yet another embodiment, $Xaa_3$ may be selected from the group consisting of Ala or Thr, and $Xaa_1$ or $Xaa_2$ is any amino acid substitution. In a preferred embodiment, $Xaa_1$ is selected from the group consisting of His or Ser, $Xaa_2$ is selected from the group consisting of Trp or Gln, and $Xaa_3$ is selected from the group consisting of Ala or Thr.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

Isolated Peptides and Polynucleotides

GenBank Accession numbers for mouse and human leptin and leptin receptor, providing the nucleotide and amino acid sequences for the disclosed leptin-related peptides and their encoding nucleic acids of the present invention, are provided in the BACKGROUND. The actual sequence of each peptide disclosed in the instant invention can readily be determined by comparison therein. The predicted amino acid sequence can then be determined from its nucleotide sequence using standard protocols well known in the art. The amino acid sequence of the peptide encoded by a particular clone can also be determined by expression of the clone in a suitable host cell, collecting the peptide and determining its sequence.

The invention also encompasses allelic variants of the disclosed polynucleotides or peptides; that is, naturally-occurring alternative forms of the isolated polynucleotide which also encode peptides which are identical, homologous or related to that encoded by the polynucleotides. Alternatively, non-naturally occurring variants may be produced by mutagenesis techniques or by direct synthesis.

Derivatives, fragments, and analogs provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively. Fragments are, at most, one nucleic acid-less or one amino acid-less than the wild type full length sequence. Derivatives and analogs may be full length or other than full length, if said derivative or analog contains a modified nucleic acid or amino acid, as described infra. Derivatives or analogs of the aforementioned peptides include, but are not limited to, molecules comprising regions that are substantially homologous to the aforementioned peptides, in various embodiments, by at least about 30%, 50%, 70%, 80%, or 95% identity (with a preferred identity of 80–95%) over an amino acid sequence of identical size or when compared to an aligned sequence in which the alignment is done by a computer homology program known in the art, or whose encoding nucleic acid is capable of hybridizing to the complement (e.g., the inverse complement) of a sequence encoding the aforementioned peptides under stringent (the preferred embodiment), moderately stringent, or low stringent conditions. See e.g., Ausubel, et al., CURRENT PROTOCOLS IN MOLECULAR BIOLOGY, John Wiley and Sons, New York, N.Y., 1993, and infra.

Preferably, as disclosed in the present invention, the aforementioned peptides are functionally active. In particular aspects, the aforementioned peptides, and fragments, derivatives, homologs or analogs thereof, are related to animals (e.g., mouse, rat, pig, cow, dog, monkey, frog), insects (e.g., fly), plants or, most preferably, human leptin. As utilized herein, the term "functionally active" refers to species displaying one or more known functional attributes of a full-length leptin.

In a preferred embodiment, the peptide of the invention has the ability to cross the blood-brain barrier.

Isolation of Homologs

Oligonucleotide probe or probes may be designed to correspond to sequences known for a particular clone. This sequence can be derived from the sequences provided herein, or from a combination of those sequences.

Homologs (i.e., nucleic acids encoding the aforementioned peptides derived from species other than human) or other related sequences (e.g., paralogs) can also be obtained by low, moderate or high stringency hybridization with all or a portion of the particular human sequence as a probe using methods well known in the art for nucleic acid hybridization and cloning.

In a most preferred embodiment, a nucleic acid sequence that is hybridizable to a nucleic acid sequence (or a complement of the foregoing) encoding the aforementioned peptides, or a derivative of the same, under conditions of high stringency is provided. By way of example and not limitation, procedures using such conditions of high stringency are as follows: Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5–20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

In a second embodiment, a nucleic acid sequence that is hybridizable to a nucleic acid sequence (or a complement of the foregoing) encoding the aforementioned peptides, or a derivatives, under conditions of moderate stringency is provided. By way of example and not ho limitation, procedures using such conditions of moderate stringency are as follows: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18–20 hours at 55° C. in the same solution with 5–20× 106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

In a third embodiment, a nucleic acid that is hybridizable to a nucleic acid sequence disclosed in this invention or to a nucleic acid sequence encoding a the aforementioned peptides, or fragments, analogs or derivatives under conditions of low stringency, is provided. By way of example and not limitation, procedures using such conditions of low stringency are as follows (see also Shilo and Weinberg, 1981, Proc Natl Acad Sci USA 78: 6789–6792): Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18–20 hours at 40° C. in the same solution with the addition of 0.02% PVP, 0.02% Ficoll, 0.2% BSA, 100 µg/ml salmon sperm DNA, 10% (wt/vol) dextran sulfate, and 5–20×106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65–68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The invention also relates to nucleic acids hybridizable to or complementary to the foregoing sequences, in particular the invention provides the inverse complement to nucleic acids hybridizable to the foregoing sequences (i.e., the inverse complement of a nucleic acid strand has the complementary sequence running in reverse orientation to the strand so that the inverse complement would hybridize with little or no mismatches to the nucleic acid strand). In specific aspects, nucleic acid molecules encoding derivatives and analogs of an aforementioned peptide (supra), or antisense nucleic acids to the same (see, e.g., infra) are additionally provided.

Recombinant Technologies for Obtaining the Aforementioned Peptides

The aforementioned peptides may be obtained by methods well-known in the art for peptide purification and recombinant peptide expression. For recombinant expression of one or more of the peptides, the nucleic acid containing all or a portion of the nucleotide sequence encoding the peptide may be inserted into an appropriate expression vector (i e., a vector that contains the necessary elements for the transcription and translation of the inserted peptide coding sequence). In a preferred embodiment, the regulatory elements are heterologous (i.e., not the native gene promoter). Alternately, the necessary transcriptional and translational signals may also be supplied by the native promoter for the genes and/or their flanking regions.

Host-vector Systems

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Any of the methodologies known within the relevant prior art regarding the insertion of nucleic acid fragments into a vector may be utilized to construct expression vectors that contain a chimeric gene comprised of the appropriate transcriptional/translational control signals and peptide-coding sequences. Promoter/enhancer sequences within expression vectors may utilize plant, animal, insect, or fungus regulatory sequences, as provided in the invention.

Promoter/enhancer elements from yeast and other fungi (e.g. the Gal4 promoter, the alcohol dehydrogenase promoter, the phosphoglycerol kinase promoter, the alkaline phosphatase promoter), as well as from animal transcriptional control regions, for example, those that possess tissue specificity and have been used in transgenic animals, may be utilized in the production of peptides of the present invention. Transcriptional control sequences derived from animals include, but are not limited to: (i) the insulin gene control region active within pancreatic β-cells (see, e.g., Hanahan, et al., 1985. Nature 315: 115–122); (ii) the immunoglobulin gene control region active within lymphoid cells (see, e.g., Grosschedl, et al., 1984. Cell 38: 647–658); (iii) the albumin gene control region active within liver (see, e.g., Pinckert, et al., 1987. Genes and Dev 1: 268–276; (iv) the myelin basic protein gene control region active within brain oligodendrocyte cells (see, e.g., Readhead, et al., 1987. Cell 48: 703–712); and (v) the gonadotrophin-releasing hormone gene control region active within the hypothalamus (see, e.g., Mason, et al., 1986. Science 234: 1372–1378), and the like. In a preferred embodiment, a vector is utilized that is comprised of a promoter operably-linked to nucleic acid sequences encoding the aforementioned peptides, one or more origins of replication, and, optionally, one or more selectable markers.

Once the recombinant molecules have been identified and the complex or individual proteins isolated, and a suitable host system and growth conditions have been established, using methods and systems well known within the art, the recombinant expression vectors may be propagated and amplified in-quantity. As previously discussed, expression vectors or their derivatives that can be used include, but are not limited to, human or animal viruses (e.g., vaccinia virus or adenovirus); insect viruses (e.g., baculovirus); yeast vectors; bacteriophage vectors (e.g., lambda phage); plasmid vectors and cosmid vectors.

Modification

A host cell strain may be selected that modulates the expression of inserted sequences of interest, or modifies or processes expressed peptides encoded by said sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

In a specific embodiment of the present invention, the nucleic acids encoding peptides, and peptides consisting of or comprising a fragment of the aforementioned leptin-related sequences that consists of a minimum of 6 contiguous amino acid residues of the aforementioned peptides, are provided herein. Derivatives or analogs of the aforementioned peptides include, but are not limited to, molecules comprising regions that are substantially homologous to the aforementioned peptides in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art or (iii) the encoding nucleic acid is capable of hybridizing to a sequence encoding the aforementioned peptides under stringent (preferred), moderately stringent, or non-stringent conditions (see, e.g. supra).

Derivatives of the aforementioned peptides may be produced by alteration of their sequences by substitutions, additions or deletions that result in functionally-equivalent molecules. In a specific embodiment of the present invention, the degeneracy of nucleotide coding sequences allows for the use of other DNA sequences that encode substantially the same amino acid sequence. In another specific embodiment, one or more amino acid residues within the sequence of interest may be substituted by another amino acid of a similar polarity and net charge, thus resulting in a silent alteration. Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

Production of Derivatives and Analogs

Derivatives and analogs of the aforementioned peptides of the present invention may be produced by various methodologies known within the art. For example, the polypeptide sequences may be modified by any of numerous methods known within the art. See e.g., Sambrook, et al., 1990. *Molecular Cloning: A Laboratory Manual*, 2nd ed., (Cold Spring Harbor Laboratory Press; Cold Spring Harbor, N.Y.).

Isolation and Analysis of the Gene Product or Complex

Once a recombinant cell expressing an aforementioned peptide, or a fragment, homolog, analog or derivative thereof, is identified, the individual gene product or complex may be isolated and analyzed. This is achieved by assays that are based upon the physical and/or functional properties of the peptide or complex, including, but not limited to, radioactive labeling of the product followed by analysis by gel electrophoresis, immunoassay, cross-linking to marker-labeled products, and the like. The an aforementioned peptide may be isolated and purified by standard methods known in the art (either from synthetic sources, natural sources or recombinant host cells expressing the peptide/peptide complex) including, but not limited to, column chromatography (e.g., ion exchange, affinity, gel exclusion, reverse-phase, high pressure, fast protein liquid, etc), differential centrifugation, differential solubility, or similar methodologies used for the purification of peptides. Alternatively, once an aforementioned peptide or its derivative is identified, the amino acid sequence of the peptide can be deduced from the nucleic acid sequence of the gene from which it was encoded. Hence, the peptide or its derivative can be synthesized by standard chemical methodologies known in the art. See, e.g., Hunkapiller, et al., 1984. *Nature* 310: 105–111.

In a specific embodiment, an aforementioned peptide (whether produced by recombinant DNA techniques, chemical synthesis methods, or by purification from native sources) is made up from peptides, or fragments, analogs or derivatives thereof, that, as their primary amino acid, contain sequences substantially as depicted in SEQ ID NOS:2–16 and 18, as well as peptide substantially homologous thereto.

Manipulations of the Sequences

Manipulations of the sequences included within the scope of the invention may be made at the peptide level. Included within the scope of the present invention is an aforementioned peptide, or fragments, derivatives, fragments or analogs, that is differentially modified during or after translation or synthesis (e.g., by glycosylation, acetylation, phosphorylation, amidation, derivatization by known protecting/blocking groups, proteolytic cleavage, linkage to an antibody molecule or other cellular ligand, and the like). Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. In a specific embodiment, sequences of an aforementioned peptide are modified to include a fluorescent label. In another specific embodiment, an aforementioned peptide is modified by the incorporation of a heterofunctional reagent, wherein such heterofunctional reagent may be used to cross-link the members of the complex.

Production of Peptides—Expression from Tissue Culture Cells

In one embodiment, we contemplate a method of producing any one of the polypeptides set forth in SEQ ID NOS: 2–16 and 18, comprising culturing a cell that contains any one nucleic acid sequence encoding any one of the polypeptides set forth in SEQ ID NOS: 2–16 and 18 under conditions permitting the production of the polypeptide, and recovering the polypeptide from the culture medium or cell culture. Any method known in the art is contemplated for steps needed for production of the peptides including, but not limited to: culturing a cell of choice in an appropriate media; introducing a nucleic acid encoding a peptide of the invention; expressing the peptide from the nucleic acid; secreting the peptide into the culture medium, recovering the peptide from the cell or the culture medium, and purifying the peptide. See, e.g., Ausubel et al., (Eds). In: CURRENT PROTOCOLS IN MOLECULAR BIOLOGY. J. Wiley and Sons, New York, N.Y. 1998.

In another one embodiment, we contemplate a method of producing any one or more peptide of the peptides comprising SEQ ID NOS: 2–16 and 18 comprising introducing a polynucleotide which encodes, upon expression, for any peptide of SEQ ID NOS: 2–16 and 18 into a cell or introducing a peptide coding sequence by homologous recombination into a cell, such that the endogenous regulatory sequence regulates expression of a recombinant peptide gene, to make a peptide production cell; and culturing the peptide production cell under culture conditions which result in expression of the peptide. See, e.g., Ausubel et al., (Eds).

In: CURRENT PROTOCOLS IN MOLECULAR BIOLOGY. J. Wiley and Sons, New York, N.Y. 1998.

Cells so treated may then be introduced in vivo for therapeutic purposes by any method known in the art, including, but not limited to, implantation or transplantation of cells into a host subject, wherein the cells may be "naked" or encapsulated prior to implantation. Cells may be screened prior to implantation for various characteristics including, but not limited to, the level of peptide secreted, stability of expression, and the like.

Transgenic animals containing nucleic acids that encode any one or more of the peptides comprising SEQ ID NOS: 2–16 and 18 may also be used to express peptides of the invention.

Chemical Synthesis

Complexes of analogs and derivatives of an aforementioned peptide can be chemically synthesized. For example, a peptide corresponding to a portion of an aforementioned peptide that comprises the desired domain or that mediates the desired activity in vitro, may be synthesized by use of a peptide synthesizer. In cases where natural products are suspected of being mutant or are isolated from new species, the amino acid sequence of an aforementioned protein isolated from the natural source, as well as those expressed in vitro, or from synthesized expression vectors in vivo or in vitro, may be determined from analysis of the DNA sequence, or alternatively, by direct sequencing of the isolated protein. An aforementioned peptide may also be analyzed by hydrophilicity analysis (see, e.g., Hopp and Woods, 1981. *Proc Natl Acad Sci USA* 78: 3824–3828) that can be utilized to identify the hydrophobic and hydrophilic regions of the peptides, thus aiding in the design of substrates for experimental manipulation, such as in binding experiments, antibody synthesis, etc. Secondary structural analysis may also be performed to identify regions of an aforementioned peptide that assume specific structural motifs. See e.g., Chou and Fasman, 1974. *Biochem* 13: 222–223. Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography (see, e.g., Engstrom, 1974. *Biochem Exp Biol* 11: 7–13); mass spectroscopy and gas chromatography (see, e.g., METHODS IN PROTEIN SCIENCE, 1997. J. Wiley and Sons, New York, N.Y.) and computer modeling (see, e.g., Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Methodologies for Screening

The present invention provides methodologies for screening an aforementioned peptide, as well as derivatives, fragments and analogs thereof, for the ability to alter and/or modulate cellular functions, particularly those functions in which an aforementioned peptide have been implicated. These functions include, but are not limited to, weight control; regulation of metabolism; control of signal transduction; and pathological processes, as well as various other biological activities (e.g., binding to antibody against an aforementioned peptide, and the like). The derivatives, fragments or analogs that possess the desired immunogenicity and/or antigenicity may be utilized in immunoassays, for immunization, for inhibition of the activity of an aforementioned peptide, etc. For example, derivatives, fragments or analogs that retain, or alternatively lack or inhibit, a given property of interest may be utilized as inducers, or inhibitors, respectively, of such a property and its physiological correlates. Derivatives, fragments and analogs of an aforementioned peptide may be analyzed for the desired activity or activities by procedures known within the art.

Production of Antibodies

As disclosed by the present invention herein, the aforementioned peptides, or derivatives, fragments, analogs or homologs thereof, may be utilized as immunogens in the generation of antibodies that immunospecifically-bind these peptide components. Such antibodies include, but are not limited to, polyclonal, monoclonal, chimeric, single chain, $F_{ab}$ fragments and an $F_{ab}$ expression library. In a specific embodiment, antibodies to human peptides are disclosed. In another specific embodiment, fragments of the aforementioned peptides are used as immunogens for antibody production. Various procedures known within the art may be used for the production of polyclonal or monoclonal antibodies to an aforementioned peptide, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as *Bacille Calmette-Guerin* and *Corynebacterium parvum*.

For preparation of monoclonal antibodies directed towards an aforementioned peptide, or derivatives, fragments, analogs or homologs thereof, any technique that provides for the production of antibody molecules by continuous cell line culture may be utilized. Such techniques include, but are not limited to, the hybridoma technique (see Kohler and Milstein, 1975. *Nature* 256: 495–497); the trioma technique; the human B-cell hybridoma technique (see Kozbor, et al., 1983. *Immunol Today* 4: 72) and the EBV hybridoma technique to produce human monoclonal antibodies (see Cole, et al., 1985. In: *Monoclonal Antibodies and Cancer Therapy*, Alan R. Liss, Inc., pp. 77–96). Human monoclonal antibodies may be utilized in the practice of the present invention and may be produced by the use of human hybridomas (see Cote, et al., 1983. *Proc Natl Acad Sci USA* 80: 2026–2030) or by transforming human B-cells with Epstein Barr Virus in vitro (see Cole, et al., 1985. In: *Monoclonal Antibodies and Cancer Therapy* (Alan R. Liss, Inc., pp. 77–96).

According to the invention, techniques can be adapted for the production of single-chain antibodies specific to an aforementioned peptide (see, e.g., U.S. Pat. No. 4,946,778). In addition, methodologies can be adapted for the construction of $F_{ab}$ expression libraries (see, e.g., Huse, et al., 1989. *Science* 246: 1275–1281) to allow rapid and effective identification of monoclonal $F_{ab}$ fragments with the desired specificity for an aforementioned peptide or derivatives, fragments, analogs or homologs thereof. Non-human antibodies can be "humanized" by techniques well known in the art. See e.g., U.S. Pat. No. 5,225,539. Antibody fragments that contain the idiotypes to an aforementioned peptide may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an aforementioned peptide is facilitated by generation of hybridomas that bind to the fragment of an aforementioned peptide possessing such a domain. Antibodies that are specific for a domain within an aforementioned peptide, or derivative, fragments, analogs or homologs thereof, are also provided herein.

It should be noted that the aforementioned antibodies may be used in methods known within the art relating to the localization and/or quantitation of an aforementioned peptide (e.g., for use in measuring levels of the peptide within appropriate physiological samples, for use in diagnostic methods, for use in imaging the peptide, and the like). In a given embodiment, antibodies for the aforementioned peptides, or derivatives, fragments, analogs or homologs thereof that contain the antibody derived binding domain, are utilized as pharmacologically active compounds [hereinafter "Therapeutics"].

Uses in Diagnosis, Prognosis and Screening

The polynucleotides and peptides of the present invention are expected to exhibit one or more of the uses or biological activities identified above. Uses or activities described for peptides of the present invention may be provided by administration or use of such peptides or by administration or use of polynucleotides encoding such peptides (such as, for example, in gene therapies or vectors suitable for introduction of DNA).

The aforementioned peptides may serve as a "marker" for specific disease states that involve the disruption of physiological processes in which an aforementioned peptide is known to be involved. These physiological processes include, but are not limited to, modulation of body mass (i.e., weight). More specifically, a mammalian subject may be suffering from an abnormality resulting in decreased or increased leptin activity. In each case, the decreased or increased leptin activity may be manifested as a pathological state, such as obesity (decreased leptin activity) or anorexia (increased leptin activity). Leptin-related syndromes exhibit pathophysiologies that include: obesity, increased body fat deposition, hyperglycemia, hyperinsulinemia, hypothermia, hyperphagia, hyperphagia, and impaired thyroid and reproductive functions in both males and females, and may have potential extension of their application to other obesity-related dysfunctions (e.g., Type II or non-insulin-dependent diabetes mellitus (NIDDM)). Obesity, defined as an excess of body fat relative to lean body mass, is associated with numerous, important clinical and psychological morbidities, the former includes, but is not limited to: hypertension, elevated blood lipids, and Type II diabetes mellitus or NIDDM, and decreased life expectancy. Thus a novel leptin-like peptides of the present invention is predicted to have diagnostic and therapeutic utility. Peptides of the present invention have a greatly increased ability to cross the blood brain barrier, thus greatly improving efficacy and bioavailability of the peptide composition compared to recombinant leptin of the prior art. In addition, differentiation and classification of particular groups of patients possessing elevations or deficiencies of an aforementioned peptide may lead to new nosological classifications of diseases, thereby markedly advancing diagnostic ability.

The detection of physiological effects mediated by the aforementioned peptide may be utilized in the analysis of various diseases, and may provide critical information in various medical processes, including diagnosis, prognosis, identifying disease states as defined above, following a disease course, following the efficacy of an administered therapeutics, following therapeutic response, and the like. Similarly, both the nucleic acid sequences (and sequences complementary thereto) and antibodies specific to an aforementioned peptide can be used in diagnostics.

Immunoassays

Said molecules may be utilized in assays (e.g., immunoassays) to detect, prognose, diagnose, or monitor various conditions, diseases, and disorders characterized by aberrant levels of an aforementioned peptide, or monitor the treatment thereof. An "aberrant level" means an increased or decreased level in a sample relative to that present in an analogous sample from an unaffected part of the body, or from a subject not having the disorder. The aforementioned immunoassay may be performed by a methodology comprising contacting a sample derived from a patient with an antibody under conditions such that immunospecific-binding may occur, and subsequently detecting or measuring the amount of any immunospecific-binding by the antibody. In a specific embodiment, an antibody specific for an aforementioned peptide may be used to analyze a tissue or serum sample from a patient for the presence of an aforementioned peptide; wherein an aberrant level of an aforementioned peptide is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein-A immunoassays, etc.

Assays

Methodologies that are well-known within the art (e.g., immunoassays, nucleic acid hybridization assays, biological activity assays, and the like) may be used to determine whether one or more aforementioned peptides are present at either increased or decreased levels, or are absent, within samples derived from patients suffering from a particular disease or disorder, or possessing a predisposition to develop such a disease or disorder, as compared to the levels in samples from subjects not having such disease or disorder or predisposition thereto.

Accordingly, in specific embodiments of the present invention, diseases and disorders that involve increased/decreased levels of activity of one or more leptin or leptin related peptides may be treated with the leptin-related peptides of the present invention, or their ability to respond to said peptides may be screened for, by quantitatively ascertaining increased/decreased levels of: (i) the one or more aforementioned peptides; (ii) the mRNA encoding an aforementioned peptide (iii) the functional activity or (iv) modulation of body weight homeostasis, following administration of the peptides of the present invention.

The present invention additionally provides kits for diagnostic use that are comprised of one or more containers containing an antibody and, optionally, a labeled binding partner to said antibody. The label incorporated into the antibody may include, but is not limited to, a chemiluminescent, enzymatic, fluorescent, colorimetric or radioactive moiety. In another specific embodiment, kits for diagnostic use that are comprised of one or more containers containing modified or unmodified nucleic acids that encode, or alternatively, that are the complement to, an aforementioned peptide and, optionally, a labeled binding partner to said nucleic acids, are also provided. In an alternative specific embodiment, the kit may comprise, in one or more containers, a pair of oligonucleotide primers (e.g., each 6–30 nucleotides in length) that are capable of acting as amplification primers for polymerase chain reaction (PCR; see, e.g., Innis, et al., 1990. *PCR PROTOCOLS*, Academic Press, Inc., San Diego, Calif.), ligase chain reaction, cyclic probe reaction, and the like, or other methods known within the art. The kit may, optionally, further comprise a predetermined amount of a purified aforementioned peptide, or nucleic acids thereof, for use as a diagnostic, standard, or control in the aforementioned assays.

THERAPEUTIC USES AND BIOLOGICAL ACTIVITY

The polynucleotides and peptides of the present invention are expected to exhibit one or more of the uses or biological activities (including those associated with assays cited herein) identified below. Uses or activities described for peptides of the present invention may be provided by administration or use of such peptides or by administration or use of polynucleotides encoding such peptides (such as, for example, in gene therapies or vectors suitable for introduction of DNA).

Research Uses and Utilities

The polynucleotides provided by the present invention can be used by the research community for various purposes. The polynucleotides can be used to express recombinant peptides for analysis, characterization or therapeutic use; as markers for tissues in which the corresponding peptides is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-peptide antibodies using DNA immunization techniques; and as an antigen to raise anti-DNA antibodies or elicit another immune response. Where the polynucleotide encodes a peptides which binds or potentially binds to another protein (such as, for example, in a receptor-ligand interaction), the polynucleotide can also be used in interaction trap assays (such as, for example, that described in Gyuris et al., *Cell* 75: 791–803 (1993)) to identify polynucleotides encoding the other protein or receptor with which binding occurs or to identify inhibitors of the binding interaction.

The peptides provided by the present invention can similarly be used in assay to determine biological activity, including in a panel of multiple peptides for high-throughput screening; to raise antibodies or to elicit another immune response; as a reagent (including the labeled reagent) in assays designed to quantitatively determine levels of the peptides (or its as receptor) in biological fluids; as markers for tissues in which the corresponding peptides is most biologically active (either constitutively or at a particular stage of tissue differentiation or development or in a disease state); and, of course, to isolate correlative receptors. Where the peptide binds or potentially binds to another protein (such as, for example, in a receptor-ligand interaction), the peptide can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation: "MOLECULAR CLONING: A LABORATORY MANUAL", 2d ed., Cold Spring Harbor Laboratory Press, Sambrook et al. (eds.), 1989; and "METHODS IN ENZYMOLOGY (Vol. 152): Guide to Molecular Cloning Techniques", Academic Press, Berger and Kimmel (eds.), 1987.

Utility for OB-3 and Leptin-related Peptides of the Invention

OB-3 and leptin-related peptides of the invention are exceptionally strong candidates for the development of leptin-related analogs, or mimetics, with potential application to treatment of human pathophysiologies related to body weight homeostasis. The present findings suggest that OB-3 and leptin-related peptides of the invention have greatly improved efficacy of treatment over recombinant leptin protein. While the exact mechanism is not yet known, and is not a limitation to the invention, this increased efficacy is presumably due in part to the increased ability of these peptides to cross the blood brain barrier. Additional mechanism include their interaction with receptors other than the previously identified OB-R receptor encoded -by the db gene.

The present invention provides a method for treatment or prevention of various diseases and disorders by administration of a biologically-active therapeutic compound (hereinafter "Therapeutic"). Such Therapeutics include but are not limited to: (i) any one or more of the aforementioned peptides, and derivative, fragments, analogs and homologs thereof; (ii) antibodies directed against the aforementioned peptides; (iii) nucleic acids encoding an aforementioned peptide, and derivatives, fragments, analogs and homologs thereof; (iv) antisense nucleic acids to sequences encoding an aforementioned peptide, and (v) modulators (i.e., inhibitors, agonists and antagonists).

Diseases or disorders associated with levels of activity or aberrant levels of an aforementioned peptides may be treated by administration of a Therapeutic that modulates activity.

Disorders

Diseases and disorders that are characterized by increased (relative to a subject not suffering from said disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from said disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Determination of the Biological Effect of the Therapeutic

In preferred embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon said cell type(s). Compounds for use in therapy may be tested in suitable animal model systems including, but not limited to rats, mice, chicken, cows, monkeys, rabbits, and the like, prior to testing in human subjects. In a preferred embodiment, genetically obese C57BL/6J ob/ob or C57BLKS/J-m db/db mice are used. Similarly, for in vivo testing, any of the animal model system known in the art may be used prior to administration to human subjects.

Gene Therapy

In a specific embodiment of the present invention, nucleic acids comprising a sequence that encodes an aforementioned peptide, or functional derivatives thereof, are administered to modulate homeostasis of body weight and adipose tissue mass by way of gene therapy. In more specific embodiments, a nucleic acid or nucleic acids encoding an aforementioned peptide, or functional derivatives thereof, are administered by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of an aforementioned disease or disorder. Any of the methodologies relating to gene therapy available within the art may be used in the practice of the present invention. See e.g., Goldspiel, et al., 1993. *Clin Pharm* 12: 488–505.

In a preferred embodiment, the Therapeutic comprises a nucleic acid that is part of an expression vector expressing both of the aforementioned peptides, or fragments, derivatives or analogs thereof, within a suitable host. In a specific embodiment, such a nucleic acid possesses a promoter that is operably-linked to coding region(s) of an aforementioned peptide. Said promoter may be inducible or constitutive, and, optionally, tissue-specific. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932–8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429–4432), which can be used to "target" cell types that specifically express the receptors of interest, etc.

In another specific embodiment of the present invention, a nucleic acid-ligand complex may be produced in which the ligand comprises a fusogenic viral peptide designed so as to disrupt endosomes, thus allowing the nucleic acid to avoid subsequent lysosomal degradation. In yet another specific embodiment, the nucleic acid may be targeted in viva for cell-specific endocytosis and expression, by targeting a specific receptor. See e.g., PCT Publications WO 92/06180; WO93/14188 and WO 93/20221. Alternatively, the nucleic acid may be introduced intracellularly and incorporated within a host cell genome for expression by homologous recombination. See e.g., Zijlstra, et al., 1989. *Nature* 342: 435–438.

In another specific embodiment, a viral vector that contains nucleic acids encoding an aforementioned peptide is utilized. For example, retroviral vectors may be employed (see, e.g., Miller, et al., 1993. *Meth Enzymol* 217: 581–599) that have been modified to delete those retroviral-specific sequences that are not required for packaging of the viral genome, with its subsequent integration into host cell DNA. Nucleic acids may be cloned into a vector that facilitates delivery of the genes into a patient. See e.g., Boesen, et al., 1994. *Biotherapy* 6: 291–302; Kiem, et al., 1994. *Blood* 83: 1467–1473. Additionally, adenovirus may be used as an especially efficacious "vehicle" for the delivery of genes to the respiratory epithelia. Other targets for adenovirus-based delivery systems are liver, central nervous system, endothelial cells, and muscle. Adenoviruses also possess advantageous abilities to infect non-dividing cells. For a review see, e.g., Kozarsky and Wilson, 1993. *Curr Opin Gen Develop* 3: 499–503. Adenovirus-associated virus (AAV) has also been proposed for use in gene therapy. See e.g., Walsh, et al., 1993. *Proc Soc Exp Biol Med* 204: 289–300.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599–618. The chosen technique should provide for the stable transfer of the nucleic acid to the cell, such that the nucleic acid is expressible by the cell. Preferably, said transferred nucleic acid is heritable and expressible by the cell progeny.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973–985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

In a specific embodiment in which recombinant cells are used in gene therapy, stem or progenitor cells that can be isolated and maintained in vitro may be utilized. Such stem cells include, but are not limited to, hematopoietic stem cells (HSC), stem cells of epithelial tissues, and neural stem cells (see, e.g., Stemple and Anderson, 1992. *Cell* 71: 973–985). With respect to HSCs, any technique that provides for the isolation, propagation, and maintenance in vitro of HSC may be used in this specific embodiment of the invention. As previously discussed, the HSCs utilized for gene therapy are, preferably but not by way of limitation, autologous to the patient. When used, non-autologous HSCs are, preferably but not by way of limitation, utilized in conjunction with a method of suppressing transplantation immune reactions of the future host/patient. See e.g., Kodo, et al., 1984. *J Clin Invest* 73: 1377–1384. In a preferred embodiment, HSCs may be highly enriched (or produced in a substantially-pure form) by any techniques known within the art, prior to administration to the patient. See e.g., Witlock and Witte, 1982. *Proc Natl Acad Sci USA* 79: 3608–3612.

Administration and Dosing

The invention present discloses methods of treatment and prophylaxis by the administration to a subject of a pharmaceutically-effective amount of a Therapeutic of the invention. In a preferred embodiment, the Therapeutic is substantially purified and the subject is a mammal, and most preferably, human.

Pharmaceutical compositions. A peptide of the present invention (derived from whatever source defined herein, including without limitation from synthetic, recombinant and non-recombinant sources) may be used in a pharmaceutical composition when combined with a pharmaceutically acceptable carrier. Such compositions comprise a therapeutically-effective amount of a Therapeutic, and a pharmaceutically acceptable carrier. Such a composition may also be comprised of (in addition to peptide and a carrier) diluents, fillers, salts, buffers, stabilizers, solubilizers, and other materials well known in the art. As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration.

A peptide of the present invention may be active in multimers (e.g., heterodimers or homodimers) or complexes with itself or other peptides. As a result, pharmaceutical compositions of the invention may comprise a peptide of the invention in such multimeric or complexed form.

Methods of administration. Methods of administration include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant.

In an embodiment of the invention, i.p. administration of leptin peptide is contemplated and preferred.

Delivery. Various delivery systems are known and can be used to administer a Therapeutic of the present invention including, but not limited to: (i) encapsulation in liposomes, microparticles, microcapsules; (ii) recombinant cells capable of expressing the Therapeutic; (iii) receptor-mediated endocytosis (see, e.g., Wu and Wu, 1987. *J Biol Chem* 262:4429–4432); (iv) construction of a Therapeutic nucleic acid as part of a retroviral or other vector, and the like. In one embodiment of the present invention, the Therapeutic may be delivered in a vesicle, in particular a liposome. In a liposome, the peptide of the present invention is combined, in At addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, but not limited to: a delivery pump (see, e.g., Saudek, et al., 1989. *New Engl J Med* 321:574 and a semi-permeable polymeric material (see, e.g., Howard, et al., 1989. *J Neurosurg* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a peptide, the Therapeutic nucleic acid may be administered in vivo to promote expression of its encoded peptide, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (see, e.g., Joliot, et al., 1991. *Proc Natl Acad Sci USA* 88:1864–1868), and the like. Alternatively, a nucleic acid Therapeutic can be introduced intracellularly and incorporated within host cell DNA for expression, by homologous recombination.

Dosage. As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of peptide of the present invention with which to treat each individual patient. Initially, the attending physician will administer low doses of peptide of the present invention and observe the patient's response. Larger doses of peptide of the present invention may be administered until the optimal therapeutic effect is obtained for the patient, and at that point the dosage is not increased further. However, suitable dosage ranges for intravenous administration of the Therapeutics of the present invention are generally about 5–500 micrograms ($\mu$g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

Duration. The duration of intravenous therapy using the pharmaceutical composition of the present invention will vary, depending on the severity of the disease being treated and the condition and potential idiosyncratic response of each individual patient. It is contemplated that the duration of each application of the peptide of the present invention will be in the range of 12 to 24 hours of continuous intravenous administration. Ultimately the attending physician will decide on the appropriate duration of intravenous therapy using the pharmaceutical composition of the present invention.

Pharmaceutical pack or kit. The present invention also provides a pharmaceutical pack or kit, comprising one or more containers filled with one or more of the ingredients of the pharmaceutical compositions and Therapeutics of the present invention. Optionally associated with such container (s) may be a notice in the form prescribed by a governmental agency regulating the manufacture, use or sale of pharmaceuticals or biological products, which notice reflects approval by the agency of manufacture, use or sale for human administration.

Gene Therapy. Polynucleotides of the present invention can also be used for gene therapy. Gene therapy refers to therapy that is performed by the administration of a specific nucleic acid to a subject. Delivery of the Therapeutic nucleic acid into a mammalian subject may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. Polynucleotides of the invention may also be administered by other known methods for introduction of nucleic acid into a cell or organism (including, without limitation, in the form of viral vectors or naked DNA). Any of the methodologies relating to gene therapy available within the art may be used in the practice of the present invention. See e.g., Goldspiel, et al., 1993. *Clin Pharm* 12:488–505.

Cultured Cells. Cells may be cultured ex vivo in the presence of peptides of the present invention in order to proliferate or to produce a desired effect on or activity in such cells. Treated cells can then be introduced in vivo for therapeutic purposes.

Contemplated within the invention is a method of identifying a modulator and/or potential modulator of body mass homeostasis in situ comprising: contacting a cell with the presence or absence of peptide, the peptide comprising any one or more of the peptides of SEQ ID NOS: 2–16 and 18; determining the level of effect in cells so contacted compared to cells not so contacted; wherein when an increase or decrease in desired effect is determined in the presence of the peptide relative to in the absence of the peptide, the peptide is identified as a potential modulator of body mass homeostasis.

Also contemplated within the invention is a method of identifying a modulator and/or potential modulator of body mass homeostasis in vivo comprising: administering to a test animal doses of at least one peptide of the invention and comparing said animal to a placebo control animal over a prescribed time period, wherein the peptide comprises any one or more of the peptides of SEQ ID NOS: 2–16 and 18; determining the level of modulation in body homeostasis of the test animal compared to the control during the prescribed time period; wherein when an increase or decrease in desired effect is determined in the presence of the peptide relative to in the absence of the peptide, the peptide is identified as a potential modulator of body mass homeostasis. A peptide that causes the test animal to lose weight relative to the control animal may be selected as a drug that is useful in a weight loss diet regimen.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entirety.

SPECIFIC EXAMPLES

Example 1

Peptide Synthesis

Synthetic leptin-related peptide OB-3 ($^{116}$Ser-Cys-Ser-Leu-Pro-Gln-Thr$^{122}$)(SEQ ID NO:2) was synthesized as a peptide amide by the solid phase method on a Rainin Model PS 3 automated synthesizer. Fluorenylmethoxycarbonyl ("Fmoc")-protected L-amino acids were assembled on Rink (4,2',4-dimethyloxyphenyl-fluorenylmethoxycarbonyl-aminoinethyl) phenoxy resin. The completed peptide was cleaved from the resin with trifluoroacetic acid ("TFA") using sterile deionized water, ethanedithiol, anisole, and thioanisole as scavengers. The cleaved peptide was extracted with anhydrous ether, dried by lyophilization, and purified on a Rainin Dynamax preparative HPLC column (21.4 mm×25 cm; C18; 300Å pore diameter) using a linear acetonitrile gradient (0–100%) containing 0.05% TFA. Fidelity of synthesis was confirmed by mass spectral analysis.

Additional peptides were synthesized by the solid phase method (see e.g., Merrifield 1963. *J Am Chem Soc* 85: 2149–2154) on a Rainin Model PS 3 automated synthesizer. Generally, Fmoc-protected L-amino acids were used. To preclude potential problems with solubility, peptides judged to be acidic (overall negative charge at pH 7.0) were acetylated at the N-terminus and synthesized with a free acid at the C-terminus to maximize the negative charge. Peptides judged to be basic (overall positive charge at pH 7.0) were synthesized with a free N-terminal amino group and an amide C-terminus to maximize the positive charge. The initial synthesis of each peptide was done on a 0.1 mmole scale. Once optimal conditions for complete coupling of each amino acid in the sequence were determined, and the purity of the peptide product assessed, additional syntheses to obtain the required amount of pure peptide needed for in vivo testing were scaled up to 0.25 mmole. The assembled peptides were cleaved from the resin with trifluoroacetic acid in the presence of appropriate scavengers, supra. The cleaved peptides were extracted with anhydrous ether, dried by lyophilizalion, analyzed by reversed-phase HPLC on a Rainin Dynamax modular column (4.6 mm×25 cm, C18, 300-Å pore diameter) and purified on a Rainin Dynamax HPLC column (21.4 mm×25 cm, C18, 300-Å pore diameter). Fidelity of synthesis was confirmed by amino acid compositional and mass spectral analyses. Only peptides purified to 98+% were used in the in vivo studies outlined in EXAMPLE 7, infra.

Example 2

Animal Models

The C57BL/6J ob/ob mouse model has been used extensively by a number of laboratories to assess the effects of recombinant leptin on body weight and food intake. Since the ultimate objective of this research is to develop peptide analogs or mimetics of leptin with even greater potency than the native protein, consistency in the selection of an animal model is critical. Because the C57BL/6J ob/ob mouse model is so well characterized, we selected it for use in our studies with leptin-related peptides.

Genetically obese (C57BL/6J, ob/ob) and nonobese (C57BL/6J, +/+) female mice were used in our study. The mice received two daily ip injections of leptin-related synthetic peptides in 0.2 ml phosphate buffered saline ("PBS", pH 7.2) for a defined period of days, preferably up to 14 days. Food intake and body weight was monitored daily.

Example 3

Biological Effects of Synthetic Leptin-related Peptide

When administered to leptin-deficient female obese C57BL/6J ob/ob mice (1 mg/day, ip, 12 days), synthetic OB-3 reduced body weight gain and food intake when compared to vehicle-injected control mice (FIG. 2). Similar results were seen in leptin-resistant female obese db/db mice receiving synthetic OB-3 (1 mg/day, ip, 7 days) (see FIG. 3).

FIG. 2 demonstrates the effects of synthetic OB-3 on body weight gain and food intake by genetically obese female C57BL/6J ob/ob mice. The graphs show changes in body weight (expressed as percent of initial weight) and food intake (expressed as mg/gm body weight/mouse) for mice given vehicle or synthetic leptin-related peptide OB-3 (1 mg/day, ip, 12 days). Each value represents the mean±SEM change in body weight or mg food consumed/gm body weight/mouse in a group of six mice.

FIG. 3 demonstrates the effects of synthetic leptin-related peptide OB-3 on body weight gain and food intake by genetically obese female db/db mice. The graphs show changes in body weight (expressed as percent of initial weight) and food intake (expressed as mg/gm body weight/mouse) for mice given vehicle or synthetic leptin-related peptide OB-3 (1 mg/day, ip, 7 days). Each value represents the mean±SEM change in body weight, or mg food consumed/gm body weight/mouse in a group of six mice.

FIG. 4 demonstrates the effects of 7 daily injections (1 mg/g body weight, ip) of leptin-related synthetic peptides on body weight gain in female C57BL/6J ob/ob mice. The graph shows changes in body weight (expressed as percent of initial weight) for mice treated with vehicle or leptin-related synthetic peptides. Each value represents the mean±SEM change in body weight for a group of 6 mice.

Figure 5:
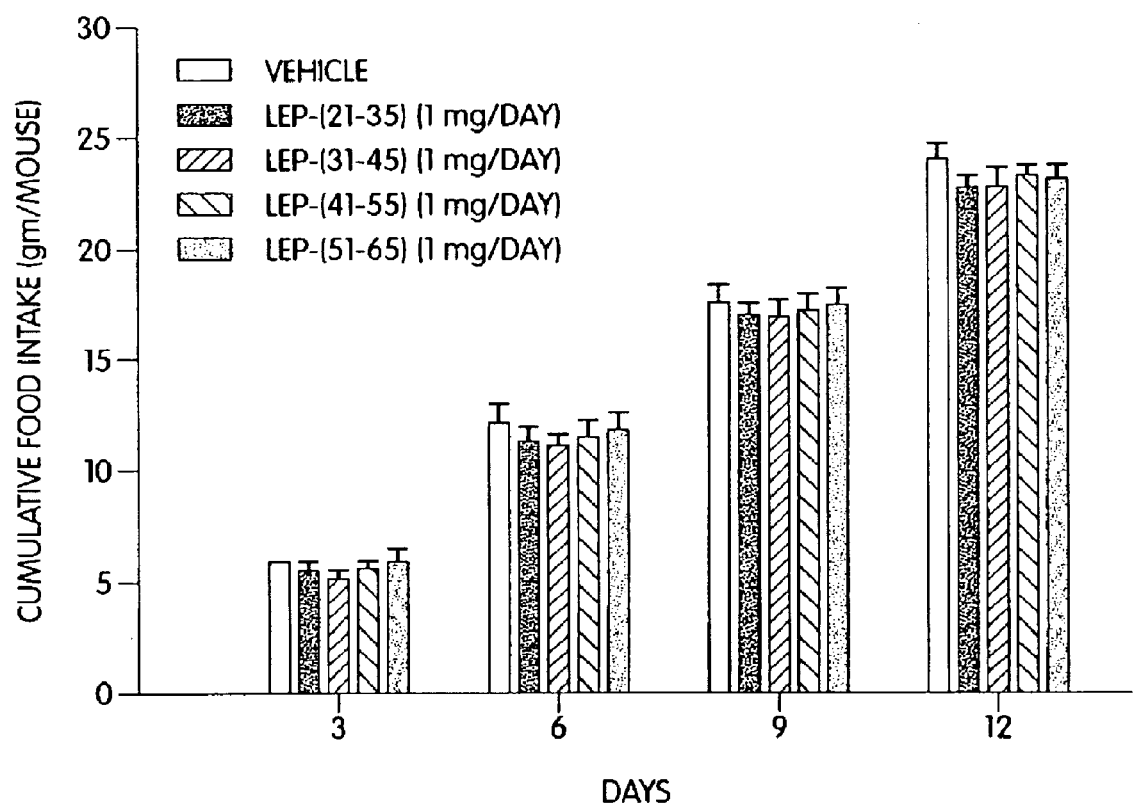
FIG. 5 is a graphic representation of the cumulative effects of various synthetic leptin peptides on food consumption in female C57BL/6J ob/ob mice.
Figure 6A:
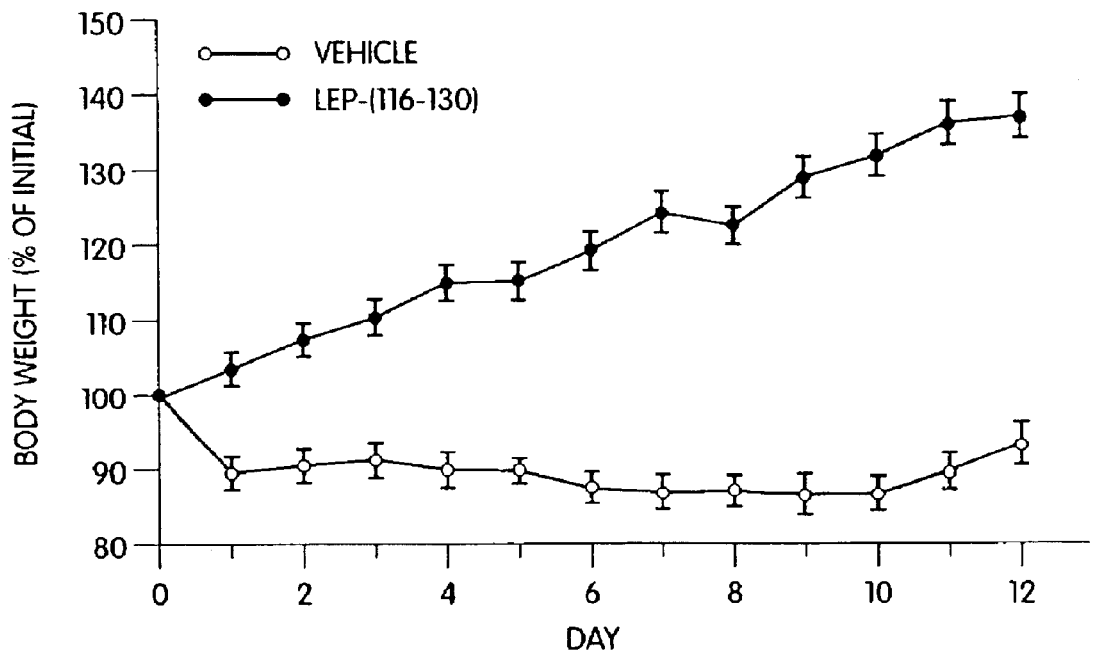
FIGS. 6A–6D are graphic representations of the effects of 12 daily injections of various synthetic leptin peptides on body weight gain in female C57BL/6J ob/ob mice.
Figure 6B:
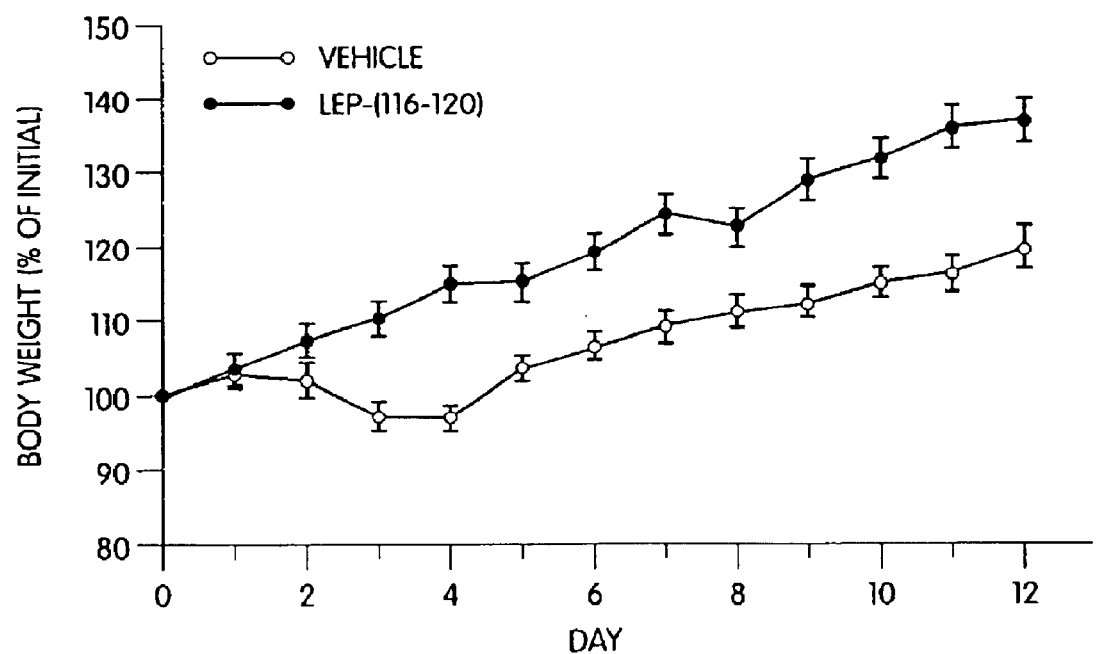
Figure 6C:
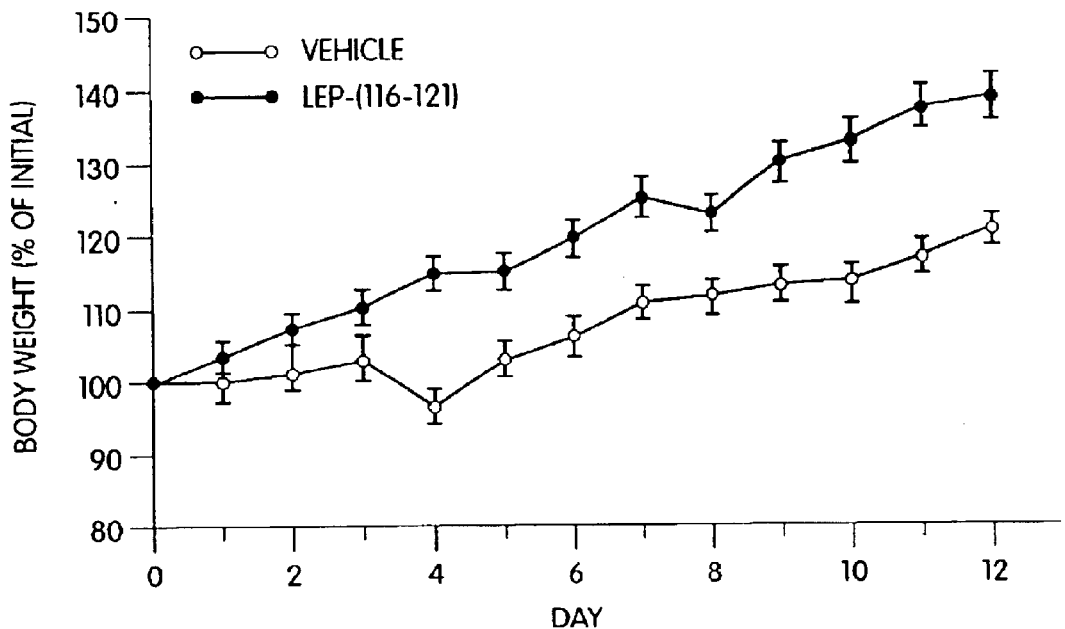
Figure 6D:
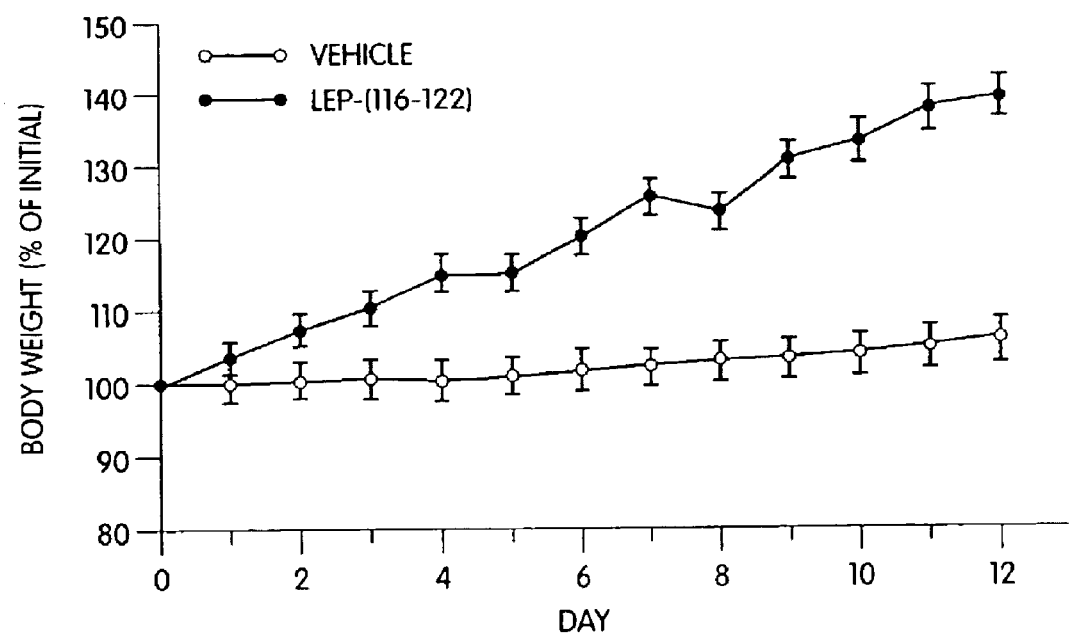

FIG. 5 demonstrates the cumulative effects of leptin-related synthetic peptides on food consumption by female C57BL/6J ob/ob mice. Mice were injected with leptin-related synthetic peptide (1 mg/g body weight, ip) or vehicle daily for 12 consecutive days. Each bar represents mean±SEM food consumption per mouse (n=6 mice per group) after 3, 6, 9 and 12 days of treatment.

FIG. 6 demonstrates the effects of 12 daily injections (1 mg/g body weight, ip) of leptin-related synthetic peptides on body weight gain in female C57BL/6J ob/ob mice. The graph shows changes in body weight (expressed as percent of initial weight) for mice treated with vehicle, LEP (116–130), or truncated synthetic peptide analogs of LEP (116–130). Each value represents mean±SEM change in body weight for a group of 6 mice.

Figure 7:
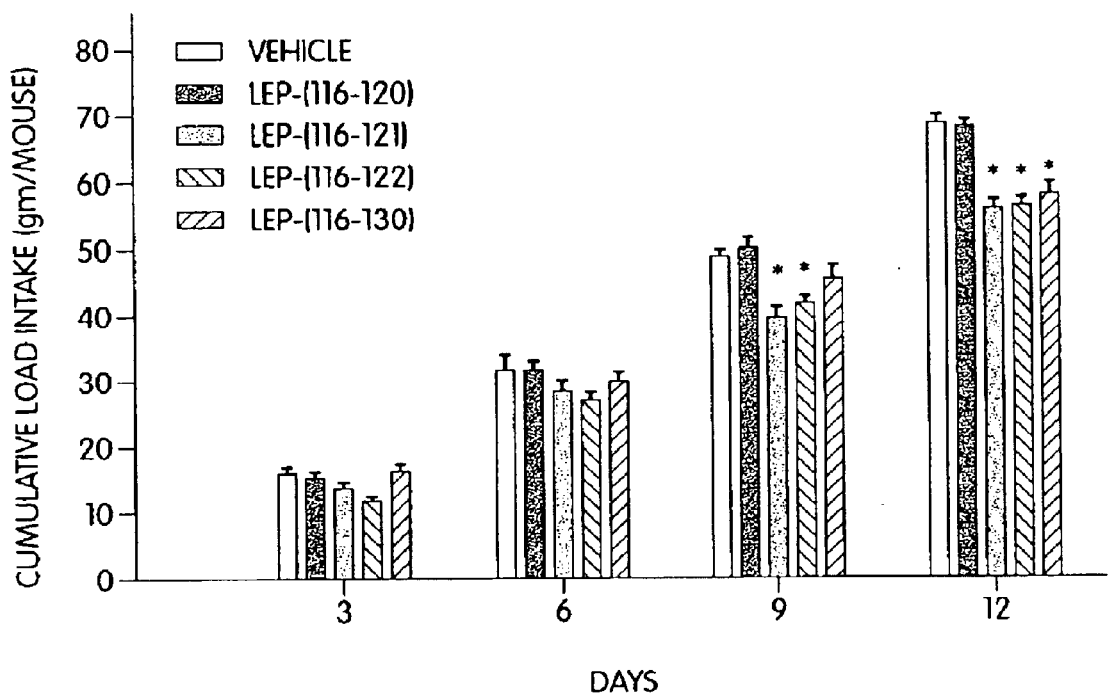
FIG. 7 is a graphic representation of the cumulative effects of various synthetic leptin-related peptides on food consumption in female C57BL/6J ob/ob mice.

FIG. 7 demonstrates the cumulative effects of synthetic LEP(116–130) and truncated synthetic peptide analogs of LEP(116–130) on food consumption by female C57BL/6J ob/ob mice. Mice were injected with leptin-related synthetic peptide (1 mg/g body weight, ip) or vehicle for 12 consecutive days. Each bar and vertical line represents mean±food consumption per mouse (n6 mice per group) after 3, 6, 9 and 12 days of treatment. Food consumption was significantly (*, P<0.05) less than vehicle-injected control mice when compared by Dunnett's Multiple Range test.

Figure 8:
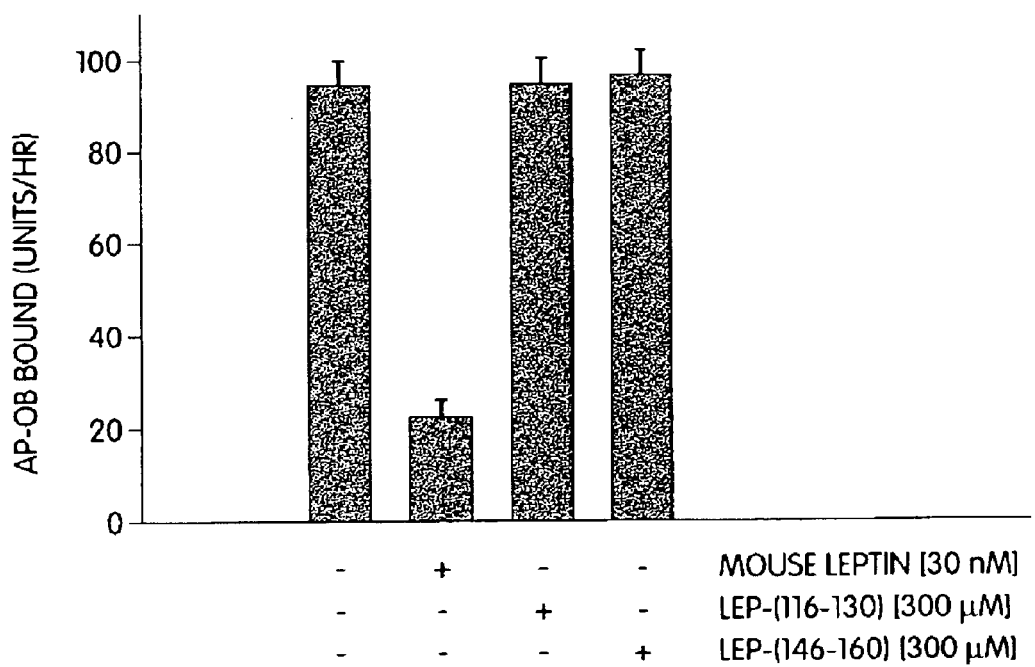
FIG. 8 is a graphic representation of the inhibition of alkaline phosphatase-leptin ("AP-OB") fusion protein binding in COS-7 cells by mouse leptin and various leptin-related synthetic peptides.

FIG. 8 demonstrates the inhibition of alkaline phosphatase ("AP") leptin ("OB") fusion protein ("AP-OB") binding by mouse leptin and leptin-related synthetic peptides. Two days after transfection, COS-7 cells were incubated with 1 nm human AP-OB fusion protein and bound AP activity was determined by chemiluminescence using the Great EscApe alkaline phosphatase detection kit as described by the manufacturer (CLON-TECH).

Figure 9:
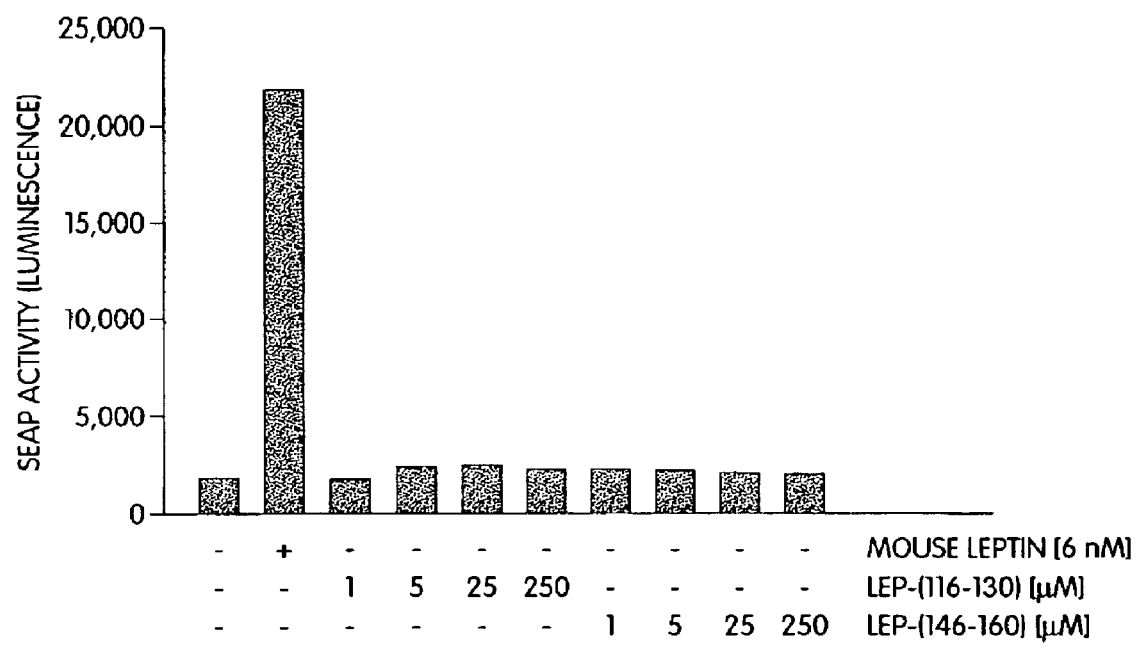

FIG. 9 demonstrates the secreted alkaline phosphatase ("SEAP") activity in GT1-7 cells stimulated with mouse leptin or leptin-related synthetic peptides. Two days after transfection, the cells were stimulated with mouse leptin or leptin-related synthetic peptides for 24 hours. Growth media were harvested and SEAP activity was determined by chemiluminescence as described for AP-OB binding studies.

Figure 10A:
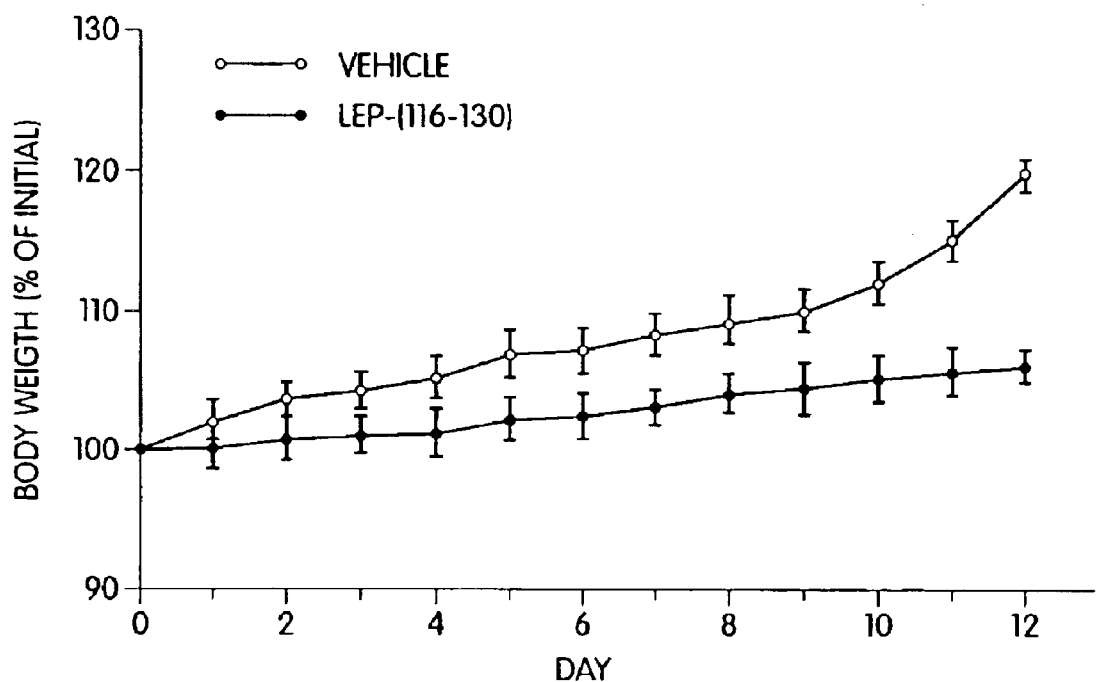
FIGS. 10A and 10B are graphic representations of the effects of 12 daily injections of LEP(116–130) synthetic peptide on body weight gain and food consumption in female db/db mice.
Figure 10B:
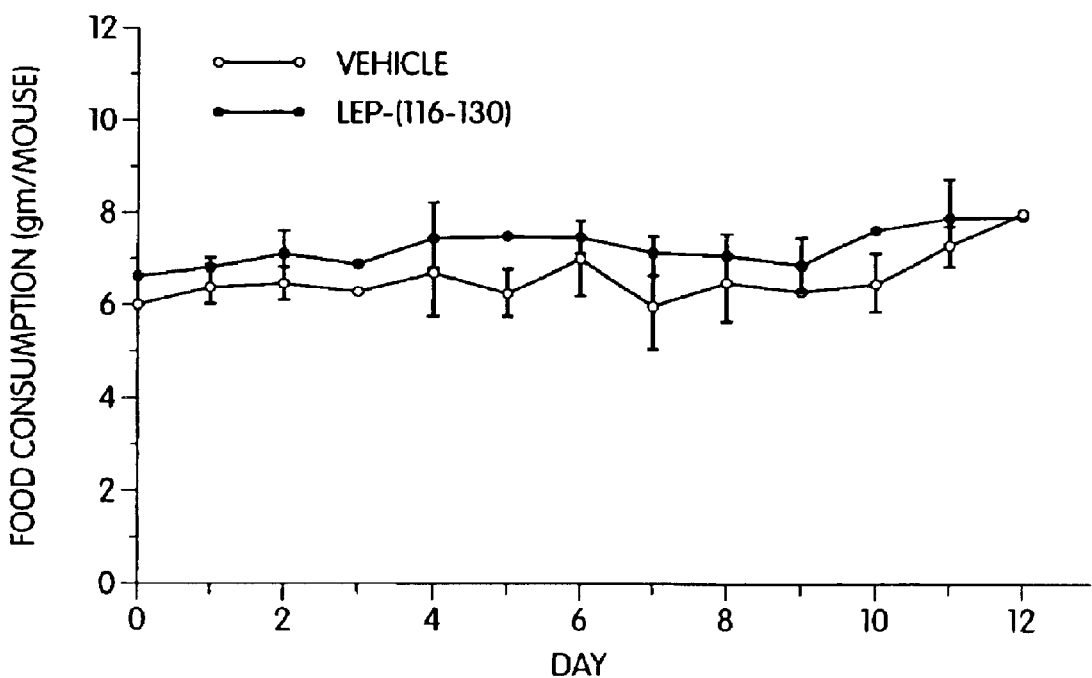

FIG. 10 demonstrates the effects of 12 daily injections (1 mg/g body weight, ip) of LEP(116–130) in female db/db mice. The graphs show changes in body weight (expressed as percent of initial weight) and food consumption (expressed as gm/mouse) for mice treated with vehicle or LEP(116–130), a peptide which is active in female C57BL/6J ob/ob mice (see e.g., Grasso, et al., 1997. Endocrinology 138: 1413–1418). Each point represents the mean±SEM change in body weight or food intake/mouse in a group of 6 mice.

Example 4

Active Site(s) in LEP(106–120), LEP(116–130) and LEP(126–140)

An essential element in the design of biologically potent peptides is an understanding of the contribution of each of the individual amino acids within a peptide sequence to receptor recognition or to overall peptide conformation. Amino acid residues which do not contribute to receptor binding often serve a structural role that allows the peptide to assume a conformation that facilitates optimal interaction with receptor. These amino acid residues can often be totally or partially deleted from a given sequence, with the resulting peptide fragment retaining full or partial activity (see e.g., Bryan, 1991. Meth. Enzymol. 202: 436–448). Given the fact that very few side-chain interactions are known to be critical for receptor activation, and that functional epitopes of protein ligands appear to be much smaller than their structural epitopes, it has become feasible to mimic the function of larger proteins with truncated peptide analogs (see e.g., Wells, 1995. Biotechnology 13: 647–651; Wells, 1996. Proc. Natl. Acad Sci. USA. 93: 1–6; Grasso, et al., 1995. Regulatory Pept. 60: 177–183; Grasso and Reichert, 1991. Endocrinol. 137: 5370–5375).

The results disclosed herein suggest the presence of active domains between amino acid residues 106 and 140 of mouse leptin (see e.g., Grasso, et al., 1997. Endocrinology 138: 1413–1418). This data indicates that three overlapping synthetic peptide amides corresponding to this region mimic, although at lower potency, the effects of recombinant leptin on food intake and body weight in ob/ob mice. Most activity is observed in response to ip administration of LEP (106–120) and LEP(116–130) peptide amides, suggesting that the overlapping residues in both peptides, namely Ser-116, Cys-17, Ser-118, Leu-119 and Pro-120 in mouse (and Ser-116, Cys-117, His-118, Leu-119 and Pro-120 in humans), may be important to their activity, and may comprise an active site in this portion of leptin. We synthesized LEP(116–120), a truncated analog of LEP(116–130) corresponding to residues 116 to 120, and assessed its effects on food intake and body weight in ob/ob mice. The truncated analog did not approximate the activity observed with LEP(116–130). Therefore, we coupled single amino acid residues distal to Pro-120, between positions 121 to 130, in the leptin sequence to the C-terminus of LEP(116–120), i.e., LEP(116–121), LEP(116–122) and so forth, until a peptide having equal or greater potency than LEP(116–130) was produced. As shown in FIG. 6, the in vitro activity of the synthetic peptide corresponding to mouse leptin sequence OB-3, i.e., LEP(116–122) [SEQ ID NOS:2], approximated the activity of the parent peptide LEP(116–130). These results suggest that the activity associated with the larger peptide resides in its N-terminal seven amino acid residues. Utilizing strategies described herein, we will synthesize additional peptide variants to improve the biological potency and stability of OB-3 to a level equal to or greater than that of recombinant leptin.

A similar approach will be taken with LEP(106–120). Single amino acid residues corresponding to positions 106 to 119 in the leptin sequence will be coupled to the N-terminus of LEP(116–120), i.e., LEP(115–120), LEP(114–120) and so forth, will be synthesized, until a peptide having equal or greater potency than LEP(106–120) is produced. As with OB-3, we will try to improve the biological potency and stability of the smaller peptides to a level equal to or greater than that of recombinant leptin using approaches described infra.

Peptide synthesis, purification and characterization are as described in EXAMPLE 1.

Example 5

Putative Active Sites in the N-Terminus of Leptin, Between Amino Acid Residues 22 and 105

As an alternative to site-directed mutagenesis, the utilization of synthetic peptides corresponding to restricted regions within the primary structures of a number of-protein hormones has resulted in the identification of peptide domains essential for both receptor recognition and signal transduction (see e.g., Santa-Coloma and Reichert, 1990. J. Biol. Chem. 265: 50–37–5042; Reichert, 1994. Mol. Cell. Endocrinol. 100: 21–27; Keutmann, 1992. Mol. Cell. Endocrinol. 86: C1–C6). These active peptides may themselves have usefulness as pharmaceutical agonists or antagonists, or may become lead compounds in the development of nonpeptide or peptidomimetic drugs. Strategies involving overlapping, or nested, peptides to identify active domains within protein sequences are commonly used in these efforts.

The mouse ob gene encodes an adipose tissue-specific, 4.5-kilobase mRNA with a widely conserved 167-amino acid open reading frame, and a 21-amino acid secretory signal sequence not normally found in circulating leptin (see e.g., Zhang, et al., 1994. *Nature* 372: 425–432). Therefore, a series of overlapping peptides, each approximately 15 amino acid residues in length, corresponding to the sequence between residues 22 to 105 of mouse leptin were synthesized. The peptides overlap at the N-terminus by 5 amino acid residues, and include LEP(21–35), LEP(31–45), LEP (41–55), LEP(51–65), LEP(61–75), LEP(71–85), LEP (81–95) and LEP(91–105). This strategy may allow: (i) the more precisely localization of the activity recently reported for a 35-amino acid fragment of leptin corresponding to residues 22 to 56 (see e.g. Samson, et al., 1996. *Endocrinology* 137: 5182–5185); (ii) identify additional active domains in the N-terminus of leptin; and (iii) provide other lead peptides with which to do truncation studies as described in EXAMPLE 4. This goal has already been accomplished, and the results of this work are included in the DETAILED DESCRIPTION.

Peptide synthesis, purification and characterization are as described in EXAMPLE 1.

Example 6

Improved Potency, Receptor-selectivity and Stability of Biologically Active Leptin-related Peptides An important goal in peptide research is to develop rational strategies in the design of peptide ligands with specific physical, chemical and biological properties. Consideration of the conformational flexibility of peptides is critical to these efforts. In solution, peptides are more flexible than proteins, which possess a single main conformer, but are less flexible than low molecular weight compounds, which have no unique three-dimensional structure (see e.g., Nikiforowich, 1994. *Int J Pept Protein Res* 44: 513–531). Under physiological conditions, most peptides exist as a mixture of more or less well-defined, interconverting conformers, and receptors select "receptor-bound", i.e., biologically active, conformers from among all those present. The design of peptide ligands of high potency and stability includes the utilization of strategies which will enhance the biological activity of active conformers by the insertion of conformational constraints into their structures.

Peptide Design

Alanine scan: In the development of peptide ligands of high potency, selectivity and stability, consideration must be given to the side chain groups of each amino acid residue in a given sequence. Questions regarding their specific requirements for bioactivity can be addressed by alanine (Ala) or glycine (Gly) scan (see e.g., Hruby, et al., 1995. *Ann. N.Y. Acad. Sci.* 757: 7–22). In this approach, each amino acid residue is replaced one at a time either by Ala or Gly, and the effect of the replacement is examined in a receptor binding or in vivo bioassay. For those analogs that retain activity, it is concluded that the side chain group of the particular substituted residue is not important for biological activity. For those analogs that lose activity, the side chain group is assumed to be critical Moreover, it is important that in vitro data be validated in vivo.

Alanine scan will be used to assess the contribution of each amino acid residue to the activity of LEP(106–120), (116–130), (126–140) or other biologically active lead peptides resulting from the efforts described herein and, specifically, in EXAMPLES 3–5. This strategy has recently enabled us to determine the importance of specific amino acid residues to the observed antagonist activity of a peptide corresponding to residues 32 to 46 of the glycoprotein hormone common alpha-subunit (see e.g., Leng, et al., 1995. *Pept Res* 8: 72–277). These efforts will yield valuable information needed to further develop potent leptin peptide analogs or mimetics.

Specific peptides will be designed based on experiment results, derived as described in EXAMPLES 4 and 5, that identity those sequences containing the active sites. Specifically, the strategies will initially focus on, but not be restricted to, (i) Ala substitution for Cys residues, if present in the sequence, given their potential for disulfide bond formation, and (ii) using Ala to reduce the number of positively or negatively charged residues in the sequence, since the observed in vitro activity may be dependent on charge-charge interactions.

At D-amino acid substitution: Systematic replacement of L-amino acids by their corresponding D-amino acid isoforms has been used to ascertain the stereostructural requirements of specific amino acid residues for peptide- receptor interactions, as well as the contribution of secondary structural motifs, (alpha-helix, beta-sheet, beta-tum) to the bioactivity of peptides (see e.g., Eruby, 1993. *Biopolymers* 33:1073–1082). This approach has also been shown to increase the resistance of peptides to enzymatic hydrolysis, and to enhance one or more properties of biologically active peptides, i.e., receptor binding, functional potency or duration of action (see e.g., Doherty, et al., 1993. *J. Med. Chem.* 36: 2585–2594; Kirby, et al., 1993. *J. Med. Chem.* 36:3802–3808; Morita, et al., 1994. *FEBS Lett.* 353: 84–88; Wang, et al., 1993. *Int. J. Pept. Protein Res.* 42: 392–399; Fauchere and Thiunieau, 1992. *Adv. Drug Res.* 23: 127–159).

Initial efforts to increase the potency and stability of biologically active leptin-related peptides will utilize a strategy in which a series of peptide analogs will be synthesized, each of which will contain a single D-amino acid which corresponds to its L-isomer in the native sequence. Should these efforts result in the development of a D-amino acid analog of higher potency and stability than the native L-form, this D-analog will be used as the lead peptide for introducing additional substituted D-isoforms into the native sequence, i.e., analogs containing two, three, four, and so forth, D-amino acids will be synthesized. We have recently shown this approach to be effective in the development of a synthetic glycoprotein hormone antagonist (see e.g., Leng, et al., 1996. *Pept. Res.* 9: 189–194), and expect it will have merit when applied to leptin-related peptides as well.

Cyclization. Another strategy which can be used to develop peptide analogs of increased potency, selectivity and stability relies on the introduction of covalent cross-links into a peptide sequence to conformationally and topographically constrain the peptide backbone. Macrocyclization is often accomplished by forming an amide bond between the peptide N- and C-termnini, between a side chain and the N- or C-terminus, or between two amino acid side chains. See, e.g., DeGrado, *Adv Protein Chem*, 39: 51–124 (1988). Disulfide bridges are also introduced into linear sequences to reduce their flexibility. See, e.g., Rose, et al., *Adv Protein Chem*, 37: 1–109 (1985). Because the conformational entropy of a cyclic peptide is lower than its linear counterpart, adoption of a specific conformation may occur with a smaller decrease in entropy for a cyclic analog than for an acyclic analog, thereby making the free energy for the process more favorable.

At least three approaches will be used to introduce global constraints into biologically active lead peptides. If their sequences allow, we will cyclize linear peptides by oxidation in $K_3Fe(CN)_6$ at pH 8.5, as recently described by Samson et al. (see, *Endocrinology*, (1996) 137: 5182–5185). Alternatively, half-cysteine replacement by half-penicillamine (ββ gem-dimethyl half-cysteine), with or without D-amino acid substitution, after the method of Mosberg et al. (see, *Biochem Biophys Res Commun*, (1982) 106: 505–512), will also be used to introduce conformational restrictions into disulfide-containing leptin analogs. While both of these approaches have been reported to increase the potency of linear peptides, the latter protocol, which combines conformational constraints imposed by cyclization via the disulfide and by the penicillamnine gem dimethyl groups, may lead to peptide conformations even more favorable to increased potency and receptor-selectivity.

When appropriate, the synthesis of cyclic lactam analogs of biologically active lead peptides will also be considered as an approach to improving their activity. This approach has been used successfully to produce potent analogs of glucagon, LHRH, CCK and GRF (see, e.g., Hruby and Bonna, *Methods Molec Biol*, 35: 201–240 (1994)), and may have merit when applied to leptin analogs. Bicyclization, which incorporates both lactam and disulfide constraints, as described by Hill et al. (see, *J Amer Chem Soc*, (1990) 112: 3110–3113) for oxytocin, may also be effective in the development of leptin analogs or mimetics of high potency, receptor selectivity and biological stability.

Linear coupling of biologically active lead peptides. In an earlier report, we have shown that a synthetic peptide amide encompassing two discontinuous regions of the human FSH β-subunit, each known to interact with the FSH receptor, possessed higher affinity for the receptor than either of the two smaller peptides representing the individual binding domains. See, e.g., Santa-Coloma, et al., *Mol Cell Endocrinol*, 78: 197–204 (1991). These results suggested to us that each binding domain was effectively interacting with the receptor to contribute to the increased affinity of the larger peptide, and that linear coupling of discontinuous binding regions of a highly complex protein might result in a peptide analog that could mimic the binding surface of the native protein. Additional manipulations, i.e., insertion of spacing amino acids, D-amino acid substitution, or cyclization, have since resulted in the development of peptide analogs which have achieved or exceeded the affinity of their natural counterparts. See, e.g., Fauchere and Thurieau, *Adv Drug Res*, 23: 127–159 (1992). We will use linear coupling of biologically active leptin-related lead peptides as another approach to improving their potency.

Additional approaches: conformationally constrained amino acids. A number of other methods have been used successfully to introduce conformational constraints into peptide sequences in order to improve their potency, receptor selectivity and biological half-life. These efforts include the utilization of (i) $C_a$-methylamino acids (see, e.g., Rose, et al., *Adv Protein Chem*, 37: 1–109 (1985); Prasad and Balaram, *CRC Crit Rev Biochem*, 16: 307–348 (1984)); (ii) $N_a$-methylamino acids (see, e.g., Aubry, et al., *Int J Pept Protein Res*, 18: 195–202 (1981); Manavalan and Momany, *Biopolymers*, 19: 1943–1973 (1980)); and (iii) α,β-unsaturated amino acids (see, e.g., Bach and Gierasch, *Biopolymers*, 25: 5175–5192 (1986); Singh, et al., *Biopolymers*, 26: 819–829 (1987)). For the most part, these amino acid analogs have become commercially available, or can be prepared relatively easily. This approach will also be included in our efforts to develop leptin-related peptides of high potency.

Peptide synthesis, purification and characterization are as described in EXAMPLE 1.

Example 7

Studies to Assess the Effects of Leptin-related Synthetic Peptides on Food Intake and Energy Expenditure in Obese Female Mice Peripheral administration of low doses of recombinant leptin to hormone-deficient ob/ob mice has been shown to correct their hyperglycemia, hyperinsulinemia, and hypothermia, whereas higher doses normalized food intake and body weight. See, e.g., Pelleymounter, et al., *Science*, 269: 540–543 (1995); Weigle, et al., *J Clin Invest*, 96: 2065–2070 (1995); Barash, et al., *Endocrinology*, 137: 3144–3147 (1996); Campfield, et al., *Science*, 269: 546–549 (1995). Our own study has indicated that similar effects on food intake and energy expenditure can be achieved by peripheral administration of leptin-related synthetic peptides. See, e.g., Grasso, et al., *Endocrinology* 138: 1413–1418 (1997).

Female obese C57BL/6J ob/ob and C57BLKS/J-m db/db mice (6 per group) will be used in these studies. The mice will be housed six per cage and maintained in a constant-temperature room (24° C.) in the Albany Medical College Animal Resources Facility under alternating 12-h at light and dark periods (lights off 0900–2100 h).

Peptide synthesis, purification and characterization are as described in EXAMPLE 1.

Test peptides will be dissolved in sterile PBS (pH 7.2) and administered in two 0.2 ml ip injections daily for 14 days. Control mice will receive two 0.2 ml ip injections of PBS only. Recombinant mouse leptin, at a total daily dose of 6 μg/g initial body weight (BW), as described by Campfield et al. (see *Science*, 269: 546–549 (1995)), will be used as positive control. One-half of the daily dose of leptin (6 μg/g BW) and peptide (initially 1 mg/day to compare the potency of the newly designed peptides to LEP(116–130), our most potent peptide, and to recombinant leptin) will be given to the mice immediately before the onset of the dark period, and the remaining half will be given six hours into the dark period. Body weight and food intake will be recorded daily. Based on our preliminary studies (see, e.g., Grasso, et al., *Endocrinology* 138: 1413–1418 (1997)), this time frame should be sufficient for initial assessment of biological activity and to determine whether or not peptide effects are transient in nature. If peptide effects appear to diminish during the course of the 14 day test period, the concentration of peptide will be increased, initially by 100 μg, at that point in the experiment in an effort to restore the effects on body weight gain and food intake observed earlier. The mice will be closely monitored for possible toxic side effects, i.e., changes in coat quality, stool consistency, or activity level, at high concentrations of peptide. Peptide dose response studies will be done to determine the optimal peptide concentration required for maximal and sustained effects on weight loss and food consumption. Peptides will be tested twice (in separate experiments with a different group of 6 mice) to confirm any observed activity or lack thereof.

Example 8

Inhibitory Effects of LEP(116–130) Mediated by a Mechanism Other Than Peptide Activation of the Long Isoform of the Leptin Receptor We have utilized two in vitro bioassays to show that interaction of LEP(116–130) with full-length leptin receptor (OB-R$_b$), the receptor isoform predominantly expressed in the hypothalamus, is apparently not required for the observed in vivo effects of the peptide on energy balance. LEP(116–130) was unable to compete the binding of alkaline phosphatase-leptin fusion protein (AP-OB) to OB-R. Moreover, LEP(116–130) was unable to activate signal transduction by OB-R$_b$ in vitro. In homozygous female C57BLKS/J-m db/db mice, which do not express OB-R$_b$, ip administration of LEP(116–130) reduced body weight gain and blood glucose levels, but not food intake, further supporting a mechanism of action which does not require peptide interaction with OB-R$_b$. These results provide both in vitro and in vivo evidence that suggests that the effects of LEP(116–130) does not require peptide binding by OB-R or activation of OB-R$_b$. Although the mechanism of action by which LEP(116–130) exerts its effects on energy balance has yet to be determined, it is clear that this mechanism is different from that by which the leptin signal is transduced. This observation suggests that LEP(116–130), or analogs thereof, may have potential use in the development of alternative therapeutic approaches to the treatment of human obesity and its associated dysfunctions.

Peptide Synthesis, Purification and Characterization:

Peptide synthesis, purification and characterization are as described in EXAMPLE 1.

Expression Vectors and SEAP Reporter Gene Constructs:

The expression vectors for OB-R$_a$ and OB-R$_b$ have been previously described. See., e.g., White et al., 1997. *Proc Natl Acad Sci USA* 94: 10657–10662; Tartaglia et al., 1995. *Cell* 83: 1263–1271. The reporter gene construct pHRRE-SEAP was generated by subcloning the hematopoietin response element into the pSEAP-Promoter (CLONTECH) as has been reported previously. See., e.g., White et al., 1997. *Proc Natl Acad Sci USA* 94: 10657–10662. The luciferase reporter gene construct pGL3 was commercially obtained (Promega, Madison, Wis.).

Cell Transfection and Analysis:

COS-7 and GT-7 cells were cultured in DMEM supplemented with 10% fetal bovine serum, and transfected by the lipofectamine method. See, e.g., Baumann et al., 1996 *Proc Natl Acad Sci USA* 93: 8374–8378. For SEAP assays, GT1-7 cells were transfected with 1 μg pHRRE-SEAP, 0.5 μg pGL3, and 3 μg OB-R$_b$ receptor constructs. Forty-eight hours after transfection, cultures were washed twice with serum-free medium and stimulated with 6 nM mouse leptin or increasing concentrations of LEP(116–130) or LEP (146–160) for 24 h in nonsupplemented cell culture medium. LEP(146–160), shown to have no activity in vivo (see, Grasso et al., 1997. *Endocrinology* 138: 1413–1418), was used as negative control. Supernatants were collected and SEAP reporter activities were measured by chemiluminescence using the GreatEscApe alkaline phosphatase detection kit as described by the manufacturer (CLONTECH). Luminescence was measured in a Microbeta plus scintillation counter (Wallac, Gaithersburg, Md.) and expressed-as arbitrary units of luminescence activity. Cell lysates were generated using a luciferase assay system kit (Promega, Madison, Wis.) and luciferase activities were measured in a microplate ruminator (Tropix Corp., San Francisco, Calif.).

Analysis of LEP(116–130) Binding:

COS-7 cells were transfected with expression vector for OB-R$_a$. Two days after transfection, the cells were incubated with 1 nM human AB-OB fusion protein in the absence or presence of 30 nM mouse leptin, 300 μM LEP(116–130) or LEP(146–160). Bound AP activity was determined as has been described. See., e.g., Kamohara et al., 1997 *Nature* 389; 374–377.

Peptide administration: LEP(116–130) and LEP (146–160) peptide amides were dissolved in sterile phosphate buffered saline (PBS, pH 7.2) and administered daily for 7 days between 1500 and 1600 h in a single 1 mg/0.2 ml ip injection. Control mice received 0.2 ml PBS (ip) only.

Feeding and weighing schedule: On day one of the study, and on each day thereafter, 200 g of pelleted rodent diet (Prolab Rat, Mouse, Hamster 3000, St. Louis Mo.; 22% crude protein, 5% crude fat, 5% fiber, 6% ash, 2.5% additional minerals) was added to the hopper on each side of the cages between 0900 and 1100 h. Food remaining after 24 h was weighed to the nearest 0.1 g, and the average amount of food consumed per mouse was calculated (mean±SEM, n=6). The mice were allowed water ad libitum throughout the study, and were weighed once daily between 0900 and 1100 h.

Measurement of blood glucose and thermoregulatory studies: Blood was drawn from the tail vein of each mouse 2 h before the onset of the dark period at the beginning of the study (day 0), and after 2,4 and 6 days of treatment with 1 mg/day ip LEP(116–130). Blood glucose levels were determined using a Glucometer Elite (Bayer Corporation, Elkhart, Ind.) blood glucose monitor. After 4 and 7 days of treatment with 1 mg/day ip LEP(116–130), sensitivity to cold was examined by placing the mice without food or water in a cold room with an ambient temperature of 4° C. Body temperature was measured with a rectal probe every hour for 4 hours.

GT1-7 cells were cotransfected with the reporter gene construct HRRE-SEAP and cDNA encoding OB-R$_b$ and analyzed for reporter gene activation in the absence or presence of mouse leptin (6 nM) or increasing concentrations (1 to 250 uM) of LEP(116–130) (see FIG. 9). In the absence of ligand stimulation, transfected cells showed minimal reporter gene activity. SEAP activity was increased 11-fold by 6 nM mouse leptin. LEP(116–130), at all concentrations tested, was unable to stimulate SEAP activity above basal levels. LEP(146–160), inactive in vivo (see, Grasso et al., 1997. *Endocrinology* 138: 1413–1418), was also incapable of inducing an increase in reporter gene activity.

The effects of LEP(116–130) on ligand binding by OB-R is shown in FIG. 8. COS-7 cells transfected with OB-R$_a$ exhibit a large increase in AP-OB binding activity relative to mock transfected cells. Bound AP-OB was efficiently competed by the addition of 30 nM unlabelled mouse leptin in the binding assay. In contrast, neither LEP(116–130) nor LEP(146–160), at 300 μM, were able to inhibit AP-OB binding.

Figure 11A:
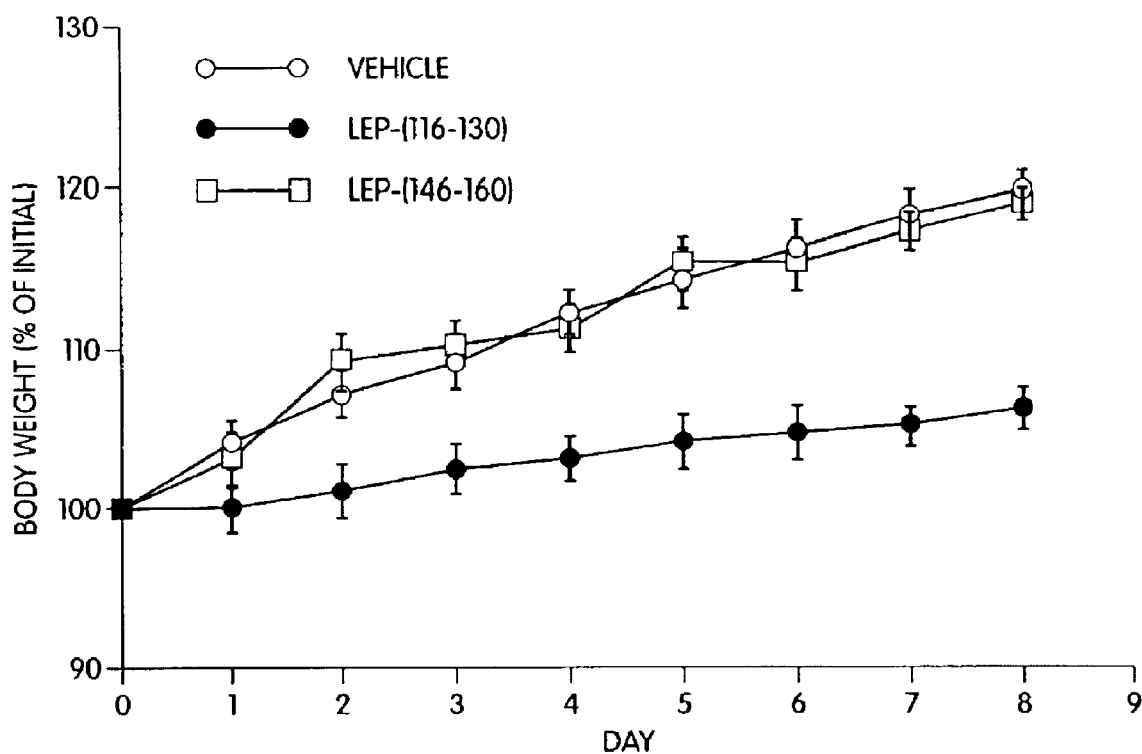
FIGS. 11A–11B are graphic representations of the effects of 7 daily injections of various synthetic leptin peptide on body weight gain and food consumption in genetically obese female C57BLKS/J-m db/db mice.

Effects of LEP(116130) on Body Weight Gain and Food Intake in db/db Mice:

FIG. 11 depicts the effects of 7 daily injections (1 mg, ip) of LEP(116–130) or LEP(146–160) peptide amide on body weight gain and food intake by female C57BLKS/J-m db/db mice. The graph shows changes in (Panel A) body weight (expressed as percent of initial weight), and (Panel B) food intake (expressed as gm food consumed/mouse) in mice treated with vehicle, LEP(116–130) or LEP(146–160) peptide amide. Each value represents the mean±SEM change in body weight or food intake for a group of six mice.

Figure 11B:
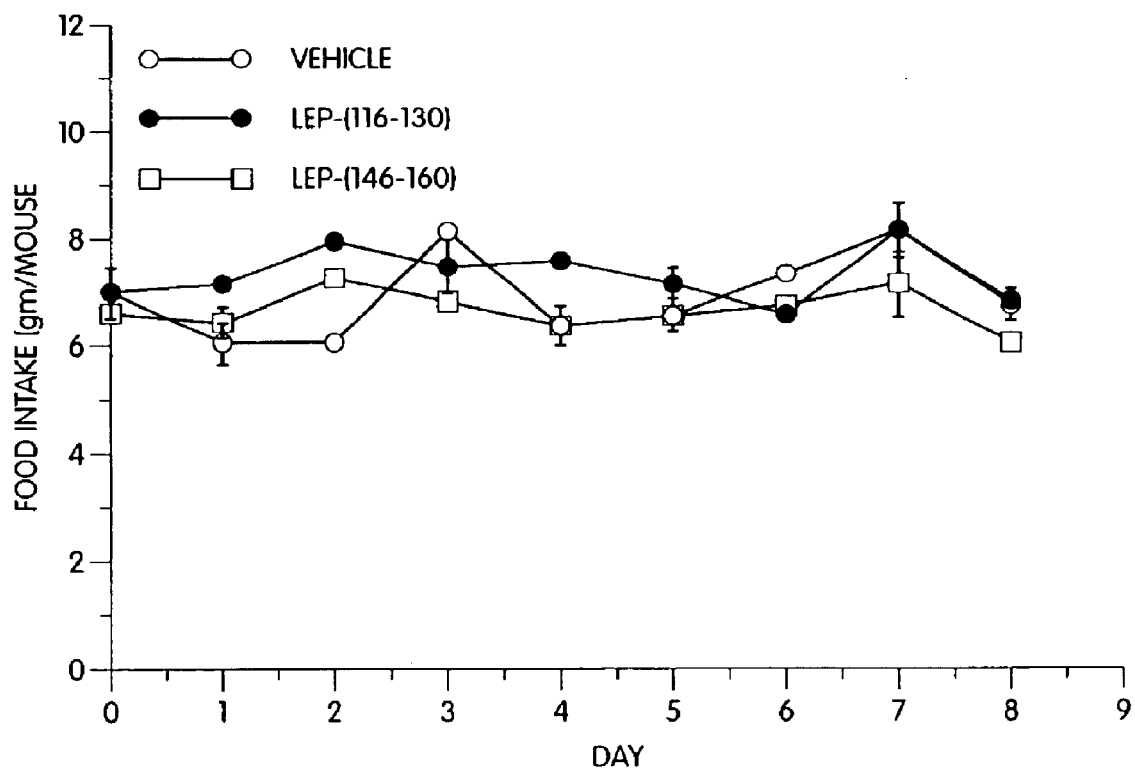

The results of our previous in vitro studies suggest that the observed in vivo effects of LEP(116–130) on body weight gain and food intake in female ob/ob mice were not mediated by peptide activation of hypothalamic OB-R. See, e.g., Grasso et al., 1997. *Endocrinology* 138: 1413–1418. To obtain further support for this notion, we examined the effects of LEP(116–130) on food intake and body weight gain in female db/db mice, genetically deficient in functional OB-R$_b$. Daily administration (ip) of 1 mg LEP(116–130) for 7 consecutive days resulted in a reduced rate of body weight gain (FIG. 11A and Table 1) in the presence of increased food intake (FIG. 11B and Table 2), when compared to vehicle-injected control mice. LEP(146–160) (1 mg/day, ip, 7 days) had no effect on either body weight (FIG. 11A and Table 1) or food consumption (FIG. 11B and Table 2).

TABLE 1

Effects of LEP(116-130) and LEP(146-160) peptide amides (1 mg/day, ip) on body weight gain in female db/db mice after 7 days of treatment.

|  | Vehicle | LEP(116-130) | LEP(146-160) |
|---|---|---|---|
| Initial weight (g)[a] | 29.8 ± 1.5 | 30.8 ± 1.6 | 30.6 ± 1.6 |
| Weight after 7 days (g)[a] | 35.7 ± 1.6 | 32.6 ± 1.8 | 36.2 ± 1.4 |
| Weight increase (g) | +5.9 | +1.8 | +5.6 |
| Percent increase | +19.8 | +5.8 | +18.3 |
| P[b] |  | 0.047 | 0.46 |

[a]Mean ± SEM (n = 6)
[b]Mean of the differences between the initial and 7-day body weight of each mouse (n = 6) in peptide-treated groups was compared with the mean of the differences between the initial and 7-day body weight of each vehicle-injected control mouse (n = 6). The P values (2-tailed) were determined by the Wilcoxon Sign Test.

TABLE 2

Cumulative effects of synthetic LEP(116-130) and LEP(146-160) peptides (1 mg/day, ip) on food intake in female db/db mice after 7 days of treatment.

| Treatment | Cumulative food intake (gm/mouse)[a] |
|---|---|
| Vehicle | 54.0 ± 0.3 |
| LEP(116-130) | 64.9 ± 0.2[b] |
| LEP(146-160) | 53.5 ± 0.3 |

[a]Mean ± SEM
[b]P = 0.021. The cumulative food intake by mice (n = 6) in the LEP(116-130) - treated group was compared to the cumulative food intake by vehicle-injected control mice (n = 6). The P value (2-tailed) was determined by the Wilcoxon Sign Test.

Figure 12:
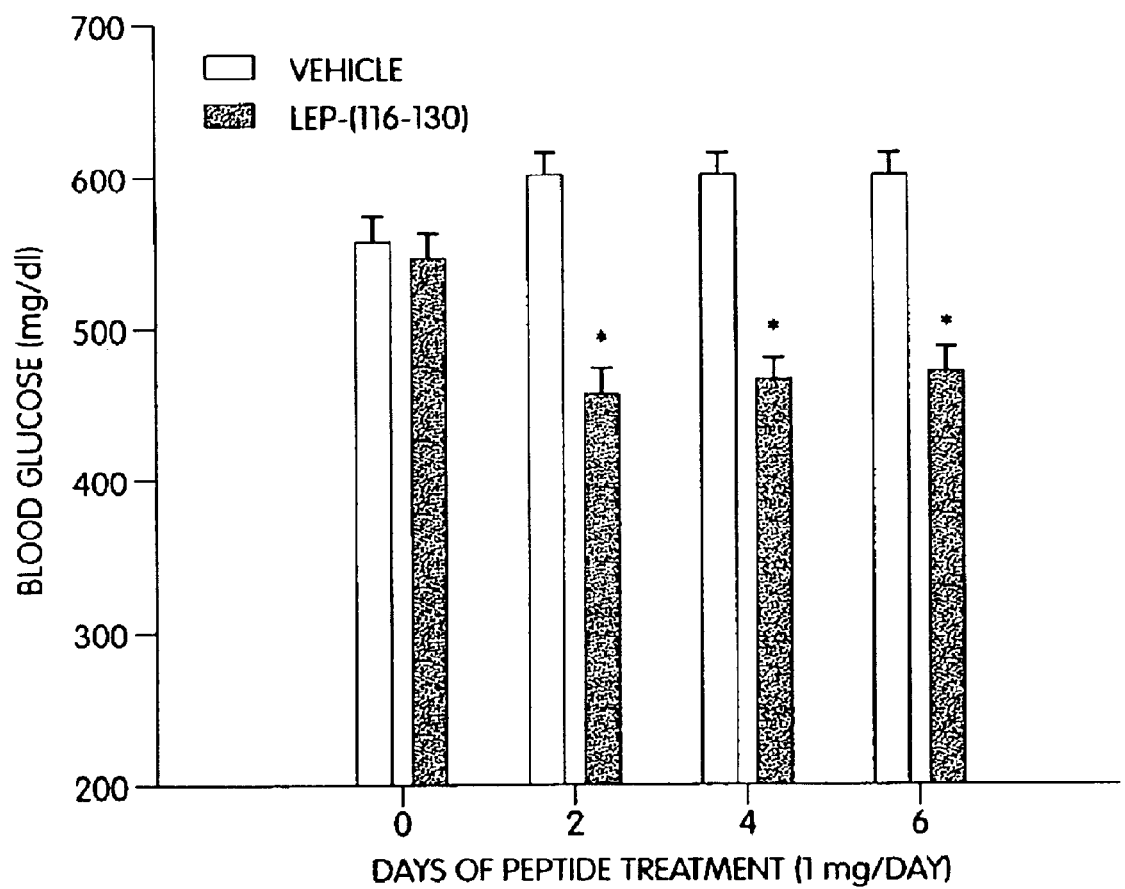
FIG. 12 is a graphic representation of the effects of LEP(116–130) peptide on blood glucose levels in genetically obese female C57BLKS/J-m db/db mice.

Effects of LEP(116–130) on Blood Glucose and Thermogenesis in db/db Mice:

FIG. 12 depicts the effects of LEP(116–130) on blood glucose levels in female C57BLKS/J-m db/db mice. Mice were treated with vehicle or 1 mg (ip) LEP(116–130) for 7 days. Blood was drawn from the tail vein at the beginning of the study (day 0) and after 2, 4, and 6 days of treatment. Each bar and vertical line represents the mean q SEM glucose level in a group of six mice. *, Blood glucose level significantly (P<0.05) lower than vehicle-injected control level.

Figure 13A:
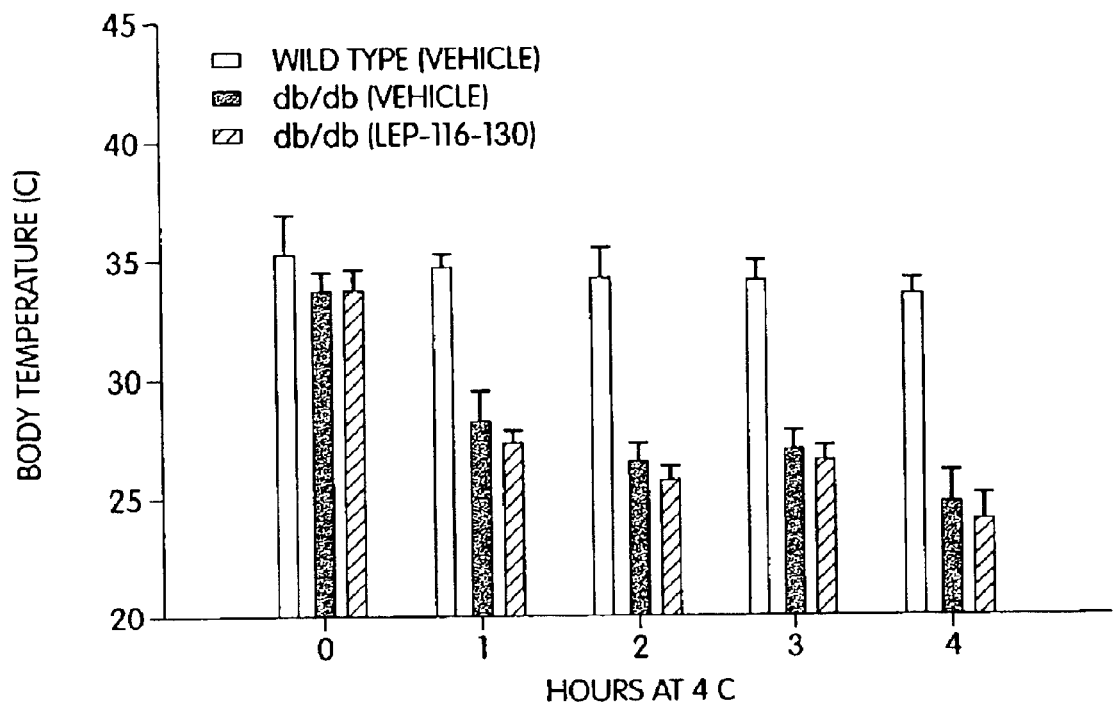
FIGS. 13A–13B are graphic representations of the effects of LEP(116–130) peptide on thermogenesis in genetically obese female C57BLKS/J-m db/db mice after 4 days and 7 days of peptide treatment.
Figure 13B:
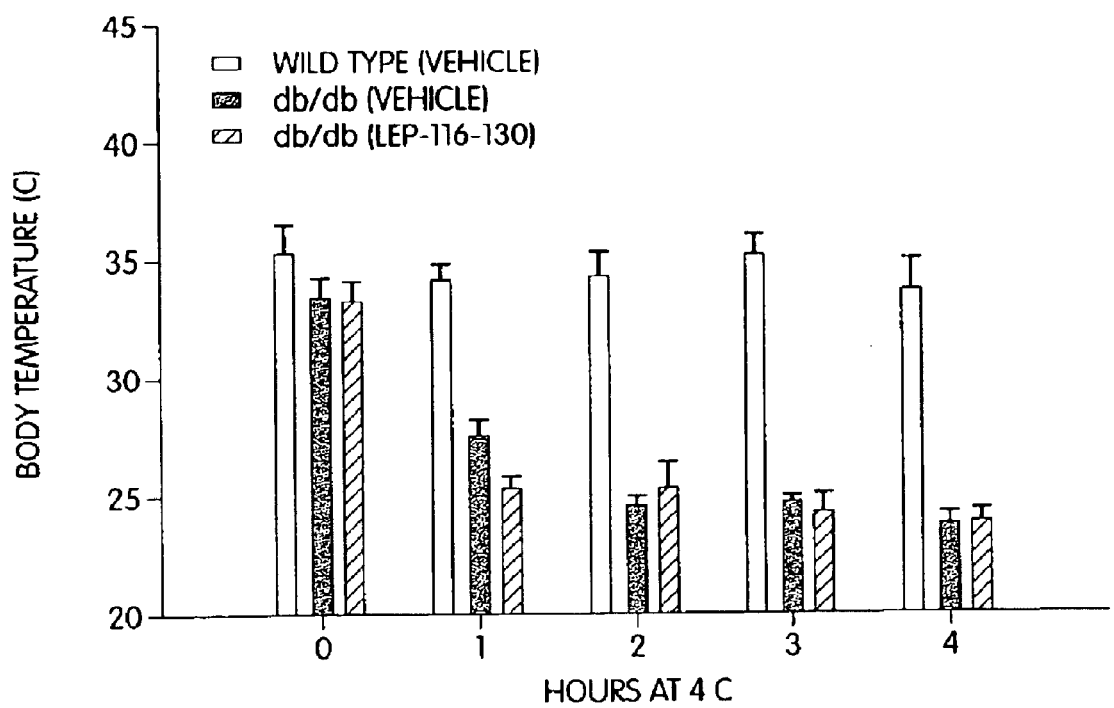

FIG. 13 depicts the effects of LEP(116–130) on thermogenesis in female C57BLKS/J-m db/db mice. Mice were treated with vehicle or 1 mg (ip) LEP(116–130) for 7 days. On days 4 (Panel A) and 7 (Panel B), the mice were placed in a cold room held at an ambient temperature of 4° C. Body temperatures were measured with a rectal probe t, 2, 3 and 4 hours later. Each bar and vertical line represents the mean±SEM core temperature of a group of six mice.

It was of interest to determine whether or not the effects of LEP(116–130) on body weight gain and food intake in db/db mice were associated with changes in glucose utilization. The results of LEP(116–130) on blood glucose levels after 2, 4 and 6 days of treatment are shown in FIG. 12. While glucose levels in vehicle-injected control mice were consistently high throughout the study (556 to 600 mg/dl), blood glucose was significantly reduced (P<0.05) by approximately 100 mg/dl after 2 days of LEP(116–130) treatment, and was sustained throughout the 7 days of the study (454 to 470 mg/dl). When the mice were withdrawn from treatment, blood glucose returned to the level of vehicle-injected control mice within 24 h.

The apparent dissociation between food intake and body weight gain observed in LEP(116–130)treated mice suggested the possibility that the peptide might be influencing thermogenesis. To test this hypothesis, we subjected wild type and C57BLKS/J-m db/db mice receiving vehicle or LEP(116–130) for 4 or 7 days to cold stress (4° C.), and assessed their responses to low ambient temperature. Abnormalities in thermoregulation were evident in both vehicle-injected control mice and mice given LEP(116–130) for 4 (FIG. 13A) or 7 (FIG. 13B) days. Wild type mice maintained a core body temperature of approximately 35.2+1.7° C. during the 4 h exposure; db/db mice injected with vehicle or LEP(116–130) for 4 or 7 days exhibited a marked decrease in core temperature after 1 h at 4° C., which was further reduced by continued exposure for an additional 3 h.

Effects of LEP(116–130) on Female Wild Type (+/+) C57BLKS/J-m Mice:

The effects of LEP(116–130) on body weight and food intake in female wild type (+1+) C57BLKS/J-m mice are summarized in Tables 3 and 4, respectively. In a pattern similar to that observed in db/db mice (Tables 1 and 2), daily administration (ip) of 1 mg LEP(116–130) for 7 days resulted in a significantly (P<0.05) reduced rate of body weight gain (Table 3) which occurred in the presence of increased (but not statistically significant) food intake (Table 4), when compared to vehicle-injected control mice.

Blood glucose levels in vehicle-injected wild type (+/+) C57BLKS/J-m mice ranged between 125±2.7 and 146±2.4 mg/dl throughout the 7 days of the study. These values were not significantly changed by treatment for 7 days with 1 mg (ip) LEP(116–130), and ranged between 127±1.6 and 149±1.1 mg/dl.

Administration of LEP(116–130) to wild type (+/+) C57BLKS/J-m mice for 4 or 7 days had no effect on their ability to thermoregulate. When stressed for 4 h at 4° C., core temperature of vehicle-injected control mice fell from 32.3±0.4° C. to 26.4±1.1° C. Core temperature of mice given LEP(116–130) fell from 31.8±0.3° C. to 28.2±0.4° C.

TABLE 3

Effects of LEP(116-130) peptide amide on body weight gain in female wild type C57BLKS/J-m mice after 7 days of treatment.

|  | Vehicle | LEP(116-130) |
|---|---|---|
| Initial weight (g)[a] | 17.7 ± 0.7 | 18.0 ± 0.9 |
| Weight after 7 days (g)[a] | 18.3 ± 0.9 | 18.2 ± 1.0 |
| Weight increase (g) | +0.6 | +0.2 |
| Percent increase | +3.4 | +1.1 |
| P[b] |  | 0.047 |

[a]Mean ± SEM (n = 6)
[b]Mean of the differences between the initial and 7-day body weight of each mouse (n = 6) in the LEP(116-130) - treated group was compared with the mean of the differences between the initial and 7-day body weight of each vehicle-injected control mouse (n = 6). The P value (2-tailed) was computed by the Wilcoxon Sign Test.

TABLE 4

Cumulative effects of LEP(116-130) peptide amide (1 mg/day, ip) on food intake in female wild type C57BLKS/J-m mice after 7 days of treatment.

| Treatment | Cumulative food intake (gm/mouse)[a] |
|---|---|
| Vehicle | 17.5 ± 0.7 |
| LEP(116-130) | 19.5 ± 0.4 |
| P[b] | 0.079 |

[a]Mean ± SEM (n = 6)
[b]The cumulative food intake by each mouse in the LEP(116-130) - treated group (n = 6) was compared to the cumulative food intake of each vehicle-injected control mouse (n = 6). The P value (2-tailed) was determined by the Wilcoxon Sign Test.

Analysis

In GT1-7 cells cotransfected with cDNA for OB-$R_b$ and the reporter gene construct HRRE-SEAP, LEP(116–130) was unable to induce SEAP activity. In addition, LEP (116–130) was unable to inhibit binding of AP-OB fusion protein to COS-7 cells expressing OB-R, even at concentrations as high as 300 μM. Our in vitro data clearly indicate that LEP(116–130) activation of OB-$R_b$ is not required for its effects in vivo.

The observation that LEP(116–130) was able to reduce body weight gain, but not food intake, in db/db mice that do not express OB-$R_b$ provides further support for a mechanism of action different from that of leptin. That the effect of LEP(116–130) on body weight was not a generalized response to peptide treatment was evident by the inability of LEP(146–160) to induce similar changes. We have not as yet determined the mechanism by which peripheral administration of LEP(116–130) reduces body weight gain in either ob/ob or db/db mice, or whether its effects would be more robust if given centrally. These questions are under active investigation.

The ability of LEP(116–130) to reduce body weight gain in db/db mice might be related to some as yet undetermined toxic side effect of the peptide. Although we cannot completely eliminate this possibility, several lines of evidence suggest that this was not the case. First, we noted no negative effect of LEP(116–130) on appetite in these mice. Their rate of food intake was similar to that of vehicle-injected control animals throughout the course of the study. Second, there were no observable ill effects of LEP (116–130) on the appearance or behavior of the mice. Their coat quality, stools and activity level appeared similar to vehicle-injected control mice. Third, the inhibitory effects of LEP(116–130) on body weight gain were apparent in the absence of any significant reduction in food intake. This suggests that mice receiving LEP(116–130) may have been more metabolically active than vehicle-injected controls. Such would not be expected if LEP(116–130) was in some way toxic.

To begin to understand the mechanism by which LEP (116–130) exerts its influence on energy balance in db/db mice, we examined its effects on blood glucose levels. The reduction in blood glucose observed in mice given LEP (116–130) for 7 days when compared to vehicle-injected control mice cannot be attributed to reduced caloric intake, since peptide-treated mice consumed approximately 15% more food than vehicle-injected controls during the course of the study. This observation suggests that, by metabolic mechanisms which may be similar to those of leptin in ob/ob mice, LEP(116–130) may also stimulate glucose utilization, and in this way help to modulate energy balance.

Worthy of note is the apparent uncoupling effect of LEP(116–130) on food intake and body weight gain in db/db mice. In contrast to what was seen in our earlier studies with ob/ob mice in which weight loss was accompanied by reduced food intake (Grasso et al., 1997. *Endocrinology* 138: 1413–1418), db/db mice given LEP(116–130) did not lose weight, but failed to gain additional weight even when their food intake was greater than that of vehicle-injected control mice. These observations suggested that LEP (116–130) may act by a mechanism related to the regulation of thermogenesis. Our data, however, argue against this hypothesis, since the observed reduction in body weight gain in LEP(116–130)-treated mice was not accompanied by any improvement in their ability to thermoregulate.

The effects of LEP(116–130) on body weight gain and food intake in wild type (+/+) mice mimicked those seen in db/db mice. In both cases, body weight gain was reduced approximately 3-fold in the presence of increased food intake. These observations suggest that the effect of LEP (116–130) on body weight gain may be the result of as yet undetermined metabolic effects that are not dependent upon or restricted to the presence of the obese phenotype.

Contrary to its effect on blood glucose in the severely hyperglycemic db/db mouse, however, administration of LEP(116–130) to wild type (+/+) mice for 7 days neither elevated nor lowered normal blood glucose levels in this animal model, suggesting an action of LEP(116–130) which is specific for the diabetic phenotype. In addition, new data with female ob/ob mice that show a similar ability of LEP(116–130) (1 mg/day, ip, 7 days) to lower blood glucose levels by approximately 100 mg/dl lends further support to the specificity of this anti-hyperglycemic action of LEP (116–130).

In summary, utilizing both in vitro and in vivo bioassay systems, our data suggest that the anti-obesity effects of a synthetic peptide amide corresponding to amino acid residues 116–130 of mouse leptin may not be mediated by activation of hypothalamic OB-$R_b$. The possibility that. LEP(116–130), which is unable to bind and activate OB-R in vitro, may be modified intravascularly in the ob/ob mouse in such a way that a conformation which enables OB-$R_b$ activation is achieved cannot be completely eliminated at this time. Such an event, however, cannot account for the effect of LEP(116–130) on body weight gain in the db/db mouse which does not express OB-$R_b$.

Unlike recombinant leptin, LEP(116–130) was effective in both leptin-deficient (ob/ob) and leptin-resistant (db/db) animal models of obesity. Since most obese humans are not leptin-deficient and have normal leptin receptors, this observation suggests that development of more potent peptide analogs or mimetics of LEP(116–130), which can augment the effects of endogenous leptin independent of hypothalamic OB-$R_b$ activation, may have potential application to the treatment of human obesity and its related dysfunctions.

Example 9

Effect of OB-3 Peptide on Blood Glucose Levels

Figure 14:
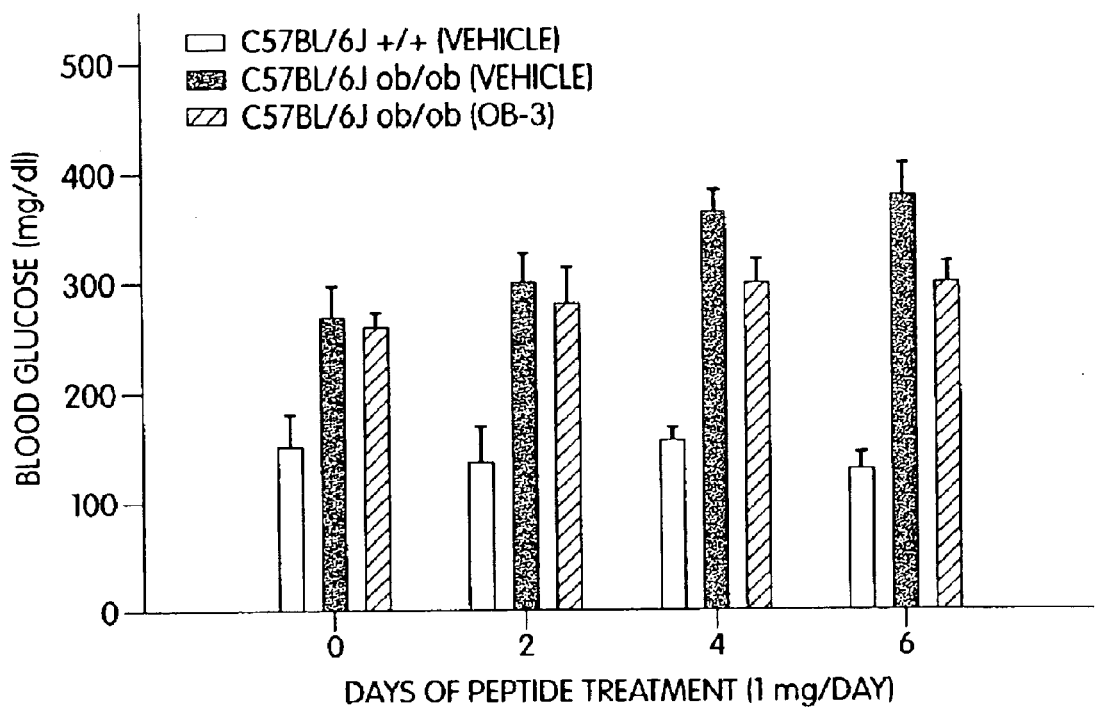
FIG. 14 is a graphic representation of the effects of synthetic OB-3 peptide on blood glucose levels in genetically obese female C57BL/6J ob/ob mice.
Figure 15:
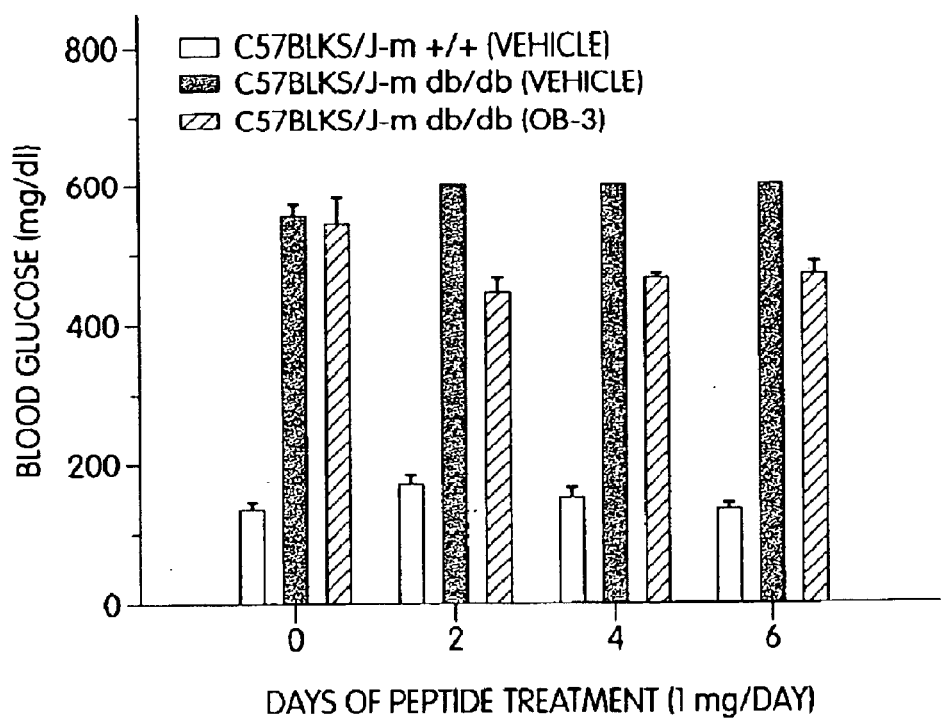
FIG. 15 is a graphic representation of the effects of synthetic OB-3 peptide on blood glucose levels in genetically obese female C57BLKS/J-m db/db mice.

FIGS. 14 and 15 depict the effect of synthetic OB-3 peptide on blood glucose levels in genetically obese female C57BL/6J ob/ob mice and C57BLKS/J-m db/db mice, respectively. OB-3 lowers blood glucose in both strains of mice.

Example 10

Epitope Mapping

Intraperitoneal (ip) administration of synthetic peptide amides corresponding to amino acids 106–140 of mouse leptin significantly reduced food intake and body weight gain in female C57BL/6J ob/ob mice. These results suggested that leptin activity was localized in domains toward its C-terminus between residues 106–140. In the present study, 14 overlapping peptides encompassing the complete sequence of secreted mouse leptin were synthesized, and their effects on body weight and food intake in female C57BL/6J ob/ob mice were assessed. When given as 7 daily 1-mg ip injections, only peptides corresponding to amino acids 106–120, 116–130 and 126–140 caused significant reductions in body weight and food intake. These results confirmed our earlier study, and suggest that in contrast to the domain encompassed by amino acids 106–140, the N-terminal of mouse leptin between amino acids 21–105 may not contain functional epitopes which can be utilized as lead compounds in the development of peripherally administered bioactive peptide analogs or nonpeptide mimetics of leptin which may have potential usefulness in treatment of the energy imbalance associated with obesity.

Herein we identify N-terminal active epitopes between amino acid residues 21–105 of mouse leptin. Using female C57BL/6J ob/ob mice and ip administration of overlapping synthetic peptide amides encompassing this domain, we were able to detect only minimal leptin-like activity between amino acid residues 71–85 and 91–105. Given our earlier results utilizing this same approach with synthetic peptides representing residues 106–167 of mouse leptin in a 28-day study (Grasso et al., 1997. *Endocrinology* 138: 1413–1418), our data suggest that, in contrast to the C-terminus of mouse leptin, the N-terminal domain between amino acid residues 21–105 may not contain functional epitopes useful in the development of peripherally administered bioactive peptide analogs or nonpeptide mimetics of leptin.

Peptide synthesis, purification and characterization. Overlapping peptide amides (FIG. 1) corresponding to residues ranging from residues 21 to 167 of mouse leptin (FIG. 1; SEQ ID NO:1) were synthesized by Quality Controlled Biochemicals, Inc. (QCB, Hopkinton, Mass.) using the fluorenylmethoxycarbonyl (FMOC)-protection scheme. See, e.g., as described in EXAMPLE 1. The peptide amides were purified to greater than 95%, and evaluated by reversed-phase HPLC (QCB). Each peptide amide was represented as a single peak in the chromatographic profile. Fidelity of synthesis was confirmed by mass spectral analysis (QCB).

Animal procedures. Feeding and weighing schedules, as well as peptide administration protocols, are as described in EXAMPLE 8, supra.

Toxicity. No obvious toxic side effects, such as reduced activity level, changes in coat quality or stool consistency (diarrhea), or decreased water intake were associated with any of the aid peptides tested in this study. Body temperature, determined by rectal probe, was also unchanged by peptide treatment.

Statistical analysis. Changes in body weight and differences in food intake between peptide-treated and vehicle-injected control mice were analyzed by analysis of variance (ANOVA) and considered significant when $P<0.05$.

Effects of Leptin-related Synthetic Peptide Amides on Body Weight:

Female ob/ob mice (n=6 per group) were given a single ip injection of 0.2 ml of vehicle (PBS, pH 7.2) or leptin-related synthetic peptide amide in 0.2 ml PBS for 7 consecutive days. Daily changes in body weight compared to pretreatment weights in both vehicle-injected control and peptide-treated mice are shown in FIG. 4. Body weight gain in mice receiving peptides corresponding to amino acids 71–85 (FIG. 4F) or 91–105 (FIG. 4H), when compared to vehicle-injected control mice, was reduced, but not significantly ($P>0.05$). There was no evidence of weight loss in response to peptide treatment. Mice receiving peptides corresponding to amino acid residues 106–120 (FIG. 4I), 116–130 (FIG. 4J), or 126–140 (FIG. 4K), however, consistently lost weight during the course of the study, and weighed significantly ($P=0.01$) less after 7 days of peptide treatment. The effects of each peptide on body weight after 7 days of administration are summarized in Table 5.

TABLE 5

Effects of leptin-related synthetic peptide amides (1 mg/day, ip) on body weight of female ob/ob mice after 7 days of treatment.

| Treatment | Weight gain (+) or loss (−) (g) | Percent heavier (+) or lighter (−) than initial weight |
|---|---|---|
| Vehicle | +5.6 | +25.6 |
| LEP(21-35) | +6.2 | +24.0 |
| LEP(31-45) | +6.6 | +26.6 |
| LEP(41-55) | +5.9 | +27.6 |
| LEP(51-65) | +6.4 | +25.0 |
| LEP(61-75) | +5.9 | +24.0 |
| LEP(71-85) | +5.0 | +20.0 |
| LEP(81-95) | +6.2 | +26.0 |
| LEP(91-105) | +5.2 | +18.6 |
| LEP(106-120) | −6.1[a] | −12.0 |
| LEP(116-130) | −8.3[a] | −14.4 |
| LEP(126-140) | −6.0[a] | −10.2 |
| LEP(136-150) | +5.4 | +25.6 |
| LEP(146-160) | +6.8 | +28.0 |
| LEP(156-167) | +5.7 | +22.6 |

[a]$P = 0.01$.

Effects of Leptin-related Synthetic Peptide Amides on Food Intake:

Cumulative food intake (gm food consumed/mouse, n=6 per group) by vehicle-injected control and peptide-treated mice is shown in Table 6. During 7 days of peptide treatment, food intake by mice receiving LEP(71–85), LEP(91–105), LEP(106–120), LEP(116–130), or LEP(12–140) was significantly ($P=0.01$) less than vehicle-injected control mice.

TABLE 6

Effects of leptin-related synthetic peptide amides (1 mg/day, ip) on cumulative food intake in female ob/ob mice during 7 days of treatment.

| Treatment | Cumulative food intake (gm/mouse)[a] |
|---|---|
| Vehicle | 40.5 ± 1.5 |
| LEP(21-35) | 39.1 ± 1.0 |
| LEP(31-45) | 39.5 ± 0.6 |
| LEP(41-55) | 39.4 ± 1.5 |
| LEP(51-65) | 40.7 ± 0.6 |
| LEP(61-75) | 44.6 ± 2.3 |
| LEP(71-85) | 35.5 ± 1.1[b] |
| LEP(81-95) | 39.5 ± 1.1 |
| LEP(91-105) | 36.1 ± 0.7[b] |
| LEP(106-120) | 34.5 ± 1.1[b] |
| LEP(116-130) | 34.7 ± 0.7[b] |
| LEP(126-140) | 34.7 ± 1.3[b] |
| LEP(136-150) | 38.7 ± 1.6 |
| LEP(146-160) | 40.5 ± 1.0 |
| LEP(156-167) | 40.3 ± 0.6 |

[a]Mean ± SEM
[b]$P = 0.01$

Concentration-related Effects of LEP(116–130) Peptide Amide:

To address whether the observed effects of our active peptides on body weight gain and food intake in female ob/ob mice were concentration-related, a dose-response study was done with LEP(116–130). The effects of LEP (116–130), given ip at 0.5 mg, 1.0 mg and 1.5 mg per day for 7 days, are shown in Table 7. Significant (P=0.01) and dose-related weight loss was seen at 0.5 mg and 1.0 mg LEP(116–130), and increased only slightly at 1.5 mg, suggesting that the maximal effects of this peptide were achieved at 1.0 mg. Dose-related reduction in food intake was observed at all concentrations of LEP(116–130) tested, but reached significance (P=0.01) only at concentrations of 1.0 mg and 1.5 mg.

TABLE 7

Concentration-related effects of LEP(116-130) on body weight gain and food intake in female ob/ob mice after 7 days of treatment.

| Treatment | Percent heavier (+) or lighter (−) than initial weight | Food intake (gm/mouse/7 days)[a] |
|---|---|---|
| Vehicle | +26.3 | 43.6 ± 1.1 |
| LEP(116-130) (mg/day) | | |
| 0.5 | −6.1[b] | 41.5 ± 0.7 |
| 1.0 | −14.0[b] | 35.2 ± 1.3[b] |
| 1.5 | −14.7[b] | 30.8 ± 0.4[b] |

[a]Mean ± SEM
[b]P = 0.01.

Analysis

Samson et al., 1996 (see, *Endocrinology* 137: 5182–5185) reported only minimal inhibition of food intake in non-obese adult male Sprague-Dawley rats by central administration of a 35 amino acid fragment of leptin (amino acid residues 116–167), which encompasses our active domain. Our data (Table 6 and FIG. 4L, 4M, 4N), however, suggest that the presence of residues 141–167 in 116–167 may have attenuated its satiety effect. Since these authors did not test any of their peptides in an obese animal model, we do not know if the 116–167 peptide would have shown greater activity in the presence of the obese phenotype, as has been NUB demonstrated by a number of laboratories for leptin. See, e.g., Halaas et al., 1995 *Science* 269: 543–546; Pellymounter et al., 1995 *Science* 269: 540–543; Campfield. et al., 1995 *Science* 269: 546–549.

In that same study (see, Samson et al., 1996 *Endocrinology* 137: 5182–5185), an N-terminal leptin fragment (amino acid residues 22–56) significantly inhibited food intake in non-obese adult male rats when administered into the lateral cerebroventricle. In contrast to this observation, however, none of our N-terminal peptides encompassing this region were active when administered peripherally to female C57BL/6J ob/ob mice. A number of factors could account for this discrepancy, some of which are related to the route of administration used in each study (peripheral vs. central), i.e., (i) N-terminal fragments may be more highly susceptible to proteolytic degradation in the circulation than are C-terminal fragments; (ii) N-terminal fragments may have higher affinity for leptin-binding proteins than C-terminal fragments, thus reducing the actual concentration of active N-terminal fragments; and (iii) N-terminal fragments may not be transported across the blood-brain barrier as efficiently as C-terminal fragments. It is also possible that N-terminal fragments may display a higher level of species specificity than do C-terminal fragments, and may be of lower potency than C-terminal fragments in the presence of an obese phenotype. Each of these questions requires further investigation.

A number of laboratories have turned their attention to the C-terminus of leptin. The importance of arginine (R) 128 to the biological activity of human leptin has recently been demonstrated. See, e.g., Verploegen et al., 1997. *FEBS Lett* 405: 237–240. In that study, peripheral administration of an arginine to glutawine (Q) mutant (R128Q) of human leptin to C57BL/6J ob/ob mice was unable to inhibit body weight gain and reduce food intake when compared to wild-type human leptin. This mutant also stimulated weight gain when given to nonobese C57BL/6J mice. In another study, a pool of amino acid peptides encompassing amino acid residues 127–167 of leptin was found to inhibit food intake and regulate thermogenesis in mice. See, e.g., Martinez et al., 1996. *J Physiol Biochem* 52: 123–124. Taken together, these results also support the notion that the epitope(s) contributing to leptin's effects on energy balance, when administered peripherally, may be localized toward its C-terminus.

We used peripherally administered synthetic peptides in an effort to define active epitopes at the N-terminus of mouse leptin between amino acid residues 21 and 105. In contrast to our earlier studies with C-terminal peptides of leptin (see, Weigle et al., 1995. *J Clin Invest* 96: 2065–20708), none of the N-terminal peptides encompassing amino acid residues 21–105 were effective in inducing weight loss when administered intraperitoneally to female ob/ob C57BL/6J mice. Two of the peptides in this region, however, LEP(71–85) and LEP(91–105), were able to significantly reduce food intake, and this anorexic effect was reflected by a trend towards a reduced rate of weight gain by mice receiving these peptides when compared to weight gain by vehicle-injected control mice. The inability of LEP(71–85) and LEP(91–105) to induce actual weight loss in the presence of reduced food intake, however, suggests that these peptides may be of lower potency than LEP(106–120), LEP (116–130) and LEP(126–140), or that the pathway by which they alter energy expenditure in the ob/ob mouse differs from that of LEP(106–120), LEP(116–130) and LEP (126–140).

Our data suggest that the entire sequence of mouse leptin may not be required for its action on energy balance, and that synthetic peptides representing active domains may have the ability to mimic, although at lower potency, the effects of intact leptin on body weight gain and food intake. In the original leptin study by Halaas et al. 1995 (see, *Science* 269: 543–546), daily ip administration of 300 μg (18.75 nmol) of recombinant human or mouse leptin (i) reduced initial body weight in ob/ob mice by approximately 15% in 7 days, and (ii) stabilized food intake at 40% of vehicle-injected control mice after 4 days. Our most active peptide amides, LEP (106–120), LEP(116–130) and LEP(126–140), given daily at 1 mg (609,641 and 607 nmol, respectively), caused weight losses of 12.0%, 14.1% and 10.2%, respectively, after 7 days, and reduced food intake by 14.8%, 14.3% and 14.3%, respectively. The lower potency of our peptides was not unexpected, however, and is commonly seen with peptides since truncation or fragmentation of a protein often removes structural motifs which are essential for the full expression of its activity. See, e.g., Hruby and Bonner. 1994 *Methods Mol Biol* 35: 201–240.

It has become evident that leptin has multiple biological actions, only one of which is the regulation of energy balance. See, e.g., Fruhbeck et al., 1998 *Clin Physiol* 18: 399–419. A complex role for leptin in whole-body physiology and pathophysiology is just beginning to be defined Thus, the possibility that specific domains of the leptin molecule may be involved in the effects of leptin on biological actions other than food intake and body weight gain, i.e., reproduction and the immunological response, suggests new studies in which the utilization of natural and synthetic peptide fragments of leptin may provide useful information.

General Comments.

The protocols included herein represent rational and proven approaches to the design of highly potent peptide analogs, as we have proven with previous work on FSH-, LH- and FSH receptor-related peptides. Therefore, their application to leptin, and the difficulties which may be encountered in peptide synthesis and purification, are well within the scope of the invention.

Screening of peptide analogs to determine biological activity, i.e., effects on weight gain and food intake, will be done using a related series of peptides, i.e., truncated analogs, overlapping peptides, D-amino acid substituted, cyclized analogs, and so forth, as described supra. It is anticipated that preliminary screening will take 14 days for each peptide, but will be lengthened if peptide effects appear transient in nature (see above).

Potential Limitations and Alternative Strategies:

As stated above, the most prominent limitation associated with these studies may be related to the synthesis of difficult peptide sequences. In this regard, visual analysis of a peptide sequence prior to synthesis, in conjunction with a number of available tables which predict difficult couplings, will enable one skilled in the art to make modifications in the synthesis protocol, which can significantly reduce coupling time and improve the purity of the peptide product. Other approaches to difficult syntheses may be possible, provided they do not alter activity. These strategies include shortening the sequence, decreasing the number of hydrophobic residues, or minimizing the number of difficult residues by amino acid substitutions, i.e., serine for cysteine; norleucine for methionine; lysine for arginine; tyrosine, phenylalanine or leucine for tryptophan.

Solubility problems may also be encountered, depending on the peptide sequence. Analysis of hydrophobicity prior to synthesis may indicate that certain amino acid substitutions, or synthesis of the peptide as a C-terminal amide or with a free C-terminus, will improve its solubility. The addition of a set of polar residues to a peptide may also improve solubility: glutamine-glutamnine added to the N- or C-terminus of acidic peptides, or lysine-lysine to the N- or C-terminus of basic peptides. These modifications should be made with caution, however, to assure that the activity of the peptide will not be altered.

The effects of peripheral and central administration of leptin on obesity and its associated dysfunctions in the C57BL/6J ob/ob mouse have been validated by a number of independent laboratories, and are well characterized. See, e.g., Halaas, et al., Science, 269: 543–546 (1995); Pelleymounter, et al., Science, 269: 540–543 (1995); Weigle, et al., J Clin Invest, 96: 2065–2070 (1995); Barash, et al., Endocrinology, 137: 3144–3147 (1996). For these reasons, we felt that this animal model was the most appropriate system with which to begin our studies on food intake and body weight gain in response to peptides corresponding to restricted sequences within the mouse leptin molecule. However, obesity in most humans is not associated with leptin deficiency (as seen in the C57BL/6J ob/ob mouse), but rather with leptin resistance, the exact cause of which is not completely understood. See, e.g., Lonnqvist, et al., Nat Med, 1: 950–953 (1995); Misra and Garg. J Invest Med, 44: 540–548 (1996); Banks, et al., Peptides, 17: 305–311 (1996); Caro, et al., Lancet, 348: 159–161 (1996). Thus, this model may be limited to the extent with which the results of leptin-related peptides on food intake and body weight gain in the C57BL/6J ob/ob mouse are relevant to human obesity. There is the possibility, however, that administration of biologically stabile leptin analogs or mimetics of even higher potency than leptin may be able to overcome, at least in part, the leptin resistance of these individuals.

Recently, leptin-deficient obese humans with mutations in the ob gene, or markers flanking the ob gene, have been identified. See, e.g., Montague, et al., Int J Obes, 22: 200–205 (1998); Considine, et al., Biochem Biophys Res Commun, 220: 735–739 (1996); Hager, et al., Int J Obes, 22: 200–205 (1998); Storbel, et al., Nat Gen, 18: 213–215 (1998); Clement, et al., Diabetes, 45: 687–690 (1996); Reed, et al., Diabetes, 45: 691–694 (1996). Although these mutations are not identical to those in the mouse ob gene, the effects of low leptin levels in this subgroup of obese individuals may be related physiologically to the effects of leptin deficiency seen in the C57B 1 /6J ob/ob mouse. Thus, administration of leptin analogs or mimetics of even higher potency than leptin may be able to augment the deficiency in endogenous leptin in these individuals, and correct, at least in part, the energy imbalance responsible for their obesity.

Equivalents

From the foregoing detailed description of the specific embodiments of the invention, it should be apparent that unique compositions and methods of use for synthetic leptin-related peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of compositions and methods of use of synthetic leptin-related peptides, or derivatives, analogs, or variants thereof, is believed to be a matter of routine for a person of ordinary skill in the art with knowledge of the embodiments described herein.

Leptin Peptides—Single Letter Amino Acid Codes (i) S C S L P Q T [SEQ ID NO:2];
(ii) A V P I Q K V Q D D T K T L I [SEQ ID NO:3];
(iii) T K T L I K T I V T R I N D I [SEQ ID NO:4];
(iv) R I N D I S H T Q S V S A K Q [SEQ ID NO:5];
(v) V S A K Q R V T G L D F I P G [SEQ ID NO:6];
(vi) D F I P G L H P I L S L S K M [SEQ ID NO:7];
(vii) S L S K M D Q T L A V Y Q Q V [SEQ ID NO:8];
(viii) V Y Q Q V L T S L P S Q N V L [SEQ ID NO:9];
(ix) S Q N V L Q I A N D L E N L R [SEQ ID NO:10];
(x) D L L H L L A F S K S C S L P [SEQ ID NO:11];
(xi) S C S L P Q T S G L Q K P E S [SEQ ID NO:12];
(xii) Q K P E S L D G V L E A S L Y [SEQ ID NO:13];
(xiii) E A S L Y S T E V V A L S R L [SEQ ID NO:14];
(xiv) A L S R L Q G S L Q D I L Q Q [SEQ ID NO:15];
(xv) D I L Q Q L D V S P E C [SEQ ID NO:16];
(xvi) S C H L P W A [SEQ ID NO:18]

SEQUENCE LISTING

<160> NUMBER OF SEQ ID NOS: 18

<210> SEQ ID NO 1
<211> LENGTH: 167
<212> TYPE: PRT
<213> ORGANISM: Mus sp.

<400> SEQUENCE: 1

Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ala Lys Gln Arg Val Thr Gly Leu Asp Phe Ile Pro
        50                  55                  60

Gly Leu His Pro Ile Leu Ser Leu Ser Lys Met Asp Gln Thr Leu Ala
65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
        115                 120                 125

Glu Ser Leu Asp Gly Val Leu Glu Ala Ser Leu Tyr Ser Thr Glu Val
    130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165

<210> SEQ ID NO 2
<211> LENGTH: 7
<212> TYPE: PRT
<213> ORGANISM: Mus sp.

<400> SEQUENCE: 2

Ser Cys Ser Leu Pro Gln Thr
 1               5

<210> SEQ ID NO 3
<211> LENGTH: 15
<212> TYPE: PRT
<213> ORGANISM: Mus sp.

<400> SEQUENCE: 3

Ala Val Pro Ile Gln Lys Val Gln Asp Asp Thr Lys Thr Leu Ile
 1               5                  10                  15

<210> SEQ ID NO 4
<211> LENGTH: 15
<212> TYPE: PRT
<213> ORGANISM: Mus sp.

<400> SEQUENCE: 4

Thr Lys Thr Leu Ile Lys Thr Ile Val Thr Arg Ile Asn Asp Ile
 1               5                  10                  15

```
<210> SEQ ID NO 5
<211> LENGTH: 15
<212> TYPE: PRT
<213> ORGANISM: Mus sp.

<400> SEQUENCE: 5

Arg Ile Asn Asp Ile Ser His Thr Gln Ser Val Ser Ala Lys Gln
  1               5                  10                  15

<210> SEQ ID NO 6
<211> LENGTH: 15
<212> TYPE: PRT
<213> ORGANISM: Mus sp.

<400> SEQUENCE: 6

Val Ser Ala Lys Gln Arg Val Thr Gly Leu Asp Phe Ile Pro Gly
  1               5                  10                  15

<210> SEQ ID NO 7
<211> LENGTH: 15
<212> TYPE: PRT
<213> ORGANISM: Mus sp.

<400> SEQUENCE: 7

Asp Phe Ile Pro Gly Leu His Pro Ile Leu Ser Leu Ser Lys Met
  1               5                  10                  15

<210> SEQ ID NO 8
<211> LENGTH: 15
<212> TYPE: PRT
<213> ORGANISM: Mus sp.

<400> SEQUENCE: 8

Ser Leu Ser Lys Met Asp Gln Thr Leu Ala Val Tyr Gln Gln Val
  1               5                  10                  15

<210> SEQ ID NO 9
<211> LENGTH: 15
<212> TYPE: PRT
<213> ORGANISM: Mus sp.

<400> SEQUENCE: 9

Val Tyr Gln Gln Val Leu Thr Ser Leu Pro Ser Gln Asn Val Leu
  1               5                  10                  15

<210> SEQ ID NO 10
<211> LENGTH: 15
<212> TYPE: PRT
<213> ORGANISM: Mus sp.

<400> SEQUENCE: 10

Ser Gln Asn Val Leu Gln Ile Ala Asn Asp Leu Glu Asn Leu Arg
  1               5                  10                  15

<210> SEQ ID NO 11
<211> LENGTH: 15
<212> TYPE: PRT
<213> ORGANISM: Mus sp.

<400> SEQUENCE: 11

Asp Leu Leu His Leu Leu Ala Phe Ser Lys Ser Cys Ser Leu Pro
  1               5                  10                  15

<210> SEQ ID NO 12
<211> LENGTH: 15
```

<212> TYPE: PRT
<213> ORGANISM: Mus sp.

<400> SEQUENCE: 12

Ser Cys Ser Leu Pro Gln Thr Ser Gly Leu Gln Lys Pro Glu Ser
1               5                   10                  15

<210> SEQ ID NO 13
<211> LENGTH: 15
<212> TYPE: PRT
<213> ORGANISM: Mus sp.

<400> SEQUENCE: 13

Gln Lys Pro Glu Ser Leu Asp Gly Val Leu Glu Ala Ser Leu Tyr
1               5                   10                  15

<210> SEQ ID NO 14
<211> LENGTH: 15
<212> TYPE: PRT
<213> ORGANISM: Mus sp.

<400> SEQUENCE: 14

Glu Ala Ser Leu Tyr Ser Thr Glu Val Val Ala Leu Ser Arg Leu
1               5                   10                  15

<210> SEQ ID NO 15
<211> LENGTH: 15
<212> TYPE: PRT
<213> ORGANISM: Mus sp.

<400> SEQUENCE: 15

Ala Leu Ser Arg Leu Gln Gly Ser Leu Gln Asp Ile Leu Gln Gln
1               5                   10                  15

<210> SEQ ID NO 16
<211> LENGTH: 12
<212> TYPE: PRT
<213> ORGANISM: Mus sp.

<400> SEQUENCE: 16

Asp Ile Leu Gln Gln Leu Asp Val Ser Pro Glu Cys
1               5                   10

<210> SEQ ID NO 17
<211> LENGTH: 167
<212> TYPE: PRT
<213> ORGANISM: Homo sapiens

<400> SEQUENCE: 17

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala

```
                       100                 105                 110
Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 18
<211> LENGTH: 7
<212> TYPE: PRT
<213> ORGANISM: Homo sapiens

<400> SEQUENCE: 18

Ser Cys His Leu Pro Trp Ala
  1               5
```

We claim:

1. A purified leptin peptide consisting of the amino acid sequence selected from the group consisting of SEQ ID NOS: 2 and 18, wherein said peptide is a substantially homogenous preparation, and wherein said peptide modulates body mass.

2. The leptin peptide of claim 1, wherein the leptin peptide does not bind to the leptin receptor.

3. The leptin peptide of claim 1, wherein the leptin peptide can cross the blood brain barrier.

4. A composition comprising the leptin peptide of claim 1, and a pharmaceutically acceptable carrier.

5. A purified peptide which is an OB-3 peptide selected from the group consisting of: amino acid residues [116]Ser-Cys-Ser-Leu-Pro-Gln-Thr[122] of mouse leptin protein (SEQ ID NO:2) and [116]Ser-Cys-His-Leu-Pro-Trp-Ala[122] of human leptin protein (SEQ ID NO: 18).

6. An isolated leptin peptide consisting of an amino acid sequence selected from the group consisting of:

SEQ ID NO: 10;

SEQ ID NO:2; and

SEQ ID NO:18 wherein said peptide reduces food intake.

* * * * *

UNITED STATES PATENT AND TRADEMARK OFFICE
CERTIFICATE OF CORRECTION

PATENT NO. : 6,777,388 B1  Page 1 of 1
APPLICATION NO. : 09/377081
DATED : August 17, 2004
INVENTOR(S) : Patricia Grasso et al.

It is certified that error appears in the above-identified patent and that said Letters Patent is hereby corrected as shown below:

Page 1, (73), the Assignee should be: "Albany Medical College" (US)

Albany, NY (US)

Signed and Sealed this

Twenty-sixth Day of October, 2010

David J. Kappos
*Director of the United States Patent and Trademark Office*